US009315467B2

(12) United States Patent
Almstead et al.

(10) Patent No.: US 9,315,467 B2
(45) Date of Patent: Apr. 19, 2016

(54) COMPOUNDS FOR NONSENSE SUPPRESSION, AND METHODS FOR THEIR USE

(75) Inventors: Neil Almstead, Princeton, NJ (US); Gary M. Karp, Princeton Junction, NJ (US); Richard Wilde, Somerville, NJ (US); Ellen Welch, Califon, NJ (US); Hongyu Ren, Dayton, NJ (US)

(73) Assignee: PTC Therapeutics, Inc., South Plainfield, NJ (US)

( * ) Notice: Subject to any disclaimer, the term of this patent is extended or adjusted under 35 U.S.C. 154(b) by 531 days.

(21) Appl. No.: 11/577,189

(22) PCT Filed: Oct. 13, 2005

(86) PCT No.: PCT/US2005/036764
§ 371 (c)(1),
(2), (4) Date: Feb. 6, 2008

(87) PCT Pub. No.: WO2006/044505
PCT Pub. Date: Apr. 27, 2006

(65) Prior Publication Data
US 2008/0119473 A1     May 22, 2008

Related U.S. Application Data

(60) Provisional application No. 60/617,670, filed on Oct. 13, 2004, provisional application No. 60/617,633, filed on Oct. 13, 2004, provisional application No. 60/617,634, filed on Oct. 13, 2004, provisional application No. 60/617,655, filed on Oct. 13, 2004, provisional application No. 60/617,653, filed on Oct. 13, 2004, provisional application No. 60/624,170, filed on Nov. 3, 2004.

(51) Int. Cl.
| | | |
|---|---|---|
| A61K 31/53 | (2006.01) |
| C07D 239/42 | (2006.01) |
| C07D 401/04 | (2006.01) |
| A61K 31/435 | (2006.01) |
| C07D 231/12 | (2006.01) |
| C07D 233/64 | (2006.01) |
| C07D 249/08 | (2006.01) |
| C07D 261/08 | (2006.01) |
| C07D 263/32 | (2006.01) |
| C07D 271/06 | (2006.01) |
| C07D 277/30 | (2006.01) |
| C07D 285/12 | (2006.01) |
| C07D 307/68 | (2006.01) |
| C07D 333/24 | (2006.01) |
| C07D 413/12 | (2006.01) |
| C07F 9/653 | (2006.01) |
| C07D 403/04 | (2006.01) |
| C07D 405/04 | (2006.01) |
| C07D 409/04 | (2006.01) |
| C07D 413/04 | (2006.01) |

(52) U.S. Cl.
CPC ............ *C07D 231/12* (2013.01); *C07D 233/64* (2013.01); *C07D 249/08* (2013.01); *C07D 261/08* (2013.01); *C07D 263/32* (2013.01); *C07D 271/06* (2013.01); *C07D 277/30* (2013.01); *C07D 285/12* (2013.01); *C07D 307/68* (2013.01); *C07D 333/24* (2013.01); *C07D 401/04* (2013.01); *C07D 403/04* (2013.01); *C07D 405/04* (2013.01); *C07D 409/04* (2013.01); *C07D 413/04* (2013.01); *C07D 413/12* (2013.01); *C07F 9/65306* (2013.01)

(58) Field of Classification Search
None
See application file for complete search history.

(56) References Cited

U.S. PATENT DOCUMENTS

| 3,153,017 A | * | 10/1964 | Caldwell et al. ............... 528/335 |
| 5,022,915 A | * | 6/1991 | Prisbylla ........................ 504/225 |
| 5,521,189 A | | 5/1996 | Boykin et al. |

FOREIGN PATENT DOCUMENTS

| SU | 1063100 | * | 6/1985 | |
| WO | WO 95/19358 | * | 7/1995 | .......... C07D 401/04 |
| WO | 98/15532 A1 | | 4/1998 | |
| WO | WO 03/016280 A1 | | 2/2003 | |
| WO | 2004/014865 A1 | | 2/2004 | |
| WO | WO 2004/074244 A2 | | 9/2004 | |

OTHER PUBLICATIONS

STN Report (Accession No. 1985:586968) 1985.*
Vollhardt et al (Organic Chemistry, 4th Edition, p. 817, 2002).*
Zhang et al (Weed Science 48:755-760, 2000).*
STN Search Report (Accession No. 1965:9726).*
STN Search Report (Accession No. 1995:827724).*
Tagat et al (Bioorg Med Chem Lett 5:2143-2146, 1995).*
Kumar et al (Eur J Med Chem 30(2):99-106, 1995).*
CAS RN 70484-39-8 (entered into STN Nov. 16, 1984).*
CAS RN 160522-99-6 (entered into STN Jan. 31, 1995).*
CAS RN 205760-87-8 (entered into STN May 21, 1998).*

(Continued)

*Primary Examiner* — Craig Ricci
(74) *Attorney, Agent, or Firm* — Hoffmann & Baron, LLP

(57) ABSTRACT

The present invention relates to methods, compounds, and compositions for treating or preventing diseases associated with nonsense mutations in an mRNA by administering the compounds or compositions of the present invention. More particularly, the present invention relates to methods, compounds, and compositions for suppressing premature translation termination associated with a nonsense mutation in an mRNA.

8 Claims, 3 Drawing Sheets

(56) References Cited

OTHER PUBLICATIONS

International Search Report for PCT/US2005/036764 mailed on Apr. 3, 2006.

Harris, Roger L. N. et al., "The Effect of C-2-Carboxyphenyl Derivatives of Certain Heterocyclic Compounds on Root Geotropism in Cress Seedlings," Pestic. Sri. 1980, 11(4), 439-445.

Mehta, Line K. et al., "Synthesis of some unsymmetrical 2,6-diphenylpyridines for conjugation with analogues of the metal binding unit of bieomycin," J. Chem, Research (S), 2000, 502-503.

Spychala, J. et al., "Synthesis of dicationic diaryitriazines nucleic acid binding agents," Eur J Med Chem (1994) 29, 363-367.

Boykin, DW et al., "Anti-Pneumocystis carinii pneumonia activity of dicationic diaryl methylpyrimidines," Eur J Med Chem (1997) 32. 965-972.

Kumar, A. et al., "Anti-Pneumocystis carinii pneumonia activity of dicationic 2,4-dialylpyrimidines," Eur J Med Chem (1996) 31, 767-773.

Bajic, Miroslav, and Boykin, David W., "Synthesis of 2,4-BIS[4-(5-Amidino and 5-Substitutedamidino-2-Benzimidazoyl)Pyrimidines," Heterocyclic Communications, Department of Chemistry and Center for Biotechnology and Drug Design, Georgia State University, (1995) pp. 225-230, vol. 1 No. 4.

Murphy, Peter M. et al., "Biarylpyrimidines: a new class of ligand for high-order DNA recognition," Chem Commun., The Royal Society of Chemistry (2003), 1160-1161.

Kumar, A. et al., "Synthesis of dicationic diarylpyridiries as nucleic-acid binding agents," Eur J Med Chem (1995) 30, 99-106.

Schultheiss, N. & Bosch, E., "Facile Synthesis of Diarylpyrazines Using Suzuki Coupling of Dichloropyrazines With Aryl Boronic Acids," Heterocycles, vol. 60, No. 8, 2003, pp. 1891-1897, Department of Chemistry, Southwest Missouri State University, Springfield, MO 65804, USA.

Tagat, Jayaram R. et al., "Synthetic Inhibitors of Interleukin-6 II: 3,5-Diaryl Pyridines and Meta-Terphenyls," Bioorganics & Medicinal Chemistry Letters, vol. 5, No. 18, pp. 2143-2146, 1995.

\* cited by examiner

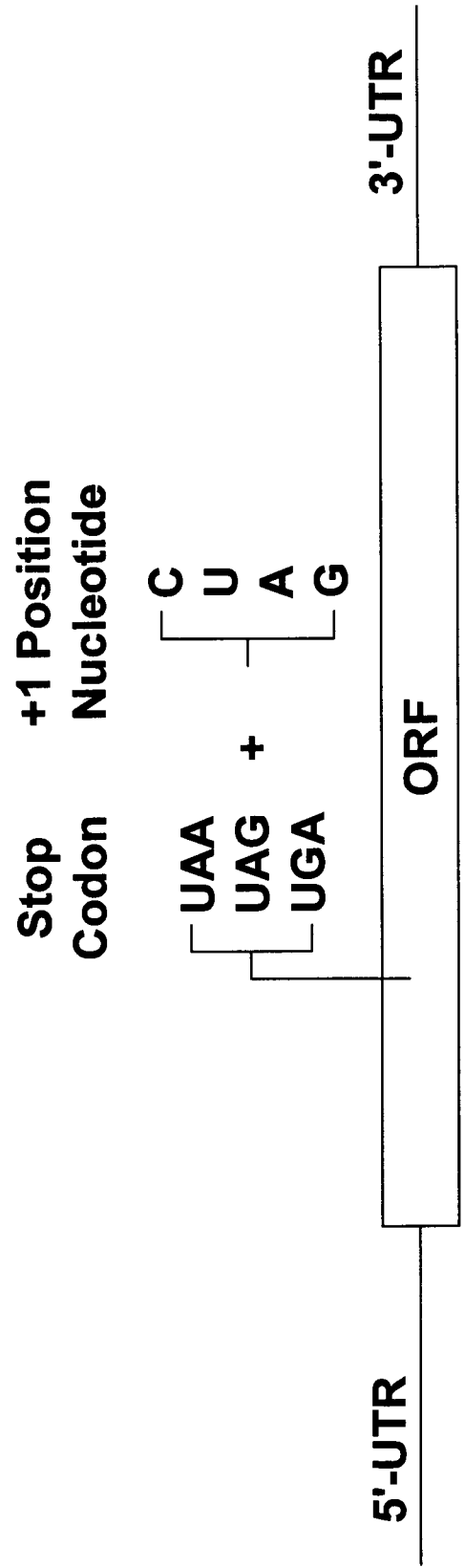
Figure 1: Luminescence Assay

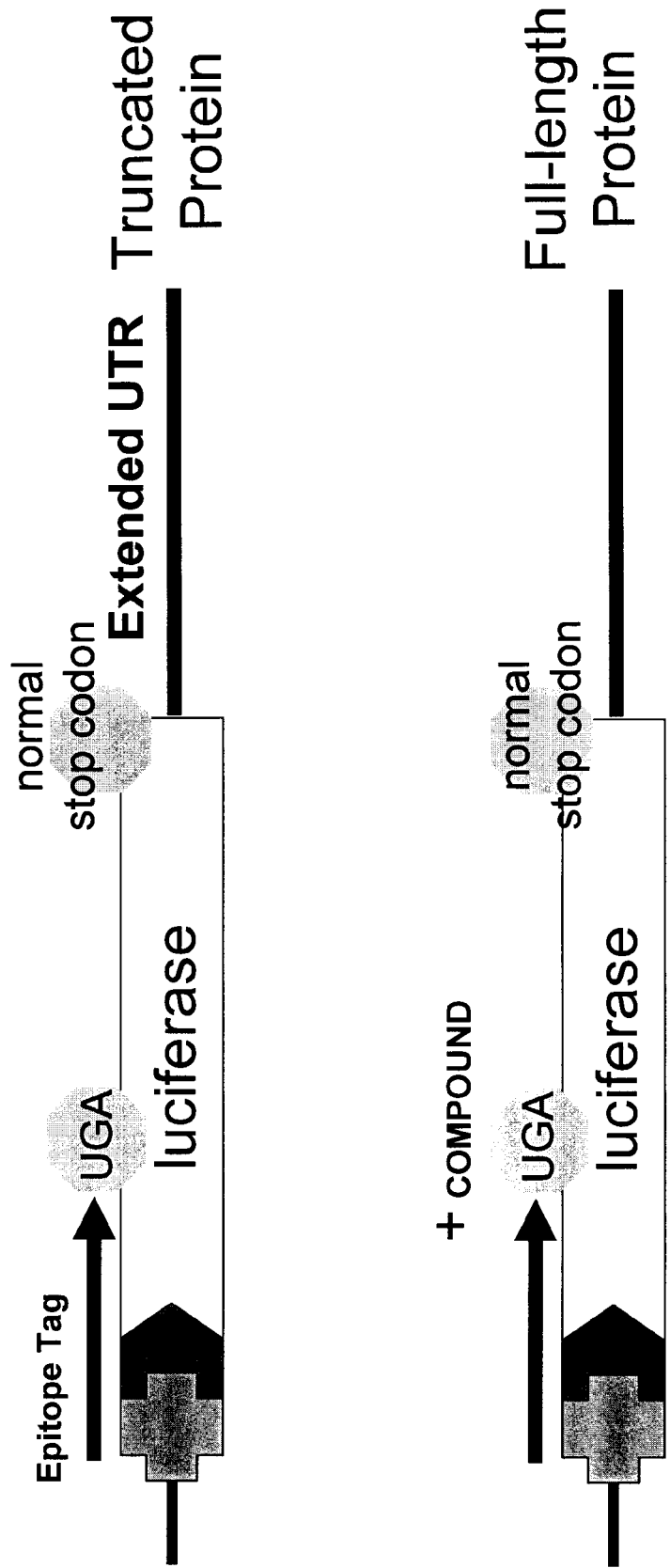

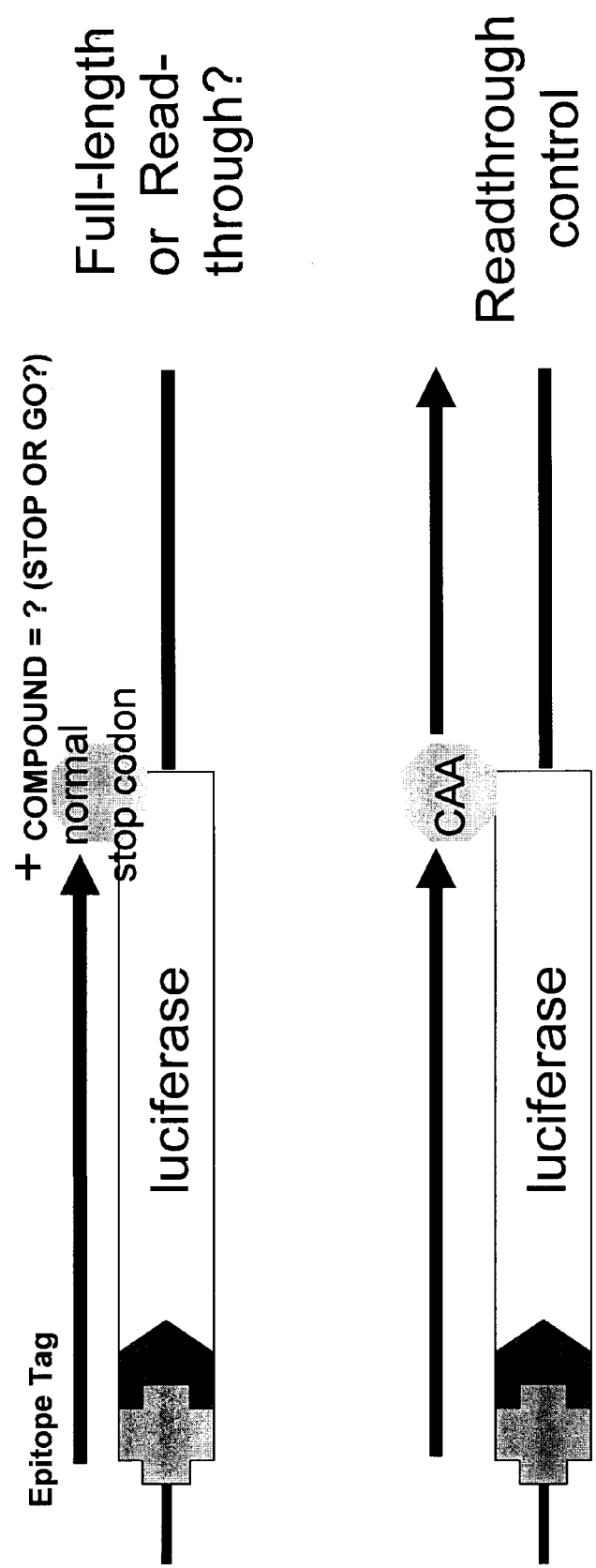

COMPOUNDS FOR NONSENSE SUPPRESSION, AND METHODS FOR THEIR USE

CROSS-REFERENCE TO RELATED APPLICATIONS

This application is a national phase application under 35 U.S.C. §371 of International Application No. PCT/US2005/036764, filed Oct. 13, 2005, the disclosure of which is hereby incorporated by reference in its entirety, and which claims priority to and the benefit under 35 U.S.C. §119 of U.S. Provisional Application No. 60/617,634, filed Oct. 13, 2004, U.S. Provisional Application No. 60/617,655, filed Oct. 13, 2004, U.S. Provisional Application No. 60/617,633, filed Oct. 13, 2004, and U.S. Provisional Application No. 60/617,670, filed Oct. 13, 2004, all of which are herein incorporated by reference in their entireties. International Application No. PCT/US2005/036764 also claims priority to and the benefit under 35 U.S.C. §119 of U.S. Provisional Application No. 60/617,653, filed Oct. 13, 2004, and U.S. Provisional Application No. 60/624,170, filed Nov. 3, 2004. U.S. Provisional Application No. 60/624,170, filed Nov. 3, 2004, is herein incorporated by reference in its entirety. The present application also incorporates by reference herein in their entireties International Application No. PCT/US2005/036673, filed on Oct. 13, 2005, International Application No. PCT/US2005/036761, filed Oct. 13, 2005, International Application No. PCT/US2005/036762, filed Oct. 13, 2005, and International Application No. PCT/US2005/037052, filed Oct. 13, 2005.

FIELD OF THE INVENTION

The present invention relates to methods, compounds, and compositions for treating or preventing diseases associated with nonsense mutations in an mRNA by administering the compounds or compositions of the present invention. More particularly, the present invention relates to methods, compounds, and compositions for suppressing premature translation termination associated with a nonsense mutation in an mRNA.

BACKGROUND OF THE INVENTION

Gene expression in cells depends upon the sequential processes of transcription and translation. Together, these processes produce a protein from the nucleotide sequence of its corresponding gene.

Transcription involves the synthesis of mRNA from DNA by RNA polymerase. Transcription begins at a promoter region of the gene and continues until termination is induced, such as by the formation of a stem-loop structure in the nascent RNA or the binding of the rho gene product.

Protein is then produced from mRNA by the process of translation, occurring on the ribosome with the aid of tRNA, tRNA synthetases and various other protein and RNA species. Translation comprises the three phases of initiation, elongation and termination. Translation is initiated by the formation of an initiation complex consisting of protein factors, mRNA, tRNA, cofactors and the ribosomal subunits that recognize signals on the mRNA that direct the translation machinery to begin translation on the mRNA. Once the initiation complex is formed, growth of the polypeptide chain occurs by the repetitive addition of amino acids by the peptidyl transferase activity of the ribosome as well as tRNA and tRNA synthetases. The presence of one of the three termination codons (UAA, UAG, UGA) in the A site of the ribosome signals the polypeptide chain release factors (RFs) to bind and recognize the termination signal. Subsequently, the ester bond between the 3' nucleotide of the tRNA located in the ribosome's P site and the nascent polypeptide chain is hydrolyzed, the completed polypeptide chain is released, and the ribosome subunits are recycled for another round of translation.

Mutations of the DNA sequence in which the number of bases is altered are categorized as insertion or deletion mutations (e.g., frameshift mutations) and can result in major disruptions of the genome. Mutations of the DNA that change one base into another and result in an amino acid substitution are labeled missense mutations. Base substitutions are subdivided into the classes of transitions (one purine to another purine, or one pyrimidine to another pyrimidine) and transversions (a purine to a pyrimidine, or a pyrimidine to a purine).

Transition and transversion mutations can result in a nonsense mutation changing an amino acid codon into one of the three stop codons. These premature stop codons can produce aberrant proteins in cells as a result of premature translation termination. A nonsense mutation in an essential gene can be lethal and can also result in a number of human diseases, such as, cancers, lysosomal storage disorders, the muscular dystrophies, cystic fibrosis and hemophilia, to name a few.

The human p53 gene is the most commonly mutated gene in human cancer (Zambetti, G. P. and Levine, A., *FASEB* 7:855-865 (1993)). Found in both genetic and spontaneous cancers, over 50 different types of human cancers contain p53 mutations and mutations of this gene occur in 50-55% of all human cancers (Hollstein, M., et al., *Nucleic Acids Res.* 22:3551-55 (1994); International Agency for Research on Cancer (IARC) database). Approximately 70% of colorectal cancer, 50% of lung cancer and 40% of breast cancers contain mutant p53 (Koshland, D., *Science* 262:1953 (1993)). Aberrant forms of p53 are associated with poor prognosis, more aggressive tumors, metastasis, and lower 5 year survival rates (Id.). p53's role in the induction of cell growth arrest and/or apoptosis upon DNA damage is believed to be essential for the destruction of mutated cells that would have otherwise gained a growth advantage. In addition, p53 sensitizes rapidly dividing cells to apoptotic signals. Of greater than 15,000 reported mutations in the p53 gene, approximately 7% are nonsense mutations. Accordingly, there is a need for a safe and effective treatment directed to p53 nonsense mutations.

In bacterial and eukaryotic strains with nonsense mutations, suppression of the nonsense mutation can arise as a result of a mutation in one of the tRNA molecules so that the mutant tRNA can recognize the nonsense codon, as a result of mutations in proteins that are involved in the translation process, as a result of mutations in the ribosome (either the ribosomal RNA or ribosomal proteins), or by the addition of compounds known to alter the translation process (for example, cycloheximide or the aminoglycoside antibiotics). The result is that an amino acid will be incorporated into the polypeptide chain, at the site of the nonsense mutation, and translation will not prematurely terminate at the nonsense codon. The inserted amino acid will not necessarily be identical to the original amino acid of the wild-type protein, however, many amino acid substitutions do not have a gross effect on protein structure or function. Thus, a protein produced by the suppression of a nonsense mutation would be likely to possess activity close to that of the wild-type protein. This scenario provides an opportunity to treat diseases associated with nonsense mutations by avoiding premature termination of translation through suppression of the nonsense mutation.

The ability of aminoglycoside antibiotics to promote readthrough of eukaryotic stop codons has attracted interest in these drugs as potential therapeutic agents in human diseases caused by nonsense mutations. One disease for which such a therapeutic strategy may be viable is classical late infantile neuronal ceroid lipofuscinosis (LINCL), a fatal childhood neurodegenerative disease with currently no effective treatment. Premature stop codon mutations in the gene CLN2 encoding the lysosomal tripeptidyl-peptidase 1 (TPP-I) are associated with disease in approximately half of children diagnosed with LINCL. The ability of the aminoglycoside gentamicin to restore TPP-I activity in LINCL cell lines has been examined. In one patient-derived cell line that was compound heterozygous for a commonly seen nonsense mutation (Arg208Stop) and a different rare nonsense mutation, approximately 7% of normal levels of TPP-I were maximally restored with gentamicin treatment. These results suggest that pharmacological suppression of nonsense mutations by aminoglycosides or functionally similar pharmaceuticals may have therapeutic potential in LINCL (Sleat et. al., *Eur. J. Ped. Neurol.* 5:Suppl A 57-62 (2001)).

In cultured cells having premature stop codons in the Cystic Fibrosis Transmembrane Conductance Regulator (CFTR) gene, treatment with aminoglycosides led to the production of full-length CFTR (Bedwell et. al., *Nat. Med.* 3:1280-1284 (1997); Howard et. al. *Nat. Med.* 2: 467-469 (1996)). In mouse models for Duchenne muscular dystrophy, gentamicin sulfate was observed to suppress translational termination at premature stop codons resulting in full-length dystrophin (Barton-Davis et. al., *J. Clin. Invest.* 104:375-381 (1999)). A small increase in the amount of full-length dystrophin provided protection against contraction-induced damage in the mdx mice. The amino acid inserted at the site of the nonsense codon was not determined in these studies.

Accordingly, small molecule therapeutics or prophylactics that suppress premature translation termination by mediating the misreading of the nonsense codon would be useful for the treatment of a number of diseases. The discovery of small molecule drugs, particularly orally bioavailable drugs, can lead to the introduction of a broad spectrum of selective therapeutics or prophylactics to the public which can be used against disease caused by nonsense mutations is just beginning.

Clitocine (6-Amino-5-nitro-4-(β-D-ribo-furanosylamino) pyrimidine) is a naturally occurring exocyclic amino nucleoside that was first isolated from the mushroom *Clitocybe inversa* (Kubo et al., *Tet. Lett.* 27: 4277 (1986)). The total synthesis of clitocine has also been reported. (Moss et al., *J. Med. Chem.* 31:786-790 (1988) and Kamikawa et al., *J. Chem. Soc. Chem. Commun.* 195 (1988)). Clitocine has been reported to possess insecticidal activity and cytostatic activity against leukemia cell lines (Kubo et al., *Tet. Lett.* 27: 4277 (1986) and Moss et al., *J. Med. Chem.* 31:786-790 (1988)). However, the use of clitocine as a therapeutic for diseases associated with a nonsense mutation has not been disclosed until now. Nor has anyone reported the development of an analogue or derivative of clitocine that has utility as a therapeutic for cancer or a disease associated with a nonsense mutation.

Thus, there remains a need to develop characterize and optimize lead molecules for the development of novel drugs for treating or preventing diseases associated with nonsense mutations of mRNA. Accordingly, it is an object of the present invention to provide such compounds.

All documents referred to herein are incorporated by reference into the present application as though fully set forth herein.

SUMMARY OF THE INVENTION

In accordance with the present invention, compounds that suppress premature translation termination associated with a nonsense mutation in mRNA have been identified, and methods for their use provided.

In one aspect of the invention, compounds of Formula (1) are provided which are useful for suppressing premature translation termination associated with a nonsense mutation in mRNA, and for treating diseases associated with nonsense mutations in mRNA:

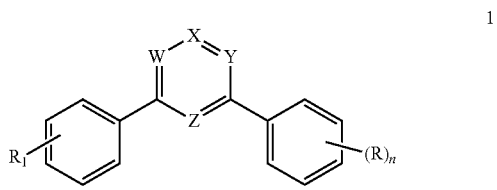

wherein:

W, X, Y and Z are independently selected from N or C—$R_a$, where $R_a$ is hydrogen or a $C_1$-$C_4$ alkyl group, wherein at least one of W, X, Y, or Z is N;

n is 0, 1, 2, or 3;

$R_1$ is a cyano group; a carbamoyl which is optionally substituted with one or two $C_1$-$C_4$ alkyl groups; or a carbonyl group which is substituted with a hydroxy, a $C_1$-$C_4$ alkyl, or a $C_1$-$C_4$ alkoxy group;

R is a hydroxy group; a halogen; a $C_1$-$C_4$ alkyl which is optionally substituted with one or more independently selected halogen or hydroxy groups; a $C_1$-$C_4$ alkoxy which is optionally substituted with one or more independently selected halogen or phenyl groups; a $C_4$-$C_8$ cycloalkyl which is optionally substituted with one or more independently selected $C_1$-$C_4$ alkyl groups; an —$R_b$ group; an —O—$R_b$ group; a five to six-membered heterocycle which is optionally substituted with one or more independently selected $C_1$-$C_4$ alkyl, oxo, or —$R_b$ groups; a nine to ten membered heterocycle having two ring structures; a carbonyl which is substituted with a hydroxy, a $C_1$-$C_4$ alkyl, or a $C_1$-$C_4$ alkoxy group; a carbamoyl which is optionally substituted with one or two $C_1$-$C_4$ alkyl groups; a nitro group; a cyano group; a thio which is optionally substituted with a hydroxy, a $C_1$-$C_4$ alkyl, or —$R_b$ group; a sulfonyl which is optionally substituted with a hydroxy, a $C_1$-$C_4$ alkyl, or —$R_b$ group; an amino which is optionally substituted with one or two independently selected $C_1$-$C_4$ alkyl, sulfonyl, or carbonyl groups, wherein the aminosulfonyl group is optionally substituted with a hydroxy, a $C_1$-$C_4$ alkyl, or —$R_b$ group and wherein the aminocarbonyl group is optionally substituted with a $C_1$-$C_4$ alkyl, a $C_1$-$C_4$ haloalkyl, a benzoxy, or an amino group which is optionally substituted with an —$R_b$ group; or two R groups together with the phenyl ring to which they are attached form a benzo[1,3]dioxole or a 2,3-dihydro-benzo[1,4]dioxinyl group, wherein —$R_b$ is a $C_6$-$C_8$ aryl which is optionally substituted with one or more of the following: a hydroxy, a halogen, a $C_1$-$C_4$ alkyl group, a $C_1$-$C_4$ haloalkyl group, a $C_1$-$C_4$ alkoxy group, or an amino group which is optionally substituted with one or more $C_1$-$C_4$ alkyl groups;

or a pharmaceutically acceptable salt, hydrate, solvate, clathrate, polymorph, racemate or stereoisomer of said compound of Formula 1.

In another aspect of the invention, methods are provided for the suppression of premature translation termination associated with a nonsense mutation, and for the prevention or treatment of diseases associated with nonsense mutations of mRNA. Such diseases include, but are not limited to, genetic diseases caused by premature translation termination associated with a nonsense mutation, such as a CNS disease, an inflammatory disease, a neurodegenerative disease, an autoimmune disease, a cardiovascular disease, or a pulmonary disease; more preferably the disease is cancer (or other proliferative diseases), amyloidosis, Alzheimer's disease, atherosclerosis, giantism, dwarfism, hypothyroidism, hyperthyroidism, cystic fibrosis, aging, obesity, Parkinson's disease, Niemann Pick's disease, familial hypercholesterolemia, retinitis pigmentosa, Marfan syndrome, lysosomal storage disorders, the muscular dystrophies, cystic fibrosis, hemophilia, or classical late infantile neuronal ceroid lipofuscinosis (LINCL).

In one embodiment, the invention is directed to methods for suppressing premature translation termination associated with a nonsense mutation in mRNA comprising administering a nonsense-suppressing amount of at least one compound of the invention to a subject in need thereof.

In yet another embodiment, methods for treating cancer, lysosomal storage disorders, a muscular dystrophy, cystic fibrosis, hemophilia, or classical late infantile neuronal ceroid lipofuscinosis are provided comprising administering a therapeutically effective amount of at least one compound of the invention to a subject in need thereof.

These and other aspects of the invention will be more clearly understood with reference to the following preferred embodiments and detailed description.

CERTAIN EMBODIMENTS

1. A method of treating or preventing a disease resulting from a somatic mutation comprising administering to a patient in need thereof an effective amount of a compound of Formula 1:

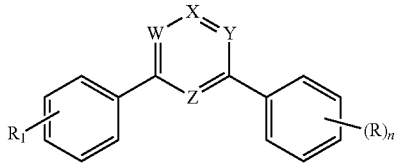

wherein:
W, X, Y and Z are independently selected from N or C—$R_a$, where $R_a$ is hydrogen or a $C_1$-$C_4$ alkyl group, wherein at least one of W, X, Y, or Z is N;
n is 0, 1, 2, or 3;
$R_1$ is a cyano group; a carbamoyl which is optionally substituted with one or two $C_1$-$C_4$ alkyl groups; or a carbonyl group which is substituted with a hydroxy, a $C_1$-$C_4$ alkyl, or a $C_1$-$C_4$ alkoxy group;
R is independently selected from a hydroxy group; a halogen; a $C_1$-$C_4$ alkyl which is optionally substituted with one or more independently selected halogen or hydroxy groups; a $C_1$-$C_4$ alkoxy which is optionally substituted with one or more independently selected halogen or phenyl groups; a $C_4$-$C_8$ cycloalkyl which is optionally substituted with one or more independently selected $C_1$-$C_4$ alkyl groups; an —$R_b$ group; a —O—$R_b$ group; a five to six-membered heterocycle which is optionally substituted with one or more independently selected $C_1$-$C_4$ alkyl, oxo, or —$R_b$ groups; a nine to ten membered heterocycle having two ring structures; a carbonyl which is substituted with a hydroxy, a $C_1$-$C_4$ alkyl, or a $C_1$-$C_4$ alkoxy group; a carbamoyl which is optionally substituted with one or two $C_1$-$C_4$ alkyl groups; a nitro group; a cyano group; a thio which is optionally substituted with a hydroxy, a $C_1$-$C_4$ alkyl, or —$R_b$ group; a sulfonyl which is optionally substituted with a hydroxy, a $C_1$-$C_4$ alkyl, or —$R_b$ group; an amino which is optionally substituted with one or two independently selected $C_1$-$C_4$ alkyl, sulfonyl, or carbonyl groups, wherein the aminosulfonyl group is optionally substituted with a hydroxy, a $C_1$-$C_4$ alkyl, or —$R_b$ group, and wherein the aminocarbonyl group is optionally substituted with a $C_1$-$C_4$ alkyl, a $C_1$-$C_4$ haloalkyl, a benzoxy, or an amino group which is optionally substituted with an —$R_b$ group; or two R groups together with the phenyl ring to which they are attached form a benzo[1,3]dioxole or a 2,3-dihydro-benzo[1,4]dioxinyl group; wherein —$R_b$ is a $C_6$-$C_8$ aryl which is optionally substituted with one or more of the following: a hydroxy, a halogen, a $C_1$-$C_4$ alkyl group, a $C_1$-$C_4$ haloalkyl group, a $C_1$-$C_4$ alkoxy group, or an amino group which is optionally substituted with one or more $C_1$-$C_4$ alkyl groups;
or a pharmaceutically acceptable salt, hydrate, solvate, clathrate, polymorph, racemate or stereoisomer of said compound of Formula 1.

2. The method of embodiment 1, wherein the compound of Formula 1, or a pharmaceutically acceptable salt, hydrate, solvate, clathrate polymorph, racemate or stereoisomer thereof, is administered as a composition comprising the compound and a pharmaceutically acceptable carrier or diluent.

3. The method of embodiment 1, wherein the administration is intravenous.

4. The method of embodiment 1, wherein $R_1$ is in a meta or para position.

5. The method of embodiment 1, wherein W, Y, and Z are each N, and X is C—$R_a$ (Formula 1-A):

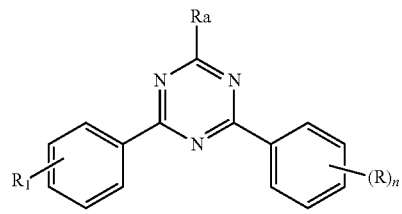

6. The method of embodiment 5, wherein $R_1$ is a carboxy group, and is located in a meta or para position.

7. The method of embodiment 5, wherein $R_a$ is hydrogen.

8. The method of embodiment 5, wherein n is 1 or 2.

9. The method of embodiment 5, wherein R is independently selected from a halogen, a $C_1$-$C_4$ alkyl, a $C_1$-$C_4$ haloalkyl, or a $C_1$-$C_4$ alkoxy.

10. The method of embodiment 5, wherein R is located in a meta and/or para position.

11. The method of embodiment 1, wherein Y and Z are both N, and W and X are both C—$R_a$ (Formula 1-B):

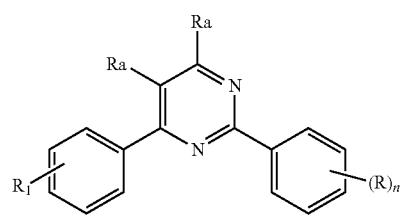

12. The method of embodiment 11, wherein $R_1$ is a carboxy group, and is located in a meta or para position.
13. The method of embodiment 11, wherein $R_a$ is hydrogen.
14. The method of embodiment 11, wherein n is 1 or 2.
15. The method of embodiment 11, wherein R is independently selected from a halogen, a $C_1$-$C_4$ alkyl, a $C_1$-$C_4$ haloalkyl, a $C_1$-$C_4$ alkoxy, a $C_1$-$C_4$ haloalkoxy, amino, or pyrrolyl group.
16. The method of embodiment 11, wherein R is located in a meta and/or para position.
17. The method of embodiment 1, wherein W and Y are both N, and X and Z are both C—$R_a$ (Formula 1-C):

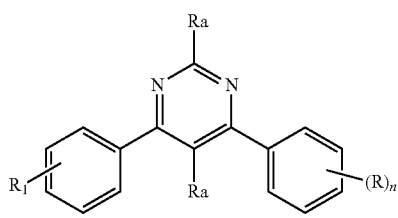

18. The method of embodiment 17, wherein $R_1$ is a carboxy group, and is located in a meta or para position.
19. The method of embodiment 17, wherein $R_a$ is hydrogen.
20. The method of embodiment 17, wherein n is 1 or 2.
21. The method of embodiment 17, wherein R is independently selected from a $C_1$-$C_4$ alkyl.
22. The method of embodiment 17, wherein R is located in a meta and/or para position.
23. The method of embodiment 1, wherein W and Z are both N, and X and Y are both C—$R_a$ (Formula 1-D):

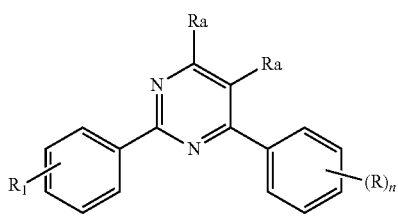

24. The method of embodiment 23, wherein $R_1$ is a carboxy group, and is located in a meta or para position.
25. The method of embodiment 23, wherein $R_a$ is independently selected from hydrogen or methyl.
26. The method of embodiment 23, wherein n is 1 or 2.
27. The method of embodiment 23, wherein R is located in a meta and/or para position.
28. The method of embodiment 1, wherein W is N, and X, Y, and Z are each C—$R_a$ (Formula 1-E):

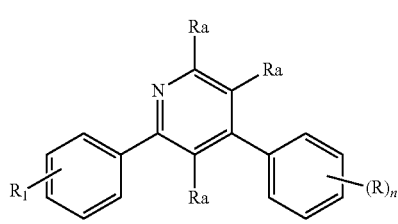

29. The method of embodiment 28, wherein $R_1$ is a carboxy group, and is located in a meta or para position.
30. The method of embodiment 28, wherein $R_a$ is hydrogen.
31. The method of embodiment 28, wherein n is 1 or 2.
32. The method of embodiment 28, wherein R is independently selected from a $C_1$-$C_4$ alkyl.
33. The method of embodiment 28, wherein R is located in a meta and/or para position.
34. The method of embodiment 1, wherein X is N, and W, Y, and Z are each C—$R_a$ (Formula 1-F):

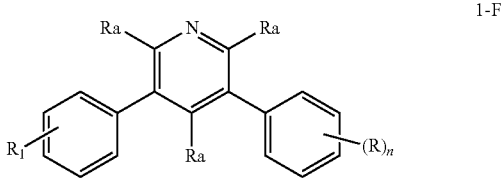

35. The method of embodiment 34, wherein $R_1$ is a carboxy group, and is located in a meta or para position.
36. The method of embodiment 34, wherein $R_a$ is hydrogen.
37. The method of embodiment 34, wherein n is 1 or 2.
38. The method of embodiment 34, wherein R is independently selected from a $C_1$-$C_4$ alkyl.
39. The method of embodiment 34, wherein R is located in a meta and/or para position.
40. The method of embodiment 1, wherein Y is N, and W, X, and Z are each C—$R_a$ (Formula 1-G):

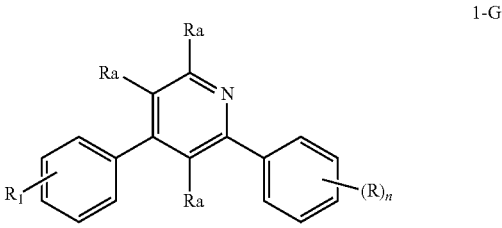

41. The method of embodiment 40, wherein $R_1$ is a carboxy group, and is located in a meta or para position.
42. The method of embodiment 40, wherein $R_a$ is hydrogen.
43. The method of embodiment 40, wherein n is 1 or 2.
44. The method of embodiment 40, wherein R is independently selected from a $C_1$-$C_4$ alkyl.
45. The method of embodiment 40, wherein R is located in a meta and/or para position.
46. The method of embodiment 1, wherein Z is N, and W, X, and Y are each C—$R_a$ (Formula 1-H):

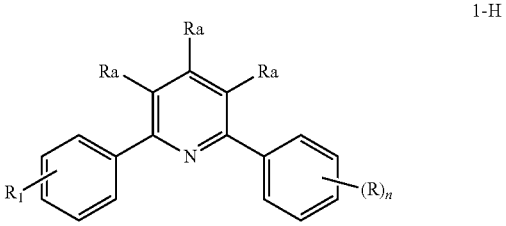

47. The method of embodiment 46, wherein $R_1$ is a carboxy group, and is located in a meta or para position.
48. The method of embodiment 46, wherein $R_a$ is hydrogen.
49. The method of embodiment 46, wherein n is 1 or 2.

50. The method of embodiment 46, wherein R is independently selected from a $C_1$-$C_4$ alkyl.

51. The method of embodiment 46, wherein R is located in a meta and/or para position.

52. A method of treating or preventing an autoimmune disease, a blood disease, a collagen disease, diabetes, a neurodegenerative disease, a cardiovascular disease, a pulmonary disease, an inflammatory disease or a central nervous system disease comprising administering to a patient in need thereof an effective amount of a compound of Formula 1, or a pharmaceutically acceptable salt, hydrate, solvate, clathrate, racemate or stereoisomer thereof.

53. The method of embodiment 52, wherein the administration is intravenous.

54. The method of embodiment 52, wherein the autoimmune disease is rheumatoid arthritis or graft versus host disease.

55. The method of embodiment 52, wherein the inflammatory disease is arthritis.

56. The method of embodiment 52, wherein the central nervous system disease is multiple sclerosis, muscular dystrophy, Duchenne muscular dystrophy, Alzheimer's disease, a neurodegenerative disease or Parkinson's disease.

57. The method of embodiment 52, wherein the blood disorder is hemophilia, Von Willebrand disease, ataxia-telangiectasia, β-thalassemia or kidney stones.

58. The method of embodiment 52, wherein the collagen disease is osteogenesis imperfecta or cirrhosis.

59. A method of treating or preventing familial polycythemia, immunodeficiency, kidney disease, cystic fibrosis, familial hypercholesterolemia, retinitis pigmentosa, amyloidosis, hemophilia, Alzheimer's disease, Tay Sachs disease, Niemann Pick disease, Parkinson's disease, atherosclerosis, giantism, dwarfism, hyperthyroidism, aging, obesity, Duchenne muscular dystrophy or Marfan syndrome comprising administering to a patient in need thereof an effective amount of a compound of Formula 1, or a pharmaceutically acceptable salt, hydrate, solvate, clathrate, racemate or stereoisomer thereof.

60. The method of embodiment 59, wherein the administration is intravenous.

61. A method of treating or preventing cancer in a human comprising administering to a human in need thereof an effective amount of a compound of Formula 1, or a pharmaceutically acceptable salt, hydrate, solvate, clathrate, racemate or stereoisomer thereof.

62. The method of embodiment 61, wherein the administration is intravenous.

63. The method of embodiment 61, wherein the cancer is of the head and neck, eye, skin, mouth, throat, esophagus, chest, bone, blood, lung, colon, sigmoid, rectum, stomach, prostate, breast, ovaries, kidney, liver, pancreas, brain, intestine, heart or adrenals.

64. The method of embodiment 61, wherein the compound, or a pharmaceutically acceptable salt, hydrate, solvate, clathrate or stereoisomer thereof, comprises a pharmaceutically acceptable carrier or diluent.

65. The method of embodiment 61, wherein the cancer is a solid tumor.

66. The method of embodiment 61, wherein the cancer is sarcoma, carcinoma, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, Kaposi's sarcoma, pinealoma, hemangioblastoma, acoustic neuroma, oligodendroglioma, menangioma, melanoma, neuroblastoma, retinoblastoma, a blood-born tumor or multiple myeloma.

67. The method of embodiment 61, wherein the cancer is acute lymphoblastic leukemia, acute lymphoblastic B-cell leukemia, acute lymphoblastic T-cell leukemia, acute myeloblastic leukemia, acute promyelocytic leukemia, acute monoblastic leukemia, acute erythroleukemic leukemia, acute megakaryoblastic leukemia, acute myelomonocytic leukemia, acute nonlymphocytic leukemia, acute undifferentiated leukemia, chronic myelocytic leukemia, chronic lymphocytic leukemia, hairy cell leukemia, or multiple myeloma.

68. A method of treating or preventing a disease associated with a mutation of the p53 gene comprising administering to a patient in need thereof an effective amount of a compound of Formula 1, or a pharmaceutically acceptable salt, hydrate, solvate, clathrate, racemate or stereoisomer thereof.

69. The method of embodiment 68, wherein the administration is intravenous.

70. The method of embodiment 68, wherein the disease is sarcoma, carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, Kaposi's sarcoma, pinealoma, hemangioblastoma, acoustic neuroma, oligodendroglioma, menangioma, melanoma, neuroblastoma retinoblastoma a blood-born tumor or multiple myeloma.

71. A method of inhibiting the growth of a cancer cell comprising contacting the cancer cell with an effective amount of a compound of Formula 1, or a pharmaceutically acceptable salt, hydrate, solvate, clathrate, racemate or stereoisomer thereof.

72. A method for selectively producing a protein in a mammal comprising, transcribing a gene containing a nonsense mutation in the mammal; and providing an effective amount of a compound of Formula 1 to said mammal, wherein said protein is produced by said mammal.

BRIEF DESCRIPTION OF THE DRAWINGS

FIG. 1 provides schematic representations of constructs for luciferase based assays to evaluate the suppression of a nonsense mutation.

FIG. 2 provides schematic representations of the luciferase constructs engineered to harbor one or more epitope tags in the N-terminus of the luciferase protein.

FIG. 3 provides schematic representations of constructs for luciferase based assays to evaluate readthrough efficiency.

DETAILED DESCRIPTION OF THE INVENTION

Premature translation termination can produce aberrant proteins which can be lethal or can cause a number of diseases, including as non-limiting examples, cancers, lysosomal storage disorders, the muscular dystrophies, cystic fibrosis and hemophilia. In accordance with the present invention, compounds that suppress nonsense mutations have been identified, and methods for their use provided.

A. Compounds of the Invention

In one aspect of the invention, compounds of the invention are provided which are useful in suppression of a nonsense mutation. In certain embodiments, the compounds of the invention specifically suppresses a nonsense mutation, while in other embodiments, the compounds of the invention suppress a nonsense mutation as well as treat a disease, including as non-limiting examples, cancers, lysosomal storage disorders, the muscular dystrophies, cystic fibrosis and hemophilia.

Preferred compounds of the present invention useful in the suppression of a nonsense mutation include those of Formula (1) as shown below.

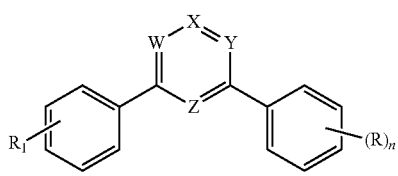

1 wherein:

W, X, Y and Z are independently selected from N or C—$R_a$, where $R_a$ is hydrogen or a $C_1$-$C_4$ alkyl group, wherein at least one of W, X, Y, or Z is N;

n is 0, 1, 2, or 3;

$R_1$ is a cyano group; a carbamoyl which is optionally substituted with one or two $C_1$-$C_4$ alkyl groups; or a carbonyl group which is substituted with a hydroxy, a $C_1$-$C_4$ alkyl, or a $C_1$-$C_4$ alkoxy group;

R is a hydroxy group; a halogen; a $C_1$-$C_4$ alkyl which is optionally substituted with one or more independently selected halogen or hydroxy groups; a $C_1$-$C_4$ alkoxy which is optionally substituted with one or more independently selected halogen or phenyl groups; a $C_4$-$C_8$ cycloalkyl which is optionally substituted with one or more independently selected $C_1$-$C_4$ alkyl groups; an —$R_b$ group; an —O—$R_b$ group; a five to six-membered heterocycle which is optionally substituted with one or more independently selected $C_1$-$C_4$ alkyl, oxo, or —$R_b$ groups; a nine to ten membered heterocycle having two ring structures; a carbonyl which is substituted with a hydroxy, a $C_1$-$C_4$ alkyl, or a $C_1$-$C_4$ alkoxy group; a carbamoyl which is optionally substituted with one or two $C_1$-$C_4$ alkyl groups; a nitro group; a cyano group; a thio which is optionally substituted with a hydroxy, a $C_1$-$C_4$ alkyl, or —$R_b$ group; a sulfonyl which is optionally substituted with a hydroxy, a $C_1$-$C_4$ alkyl, or —$R_b$ group; an amino which is optionally substituted with one or two independently selected $C_1$-$C_4$ alkyl, sulfonyl, or carbonyl groups, wherein the aminosulfonyl group is optionally substituted with a hydroxy, a $C_1$-$C_4$ alkyl, or —$R_b$ group, and wherein the aminocarbonyl group is optionally substituted with a $C_1$-$C_4$ alkyl, a $C_1$-$C_4$ haloalkyl, a benzoxy, or an amino group which is optionally substituted with an —$R_b$ group; or two R groups together with the phenyl ring to which they are attached form a benzo[1,3]dioxole or a 2,3-dihydro-benzo[1,4]dioxinyl group, wherein —$R_b$ is a $C_6$-$C_8$ aryl which is optionally substituted with one or more of the following: a hydroxy, a halogen, a $C_1$-$C_4$ alkyl group, a $C_1$-$C_4$ haloalkyl group, a $C_1$-$C_4$ alkoxy group, or an amino group which is optionally substituted with one or more $C_1$-$C_4$ alkyl group or a pharmaceutically acceptable salt, hydrate, solvate, clathrate, polymorph, racemate or stereoisomer of said compound of Formula 1.

In another preferred embodiment of Formula 1, preferred compounds of the present invention useful in the suppression of a nonsense mutation include those of Formula (1), wherein n is 0, 1 or 2;

$R_1$ is a cyano group; a carbamoyl; or a carbonyl group which is substituted with a hydroxy;

R is independently selected from a hydroxy group; a halogen; a $C_1$-$C_4$ alkyl which is optionally substituted with one or more independently selected halogen; a $C_1$-$C_4$ alkoxy which is optionally substituted with one or more independently selected halogen; an —$R_b$ group; a five to six-membered heterocycle; an amino which is optionally substituted with one or two independently selected $C_1$-$C_4$ alkyl; or two R groups together with the phenyl ring to which they are attached form a benzo[1,3]dioxole or a 2,3-dihydro-benzo[1,4]dioxinyl group; wherein —$R_b$ is a $C_6$-$C_8$ aryl;

or a pharmaceutically acceptable salt, hydrate, solvate, clathrate, polymorph, racemate or stereoisomer of said compound of Formula 1.

As recognized by one of skill in the art, certain compounds of the invention may include at least one chiral center, and as such may exist as racemic mixtures or as enantiomerically pure compositions. As used herein, "enantiomerically pure" refers to compositions consisting substantially of a single isomer, preferably consisting of 90%, 92%, 95%, 98%, 99%, or 100% of a single isomer.

As used herein, the term "alkyl" generally refers to saturated hydrocarbyl radicals of straight, branched or cyclic configuration including methyl, ethyl, n-propyl, isopropyl, n-butyl, isobutyl, sec-butyl, tert-butyl, n-pentyl, n-hexyl, cyclohexyl, n-heptyl, octyl, n-octyl, and the like. In some embodiments, alkyl substituents may be $C_1$ to $C_8$, $C_1$ to $C_6$, or $C_1$ to $C_4$ alkyl groups. In certain embodiments, the alkyl group may be optionally substituted with one or more halogen or alkoxy groups. For instance, the alkyl group may be a haloalkyl, including monohaloalkyl, dihaloalkyl, and trihaloalkyl.

As used herein, "alkylene" generally refers to linear, branched or cyclic alkene radicals having one or more carbon-carbon double bonds, such as $C_2$ to $C_6$ alkylene groups including 3-propenyl.

As used herein, "aryl" refers to a carbocyclic aromatic ring structure. Included in the scope of aryl groups are aromatic rings having from five to twenty carbon atoms. Aryl ring structures include compounds having one or more ring structures, such as mono-, bi-, or tricyclic compounds. Examples of aryl groups that include phenyl, tolyl, anthracenyl, fluorenyl, indenyl, azulenyl, phenanthrenyl (i.e., phenanthrene), and napthyl (i.e., napthalene) ring structures. In certain embodiments, the aryl group may be optionally substituted.

As used herein, "heterocycle" refers to cyclic ring structures in which one or more atoms in the ring, the heteroatom (s), is an element other than carbon. Heteroatoms are typically O, N, or S atoms. Included within the scope of heterocycle, and independently selectable, are O, N, and S heterocycle ring structures. The ring structure may include compounds having one or more ring structures, such as mono-, bi-, or tricyclic compounds, and may be aromatic, i.e., the ring structure may be a heteroaryl. Example of heterocyclo groups include morpholinyl, pyrrolidinonyl, pyrrolidinyl, piperidinyl, piperazinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl or tetrahydrothiopyranyl and the like. In certain embodiments, the heterocycle may optionally be substituted.

As used herein, "heteroaryl" refers to cyclic aromatic ring structures in which one or more atoms in the ring, the heteroatom(s), is an element other than carbon. Heteroatoms are typically O, N, or S atoms. Included within the scope of heteroaryl, and independently selectable, are O, N, and S heteroaryl ring structures. The ring structure may include compounds having one or more ring structures, such as mono-, bi-, or tricyclic compounds. In some embodiments, the heteroaryl groups may be selected from heteroaryl groups that contain two or more heteroatoms, three or more heteroatoms, or four or more heteroatoms. Heteroaryl ring structures may be selected from those that contain five or more atoms, six or more atoms, or eight or more atoms. In a preferred embodiment, the heteroaryl including five to ten atoms. Examples of heteroaryl ring structures include: acridine, benzimidazole, benzoxazole, benzodioxole, benzofuran, 1,3-diazine, 1,2-diazine, 1,2-diazole, 1,4-diazanaphthalene, furan, furazan, imidazole, indole, isoxazole, isoquinoline, isothiazole, oxazole, purine, pyridazine, pyrazole, pyridine, pyrazine, pyrimidine, pyrrole, quinoline, quinoxaline, thiazole, thiophene, 1,3,5-triazine, 1,2,4-triazine, 1,2,3-triazine, tetrazole and quinazoline.

As used herein, "alkoxy" generally refers to a group with the structure —O—R. In certain embodiments, R may be an alkyl group, such as a $C_1$ to $C_8$ alkyl group, $C_1$ to $C_6$ alkyl group, or $C_1$ to $C_4$ alkyl group. In certain embodiments, the R group of the alkoxy may optionally be substituted with at least one halogen. For example, the R group of the alkoxy may be a haloalkyl, i.e., haloalkoxy.

Halogen substituents may be independently selected from the halogens such as fluorine, chlorine, bromine, iodine, and astatine.

For the purposes of this invention, where one or more functionalities or substituents are incorporated into a compound of the invention, including preferred embodiments, each functionality or substituent appearing at any location within the disclosed compounds may be independently selected, and as appropriate, independently substituted. Further, where a more generic substituent is set forth for any position in the molecules of the present invention, it is understood that the generic substituent may be replaced with more specific substituents, and the resulting molecules are within the scope of the molecules of the present invention.

With reference to Formula 1, in an embodiment, R is preferably in a meta and/or para position and is preferably a halogen, a $C_1$-$C_4$ alkyl, a $C_1$-$C_4$ haloalkyl, a $C_1$-$C_4$ alkoxy, a $C_1$-$C_4$ haloalkoxy, an amino which is optionally substituted with one or more $C_1$-$C_4$ alkyl groups, an —$R_b$ group, a pyrrolyl group, an imidazolyl group, or two R groups together with the phenyl ring to which they are attached form a benzo [1,3]dioxole or 2,3-dihydro-benzo[1,4]dioxinyl group. Preferred R groups include those shown in the table below.

In an embodiment of Formula 1, R is preferably a halogen, a $C_1$-$C_4$ alkyl, a $C_1$-$C_4$ haloalkyl, a $C_1$-$C_4$ alkoxy, a $C_1$-$C_4$ haloalkoxy, an amino which is optionally substituted with one or more $C_1$-$C_4$ alkyl groups, an —$R_b$ group, a five to six membered heterocycle, or two R groups together with the phenyl ring to which they are attached form a benzo[1,3] dioxole or 2,3-dihydro-benzo[1,4]dioxinyl group.

In an embodiment of Formula 1, R is a halogen. In another embodiment of Formula 1, R is fluorine, chlorine, or bromine.

In an embodiment of Formula 1, R is a five to six membered heterocycle. In another embodiment of Formula 1, R is a five membered heterocycle that contains one or more nitrogen. In an embodiment of Formula 1, R is a five membered heterocycle that contains one nitrogen. In an embodiment of Formula 1, R is a five membered heterocycle that contains two nitrogens. In an embodiment of Formula 1, R is a five membered heterocycle that contains three nitrogens. In an embodiment of Formula 1, R is a five membered heterocycle that contains one oxygen. In an embodiment of Formula 1, R is a five membered heterocycle that contains two oxygens. In an embodiment of Formula 1, R is a five membered heterocycle that contains three oxygens. In a further embodiment of Formula 1, R is a five membered heterocycle that contains one or more oxygen and one or more nitrogen.

In another embodiment of Formula 1, R is a six membered heterocycle that contains one or more nitrogen. In an embodiment of Formula 1, R is a six membered heterocycle that contains one nitrogen. In an embodiment of Formula 1, R is a six membered heterocycle that contains two nitrogens. In an embodiment of Formula 1, R is a six membered heterocycle that contains three nitrogens. In an embodiment of Formula 1, R is a six membered heterocycle that contains one oxygen. In an embodiment of Formula 1, R is a six membered heterocycle that contains two oxygens. In an embodiment of Formula 1, R is a six membered heterocycle that contains three oxygens. In a further embodiment of Formula 1, R is a six membered heterocycle that contains one or more oxygen and one or more nitrogen.

In an embodiment of Formula 1, particularly preferred R groups include those shown in the table below.

| R | | |
|---|---|---|
| | methyl | isopropyl |
| t-butyl | chlorine | fluorine |
| bromine | —$CF_3$ | methoxy |
| ethoxy | —O—$CF_3$ | amino |
| dimethyl-amino | phenyl | |
| (N-methylmorpholinyl) | (N-imidazolyl) | two R groups together with the phenyl ring to which they are attached form 2,3-dihydro-benzo[1,4]dioxinyl group |

In an embodiment of Formula 1, n is 2 and both R groups are the same group.

In an embodiment of Formula 1, n is 3, and all 3 R groups are the same group.

In another embodiment of Formula 1, $R_1$ is preferably in a meta or para position and is preferably a cyano, a carbamoyl or a carbonyl group which is substituted with a hydroxy, a $C_1$-$C_4$ alkyl, or a $C_1$-$C_4$ alkoxy group. In a further embodiment, particularly preferred $R_1$ groups include those shown in the table below.

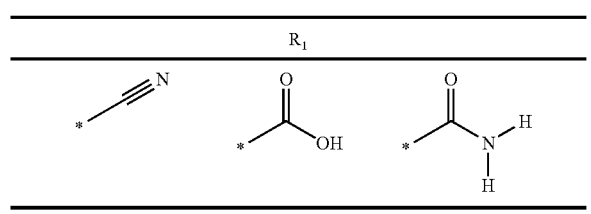

In a preferred embodiment, W, Y, and Z are each N, and X is C—R$_a$ (Formula 1-A):

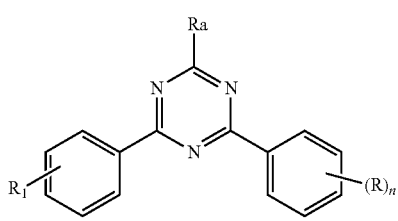

With reference to Formula 1-A, in an embodiment, R$_1$ is preferably a carboxy group, and is preferably located in a meta or para position. In another preferred embodiment of Formula 1-A, R$_a$ is hydrogen. In another preferred embodiment of Formula 1-A, R$_1$ is a carboxy group located in a meta or para position and R$_a$ is hydrogen. In a further embodiment, R$_a$ is preferably hydrogen, and n is preferably 1 or 2. In a further preferred embodiment, R$_a$ is hydrogen and n is 1. In another preferred embodiment of Formula 1-A, R$_1$ is a carboxy group located in a meta or para position, R$_a$ is hydrogen and n is 1 or 2. In another embodiment of Formula 1-A, R$_1$ is a carboxy group located in a meta or para position, R$_a$ is hydrogen and n is 1. R is preferably independently selected from a halogen, a C$_1$-C$_4$ alkyl, a C$_1$-C$_4$ haloalkyl, or a C$_1$-C$_4$ alkoxy, and is preferably located in a meta and/or para position, more preferably in a para position. In another preferred embodiment, R is independently selected from a methyl group, a fluorine group, a methoxy group, an ethoxy group, and a trifluoromethyl group.

In another preferred embodiment, Y and Z are both N, and W and X are both C—R$_a$ (Formula 1-B):

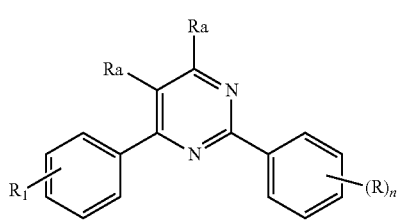

With reference to Formula 1-B, in a preferred embodiment, R$_a$ is hydrogen, and n is 0, 1 or 2. In another preferred embodiment, R$_a$ is hydrogen, and n is 1 or 2. In a further preferred embodiment of Formula 1-B, R$_a$ is hydrogen, and n is 1.

In an embodiment of Formula 1-B, R is independently selected from a halogen, a C$_1$-C$_4$ alkyl, a C$_1$-C$_4$ haloalkyl, a C$_1$-C$_4$ alkoxy, a C$_1$-C$_4$ haloalkoxy, amino, or pyrrolyl group, and is located in a meta and/or para position, preferably a para position. In a preferred embodiment, R is independently selected from a halogen, a C$_1$-C$_4$ alkyl, a C$_1$-C$_4$ haloalkyl, a C$_1$-C$_4$ alkoxy, a C$_1$-C$_4$ haloalkoxy, and an amino group, and is preferably located in a meta and/or para position, more preferably a para position. In a further preferred embodiment of Formula 1-B, R$_a$ is hydrogen, n is 1, and R is independently selected from a halogen, a C$_1$-C$_4$ alkyl, a C$_1$-C$_4$ haloalkyl, a C$_1$-C$_4$ alkoxy, a C$_1$-C$_4$ haloalkoxy, and an amino group.

In another preferred embodiment, R is independently selected from a fluorine, a chlorine, an amino group, a methyl group, an isopropyl group, a tert-butyl group, a methyl group, a trifluoromethyl group, a methoxy group, and a trifluoromethoxy group. In a further preferred embodiment of Formula 1-B, R$_a$ is hydrogen, n is 1, and R is independently selected from a fluorine, a chlorine, an amino group, a methyl group, an isopropyl group, a tert-butyl group, a methyl group, a trifluoromethyl group, a methoxy group, and a trifluoromethoxy group.

In yet another preferred embodiment, W and Y are both N, and X and Z are both C—R$_a$ (Formula 1-C):

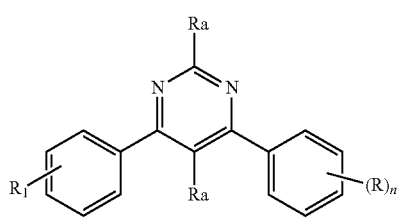

With reference to Formula 1-C, in an embodiment, R$_1$ is preferably a carboxy group, and is preferably located in a meta or para position. In a further embodiment of Formula 1-C, R$_a$ is preferably hydrogen, and n is 1 or 2. In a further embodiment of Formula 1-C, R$_a$ is preferably hydrogen, and n is preferably 1. In an embodiment, R is preferably a C$_1$-C$_4$ alkyl, and is preferably located in a meta and/or para position, more preferably the para position. In a preferred embodiment of Formula 1-C, R is a methyl group. In another preferred embodiment of Formula 1-C, R$_a$ is preferably hydrogen, n is preferably 1, and R is a C$_1$-C$_4$ alkyl. In another preferred embodiment of Formula 1-C, R$_a$ is preferably hydrogen, n is preferably 1, and R is a methyl group.

In yet another preferred embodiment, W and Z are both N, and X and Y are both C—R$_a$ (Formula 1-D):

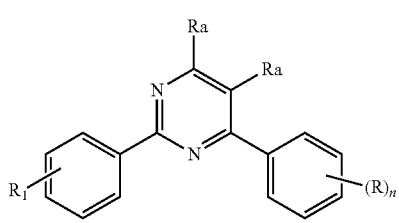

With reference to Formula 1-D, in a preferred embodiment, R$_1$ is a carboxy group, and is preferably located in a meta or para position. In one embodiment, X is C—CH$_3$ and Y is CH. In another embodiment, X is CH and Y is C—CH$_3$. In a preferred embodiment of Formula 1-D, R$_a$ is preferably independently selected from hydrogen or C$_1$-C$_4$ alkyl, and n is preferably 1 or 2. In another preferred embodiment of Formula 1-D, R$_a$ is preferably independently selected from hydrogen or C$_1$-C$_4$ alkyl, and n is preferably 1.

In a further preferred embodiment, R$_a$ is independently selected from hydrogen or methyl, and n is 1 or 2. In another preferred embodiment, $R_a$ is independently selected from hydrogen or methyl, and n is 1.

In yet another preferred embodiment, W is N, and X, Y, and Z are each C—$R_a$ (Formula 1-E):

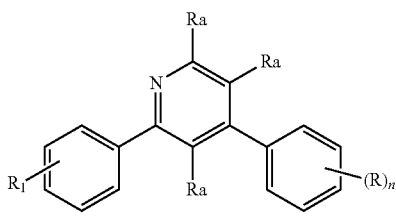

1-E

With reference to Formula 1-E, in an embodiment, $R_1$ is preferably a carboxy group, and is preferably located in a meta or para position. In a further embodiment, $R_a$ is preferably hydrogen, and n is preferably 1 or 2. In a preferred embodiment, $R_a$ is hydrogen, and n is 1. In an embodiment of Formula 1-E, R is preferably independently selected from a $C_1$-$C_4$ alkyl group, and is preferably located in the meta and/or para position, more preferably the para position. In a further embodiment, $R_a$ is preferably hydrogen, and n is preferably 1, and R is preferably a $C_1$-$C_4$ alkyl group. In another embodiment of Formula 1-E, R is preferably independently selected from a methyl group or an isopropyl group, and is preferably located in the meta and/or para position, more preferably the para position. In a further embodiment, $R_a$ is preferably hydrogen, n is preferably 1, and R is preferably a methyl group or an isopropyl group.

In yet another preferred embodiment, X is N, and W, Y, and Z are each C—$R_a$ (Formula 1-F):

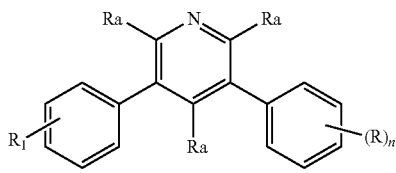

1-F

With reference to Formula 1-F, in an embodiment, $R_1$ is preferably a carboxy group, and is preferably located in a meta or para position. In another embodiment of Formula 1-F, $R_a$ is preferably hydrogen, and n is preferably 1 or 2. In a preferred embodiment of Formula 1-F, $R_a$ is hydrogen, and n is 1. In another preferred embodiment, R is preferably independently selected from a $C_1$-$C_4$ alkyl group, and is preferably located in the meta and/or para position, more preferably the para position. In another preferred embodiment, $R_a$ is hydrogen, n is 1, and R is $C_1$-$C_4$ alkyl group. In another preferred embodiment, R is independently selected from a methyl and an isopropyl group, and is preferably located in the meta and/or para position, more preferably the para position. In another preferred embodiment, $R_a$ is hydrogen, n is 1, and R is preferably selected from a methyl and an isopropyl group.

In yet another preferred embodiment, Y is N, and W, X, and Z are each C—$R_a$ (Formula 1-G):

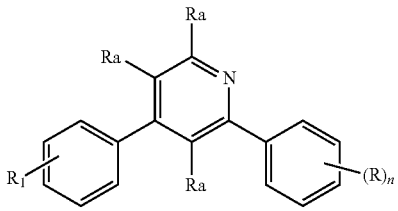

1-G

With reference to Formula 1-G, in a preferred embodiment, $R_1$ is a carboxy group, and is preferably located in a meta or para position. In another preferred embodiment, $R_a$ is preferably hydrogen, and n is preferably 1 or 2. In a further preferred embodiment, $R_a$ is preferably hydrogen, and n is preferably 1. In a preferred embodiment, R is preferably independently selected from a $C_1$-$C_4$ alkyl group, and is preferably located in the meta and/or para position, more preferably the para position. In another preferred embodiment, $R_a$ is hydrogen, and n is 1, and R is a $C_1$-$C_4$ alkyl group. In a preferred embodiment, R is preferably independently selected from a methyl or an isopropyl group, and is preferably located in the meta and/or para position, more preferably the para position. In another preferred embodiment, $R_a$ is hydrogen, and n is 1, and R is a methyl or an isopropyl group.

In yet another preferred embodiment, Z is N, and W, X, and Y are each C—$R_a$ (Formula 1-H):

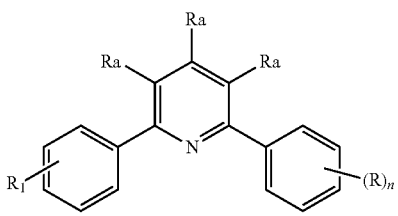

1-H

With reference to Formula 1-H, in a preferred embodiment, $R_1$ is preferably a carboxy group, and is preferably located in a meta or para position. In a further preferred embodiment, $R_a$ is hydrogen, and n is preferably 0 or 1. In a preferred embodiment, n is 1 and R is a $C_1$-$C_4$ alkyl group, and R is preferably located in the meta and/or para position, more preferably the para position. In another preferred embodiment, n is 1, R is a methyl group or an isopropyl group, and R is preferably located in the meta and/or para position, more preferably the para position.

In another embodiment, preferred compounds of the invention also include the compounds of Formula 2:

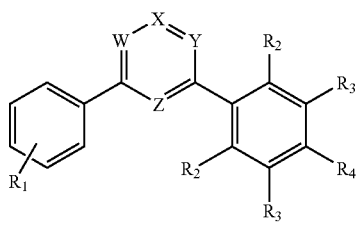

2 wherein:

W, X, Y and Z are independently selected from N or C—$R_a$, where $R_a$ is hydrogen or a $C_1$-$C_4$ alkyl group;

$R_1$ is a cyano group; a carbamoyl which is optionally substituted with one or two $C_1$-$C_4$ alkyl groups; or a carbonyl group which is substituted with a hydroxy, a $C_1$-$C_4$ alkyl, or a $C_1$-$C_4$ alkoxy group;

$R_2$ is independently selected from: hydrogen, a halogen, a $C_1$-$C_4$ alkyl group, or a $C_1$-$C_4$ haloalkyl group;

$R_3$ and $R_4$ are independently selected from: hydrogen; a halogen; a $C_1$-$C_4$ alkyl; a $C_1$-$C_4$ haloalkyl; a $C_1$-$C_4$ alkoxy; a $C_1$-$C_4$ haloalkoxy; an amino which is optionally substituted with one or more $C_1$-$C_4$ alkyl groups; an —$R_b$ group; a pyrrolyl group; an imidazolyl group; or two R groups together with the phenyl ring to which they are attached form a benzo[1,3]dioxole or 2,3-dihydro-benzo[1,4]dioxinyl group, wherein —$R_b$ is a $C_6$-$C_8$ aryl which is optionally substituted with one or more of the following: a hydroxy, a halogen, a $C_1$-$C_4$ alkyl group, a $C_1$-$C_4$ haloalkyl group, a $C_1$-$C_4$ alkoxy group, or an amino group which is optionally substituted with one or more $C_1$-$C_4$ alkyl groups;

or a pharmaceutically acceptable salt, hydrate, solvate, clathrate, polymorph, racemate or stereoisomer of said compound of Formula 2.

With reference to Formula 2, $R_1$ is preferably a cyano group, a carbamoyl group, or a carboxy group, and is preferably in the meta or para position. In an embodiment of Formula 2, preferred $R_2$, $R_3$, and $R_4$ groups are independently selected from the table below.

| R2 | R3 | R4 |
|---|---|---|
| hydrogen | hydrogen | hydrogen |
| methyl | methyl | methyl |
| chlorine | chlorine | isopropyl |
| fluorine | fluorine | t-butyl |
| —$CF_3$ | —$CF_3$ | chlorine |
| —$OCF_3$ | methoxy | fluorine |
|  | —O—$CF_3$ | bromine |
|  | together with $R_4$ and phenyl ring form 2,3-dihydro-benzo[1,4]dioxinyl group | together with $R_3$ and phenyl ring form 2,3-dihydro-benzo[1,4]dioxinyl group |
|  |  | —$CF_3$ |
|  |  | methoxy |
|  |  | ethoxy |
|  |  | —O—$CF_3$ |
|  |  | amino |
|  |  | dimethyl-amino |
|  |  | phenyl |
|  |  | *–N(morpholine) |
|  |  | *–N(imidazole) |

In a preferred embodiment of Formula 2, W, Y, and Z are each N, and X is C—$R_a$ (Formula 2-A):

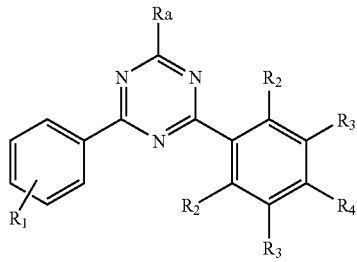

2-A

With reference to Formula 2-A, in a preferred embodiment, $R_1$ is preferably a carboxy group, and is preferably located in a meta or para position. In another preferred embodiment of Formula 2-A, $R_a$ and $R_2$ are preferably hydrogen. In a preferred embodiment of Formula 2-A, $R_3$ is independently selected from a hydrogen, a halogen, and a $C_1$-$C_4$ alkoxy group. In another preferred embodiment of Formula 2-A, $R_3$ is independently selected from hydrogen, a fluorine, and a methoxy group. In a preferred embodiment of Formula 2-A, $R_4$ is a hydrogen, a halogen, a $C_1$-$C_4$ alkyl, a $C_1$-$C_4$ haloalkyl, or a $C_1$-$C_4$ alkoxy. In another preferred embodiment of Formula 2-A, $R_4$ is a fluorine, a methyl, a trifluoromethyl, a methoxy or an ethoxy group.

In another preferred embodiment of Formula 2, Y and Z are both N, and W and X are both C—$R_a$ (Formula 2-B):

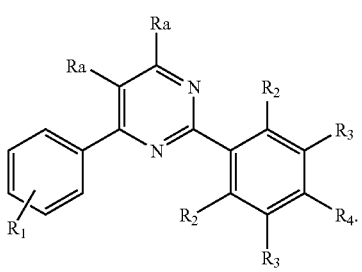

2-B

With reference to Formula 2-B, in a preferred embodiment, $R_1$ is a carboxy group, and is preferably located in a meta or para position. In a further preferred embodiment, $R_a$ is hydrogen. In a preferred embodiment of Formula 2-B, $R_2$ is independently selected from a hydrogen, a halogen, a $C_1$-$C_4$ alkyl, a $C_1$-$C_4$ haloalkyl, and a $C_1$-$C_4$ haloalkoxy. In another preferred embodiment of Formula 2-B, $R_2$ is independently selected from a hydrogen, a fluorine, a chlorine, a methyl, a trifluoromethyl and a trifluoromethoxy group.

In an embodiment of Formula 2-B, $R_3$ is preferably independently selected from a hydrogen, a halogen, a $C_1$-$C_4$ alkoxy, and a $C_1$-$C_4$ haloalkoxy. In a preferred embodiment of Formula 2-B, $R_3$ is independently selected from a hydrogen, a fluorine, a chlorine, a methoxy, and a trifluoromethoxy group.

In an embodiment of Formula 2-B, $R_4$ is a hydrogen, a halogen, a $C_1$-$C_4$ alkyl, a $C_1$-$C_4$ haloalkyl, a $C_1$-$C_4$ alkoxy, a $C_1$-$C_4$ haloalkoxy, an amino, or pyrrolyl group. In another embodiment of Formula 2-B, $R_4$ is preferably a hydrogen, a halogen, a $C_1$-$C_4$ alkyl, a $C_1$-$C_4$ haloalkyl, a $C_1$-$C_4$ alkoxy, a $C_1$-$C_4$ haloalkoxy, or an amino group. In a preferred embodiment of Formula 2-B, $R_4$ is a hydrogen, a fluorine, a chlorine, a methyl, an isopropyl, a tert-butyl, a trifluoromethyl, a methoxy, a trifluoromethoxy, or an amino group.

In yet another preferred embodiment of Formula 2, W and Y are both N, and X and Z are both C—$R_a$ (Formula 2-C):

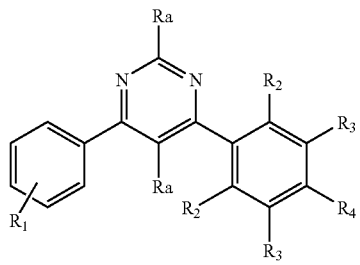

2-C

With reference to Formula 2-C, in a preferred embodiment, $R_1$ is a carboxy group, and is preferably located in a meta or para position. In a preferred embodiment of Formula 2-C, $R_a$ is hydrogen. In another preferred embodiment of Formula 2-C, $R_3$ is independently selected from hydrogen or a $C_1$-$C_4$ alkyl. In a further preferred embodiment of Formula 2-C, $R_3$ is independently selected from hydrogen or a methyl group. In another preferred embodiment of Formula 2-C, $R_4$ is hydrogen or a $C_1$-$C_4$ alkyl. In a further preferred embodiment of Formula 2-C, $R_4$ is hydrogen or a methyl group.

In yet another preferred embodiment of Formula 2, W and Z are both N, and X and Y are both C—$R_a$ (Formula 2-D):

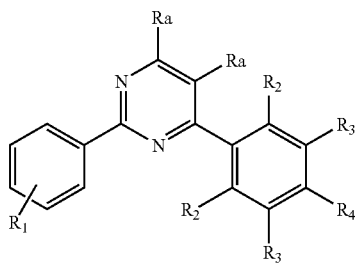

2-D

With reference to Formula 2-D, in an embodiment, $R_1$ is preferably a carboxy group, and is preferably located in a meta or para position. In another embodiment of Formula 2-D, $R_a$ is preferably independently selected from hydrogen or methyl. In one embodiment, X is C—$CH_3$ and Y is CH. In another embodiment, X is CH and Y is C—$CH_3$.

In an embodiment of Formula 2-D, $R_2$ is preferably independently selected from hydrogen or a halogen. In a preferred embodiment of Formula 2-D, $R_2$ is independently selected from hydrogen or a fluorine. In an embodiment of Formula 2-D, $R_3$ is preferably independently selected from hydrogen, a halogen, a $C_1$-$C_4$ alkyl, a $C_1$-$C_4$ alkoxy, a $C_1$-$C_4$ haloalkoxy, or together with $R_4$ and the phenyl ring to which $R_3$ and $R_4$ are attached form a benzo[1,3]dioxole or a 2,3-dihydro-benzo[1,4]dioxinyl group. In another embodiment of Formula 2-D, $R_3$ is independently selected from hydrogen, a halogen, a $C_1$-$C_4$ alkoxy group, or together with $R_4$ and the phenyl ring to which $R_3$ and $R_4$ are attached form a benzo[1,3]dioxole or a 2,3-dihydro-benzo[1,4]dioxinyl group. In a preferred embodiment of Formula 2-D, $R_3$ is preferably independently selected from hydrogen, a fluorine, a methyl group, a trifluoromethyl group, a methoxy group, or together with $R_4$ and the phenyl ring to which $R_3$ and $R_4$ are attached form a benzo[1,3]dioxole or a 2,3-dihydro-benzo[1,4]dioxinyl group.

In an embodiment of Formula 2-D, $R_4$ is preferably hydrogen, a halogen, a $C_1$-$C_4$ alkyl, a $C_1$-$C_4$ haloalkyl, a $C_1$-$C_4$ alkoxy, a $C_1$-$C_4$ haloalkoxy, an amino optionally substituted with one or two $C_1$-$C_4$ alkyl groups, an —$R_b$ group, an imidazolyl group, a morpholinyl group, or together with $R_3$ and the phenyl ring to which $R_3$ and $R_4$ are attached form a benzo[1,3]dioxole or a 2,3-dihydro-benzo[1,4]dioxinyl group. In another embodiment of Formula 2-D, $R_4$ is preferably hydrogen, a halogen, a $C_1$-$C_4$ alkyl, a $C_1$-$C_4$ haloalkyl, a $C_1$-$C_4$ alkoxy, a $C_1$-$C_4$ haloalkoxy, an amino optionally substituted with one or two $C_1$-$C_4$ alkyl groups, an —$R_b$ group, an imidazolyl group, or together with $R_3$ and the phenyl ring to which $R_3$ and $R_4$ are attached form a benzo[1,3]dioxole or a 2,3-dihydro-benzo[1,4]dioxinyl group. In a preferred embodiment of Formula 2-D, $R_4$ is selected from the following groups: a fluorine, a bromine, a methyl, an isopropyl, a trifluoromethyl, a methoxy, a trifluoromethoxy, a phenyl, an imidazolyl, a morpholinyl, and an amino substituted with two methyl groups.

In yet another preferred embodiment of Formula 2, W is N, and X, Y, and Z are each C—$R_a$ (Formula 2-E):

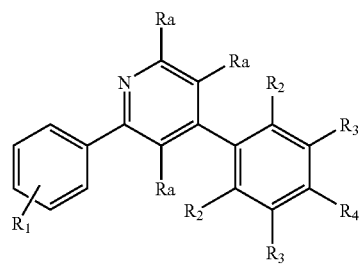

2-E

With reference to Formula 2-E, in an embodiment, $R_1$ is preferably a carboxy group, and is preferably located in a meta or para position. In another embodiment of Formula 2-E, $R_a$, $R_2$, and $R_3$ are preferably hydrogen. In a preferred embodiment of Formula 2-E, $R_4$ is a $C_1$-$C_4$ alkyl group. In another preferred embodiment of Formula 2-E, $R_4$ is a methyl or an isopropyl group.

In yet another preferred embodiment of Formula 2, X is N, and W, Y, and Z are each C—$R_a$ (Formula 2-F):

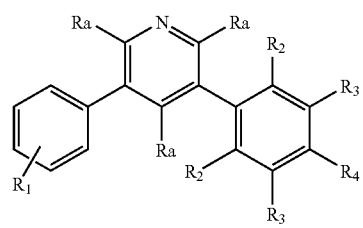

2-F

With reference to Formula 2-F, in an embodiment, $R_1$ is preferably a carboxy group, and is preferably located in a meta or para position. In a preferred embodiment of Formula 2-F, $R_a$, $R_2$, and $R_3$ are preferably hydrogen. In another preferred embodiment of Formula 2-F, $R_4$ is a $C_1$-$C_4$ alkyl group. In another preferred embodiment of Formula 2-F, $R_4$ is a methyl or an isopropyl group.

In yet another preferred embodiment of Formula 2, Y is N, and W, X, and Z are each C—$R_a$ (Formula 2-G):

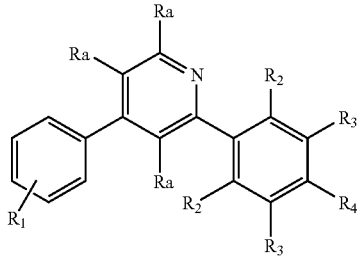

2-G

With reference to Formula 2-G, in an embodiment, $R_1$ is preferably a carboxy group, and is preferably located in a meta or para position. In a preferred embodiment of Formula 2-G, $R_a$, $R_2$, and $R_3$ are preferably hydrogen. In another preferred embodiment of Formula 2-G, $R_4$ is a $C_1$-$C_4$ alkyl group. In another preferred embodiment of Formula 2-G, $R_4$ is a methyl or an isopropyl group.

In yet another preferred embodiment of Formula 2, Z is N, and W, X, and Y are each C—$R_a$ (Formula 2-H):

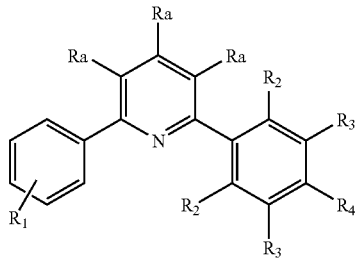

2-H

With reference to Formula 2-H, in an embodiment, $R_1$ is preferably a carboxy group, and is preferably located in a meta or para position. Further, in a preferred embodiment of Formula 2-H, $R_a$, $R_2$, and $R_3$ are preferably hydrogen. In a preferred embodiment, $R_4$ is hydrogen or a $C_1$-$C_4$ alkyl group. In another preferred embodiment, $R_4$ is hydrogen or a methyl or an isopropyl group. In a further preferred embodiment, $R_4$ is hydrogen. In another preferred embodiment, $R_4$ is a methyl or an isopropyl group.

Preferred compounds of the invention include the following.

-continued

Compound

8

[Structure: 4-isopropylphenyl-pyridine-phenyl-COOH]

9

[Structure: pyrimidine with p-tolyl and phenyl-COOH (meta)]

10

[Structure: pyrimidine with p-tolyl and phenyl-COOH (para)]

11

[Structure: pyridine with 4-isopropylphenyl and phenyl-COOH (meta)]

12

[Structure: pyridine with p-tolyl and phenyl-COOH (para)]

-continued

Compound

13

[Structure: pyridine 2,4-disubstituted with p-tolyl and phenyl-COOH]

14

[Structure: pyridine 2,6-disubstituted with p-tolyl and phenyl-COOH]

15

[Structure: pyridine 3,5-disubstituted with p-tolyl and phenyl-COOH]

16

[Structure: pyrimidine with 3-methoxyphenyl and phenyl-COOH]

17

[Structure: pyrimidine with 4-tert-butylphenyl and phenyl-COOH]

18

[Structure: pyrimidine with 4-fluorophenyl and phenyl-COOH]

| Compound | | Compound |
|---|---|---|
| 19 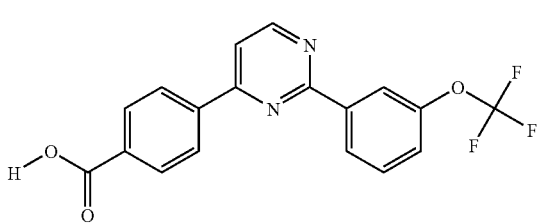 [SMILES: O=C(O)c1ccc(-c2ccnc(-c3cccc(OC(F)(F)F)c3)n2)cc1] | | 25 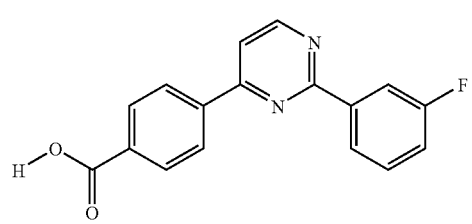 |
| 20 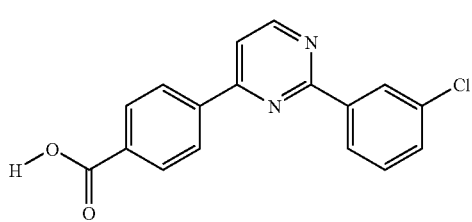 [SMILES: O=C(O)c1ccc(-c2ccnc(-c3cccc(Cl)c3)n2)cc1] | | 26 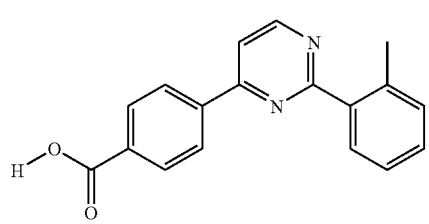 |
| 21 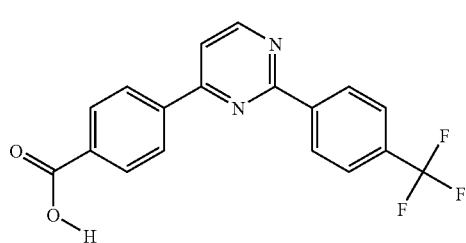 [SMILES: O=C(O)c1ccc(-c2ccnc(-c3ccc(C(F)(F)F)cc3)n2)cc1] | | 27 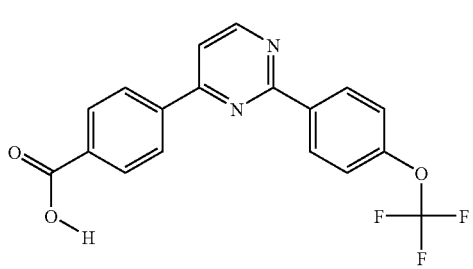 |
| 22 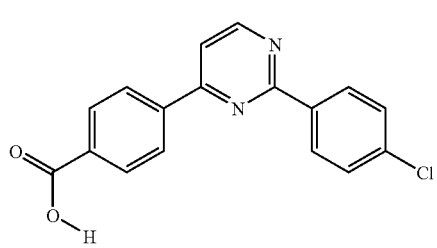 [SMILES: O=C(O)c1ccc(-c2ccnc(-c3ccc(Cl)cc3)n2)cc1] | | 28 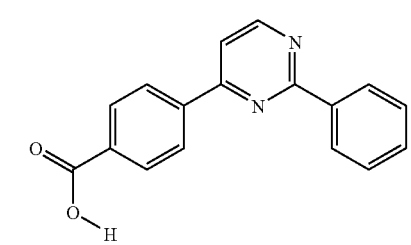 |
| 23 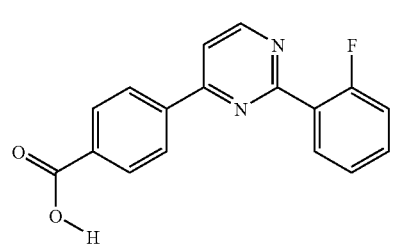 | | 29 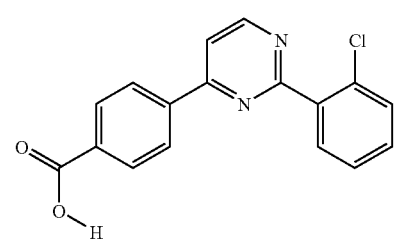 [SMILES: O=C(O)c1ccc(-c2ccnc(-c3ccccc3F)n2)cc1] |
| 24 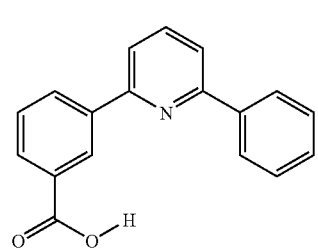 [SMILES: O=C(O)c1cccc(-c2cccc(-c3ccccc3)n2)c1] | | 30 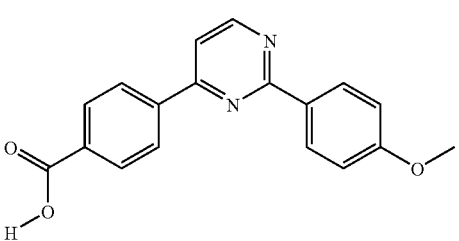 [SMILES: COc1ccc(-c2nccc(-c3ccc(C(=O)O)cc3)n2)cc1] |

| Compound | | Compound | |
|---|---|---|---|
| 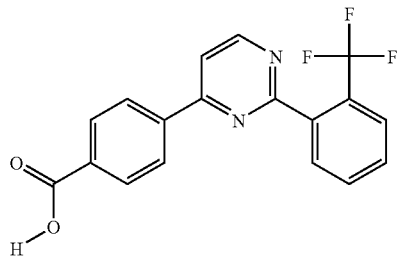 [SMILES: O=C(O)c1ccc(-c2ccnc(-c3ccccc3C(F)(F)F)n2)cc1] | 31 | 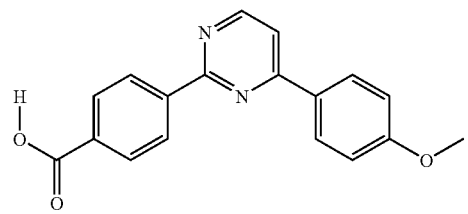 | 37 |
| 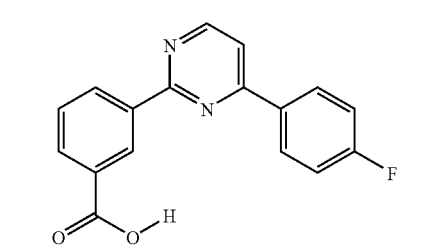 [SMILES: O=C(O)c1cccc(-c2nccc(-c3ccc(F)cc3)n2)c1] | 32 | 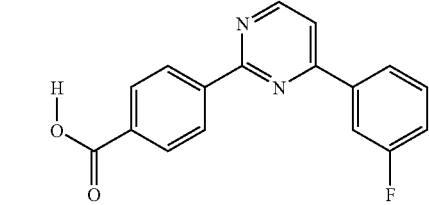 | 38 |
| 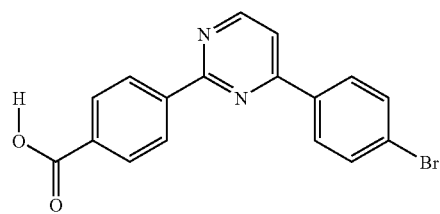 [SMILES: O=C(O)c1ccc(-c2nccc(-c3ccc(Br)cc3)n2)cc1] | 33 | 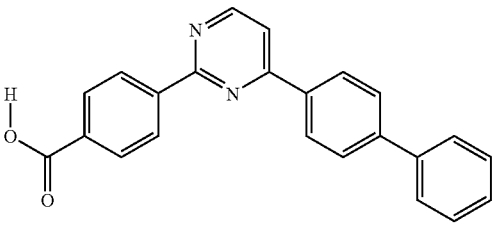 | 39 |
| 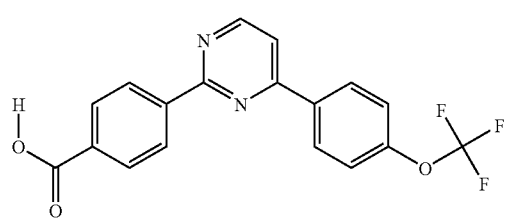 [SMILES: O=C(O)c1ccc(-c2nccc(-c3ccc(OC(F)(F)F)cc3)n2)cc1] | 34 | 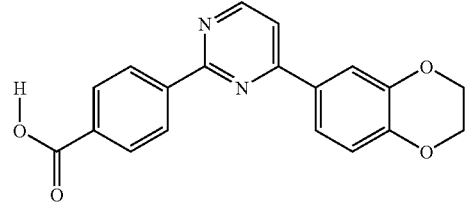 | 40 |
| 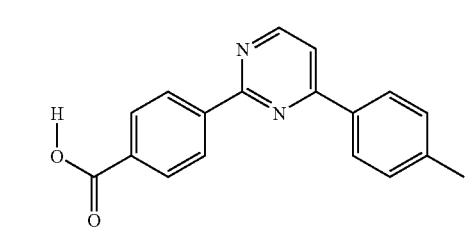 | 35 | 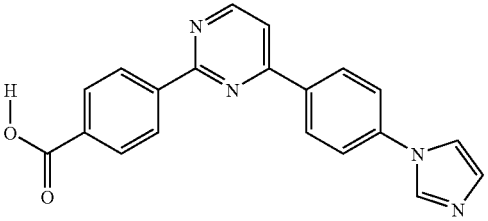 | 41 |
| 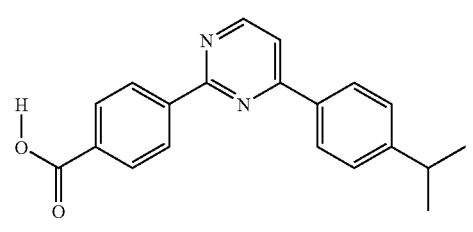 | 36 | 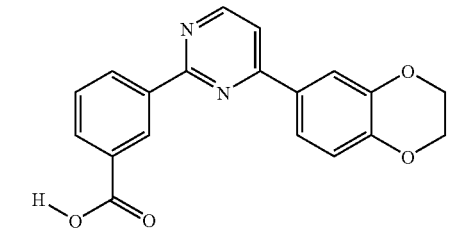 [SMILES: O=C(O)c1cccc(-c2nccc(-c3ccc4c(c3)OCCO4)n2)c1] | 42 |

| Compound | Compound |
|---|---|
| 43 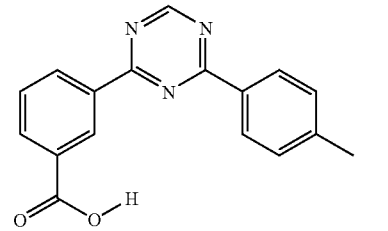 [SMILES: Cc1ccc(-c2ncnc(-c3cccc(C(=O)O)c3)n2)cc1] | 49 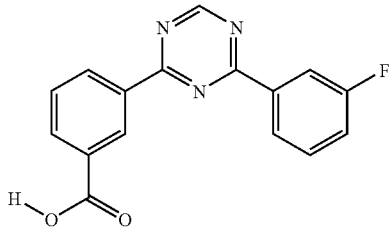 |
| 44 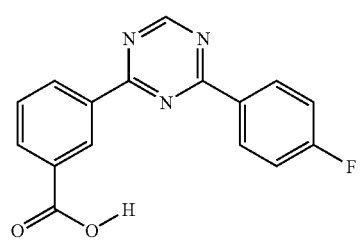 | 50 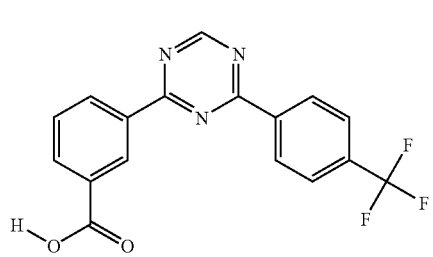 |
| 45 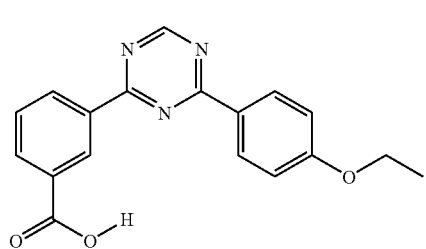 [SMILES: CCOc1ccc(-c2ncnc(-c3cccc(C(=O)O)c3)n2)cc1] | 51 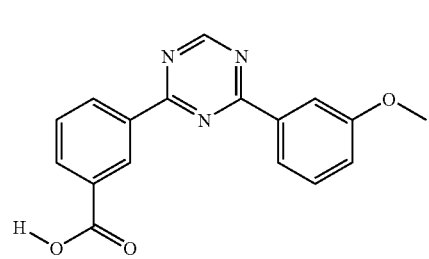 |
| 46 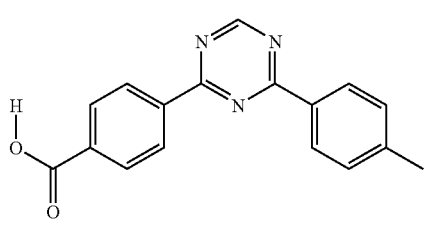 | 52 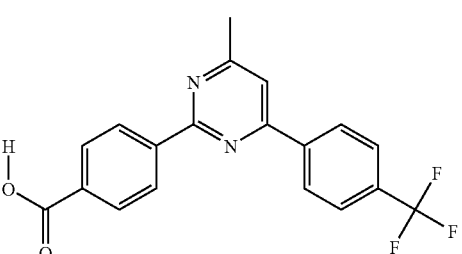 |
| 47 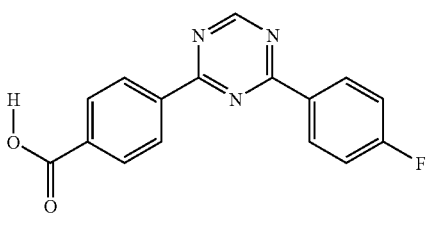 [SMILES: O=C(O)c1ccc(-c2ncnc(-c3ccc(F)cc3)n2)cc1] | 53 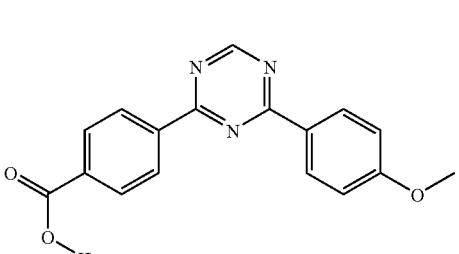 |
| 48 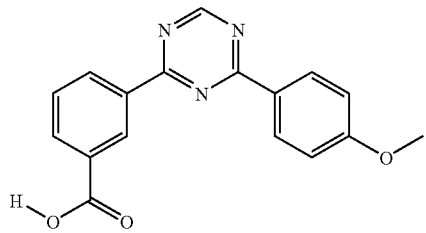 [SMILES: COc1ccc(-c2ncnc(-c3cccc(C(=O)O)c3)n2)cc1] | 54 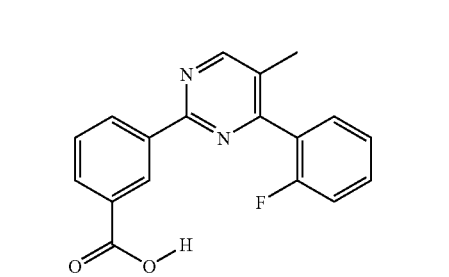 [SMILES: Cc1cnc(-c2cccc(C(=O)O)c2)nc1-c1ccccc1F] |

| Compound | | Compound |
|---|---|---|
| 55 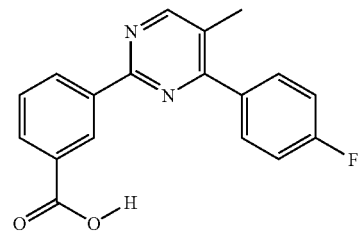 [SMILES: Cc1cnc(-c2cccc(C(=O)O)c2)nc1-c1ccc(F)cc1] | | 61 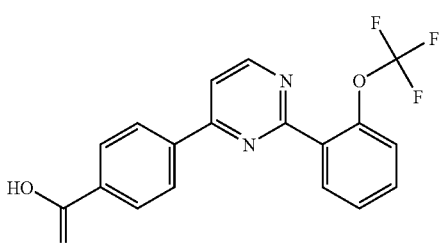 |
| 56 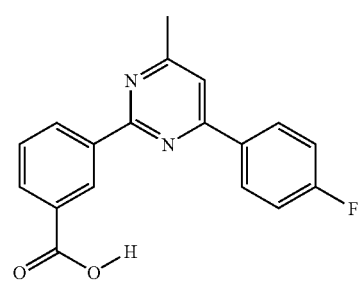 [SMILES: Cc1cc(-c2ccc(F)cc2)nc(-c2cccc(C(=O)O)c2)n1] | | 62 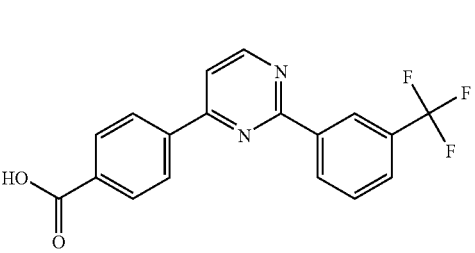 |
| 57 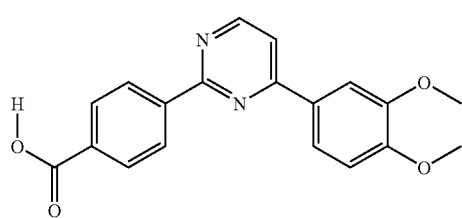 [SMILES: COc1ccc(-c2ccnc(-c3ccc(C(=O)O)cc3)n2)cc1OC] | | 63 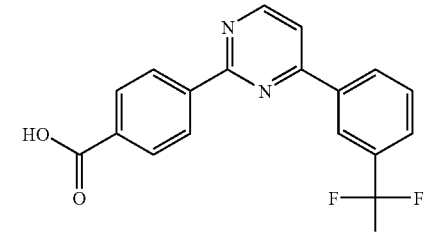 |
| 58 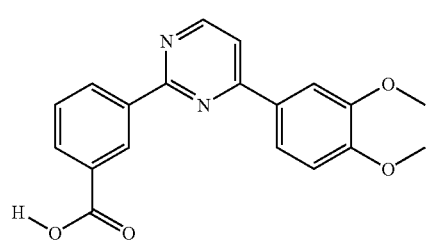 | | 64 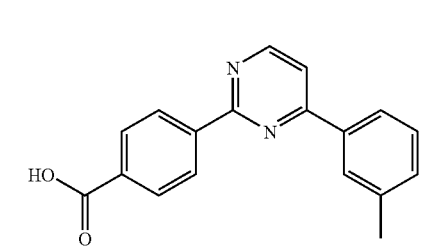 |
| 59 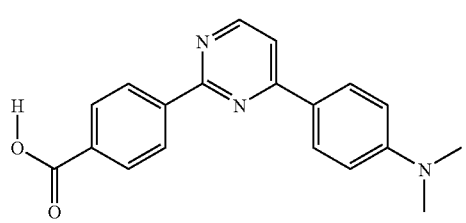 | | 65 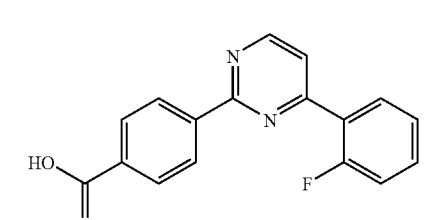 |
| 60 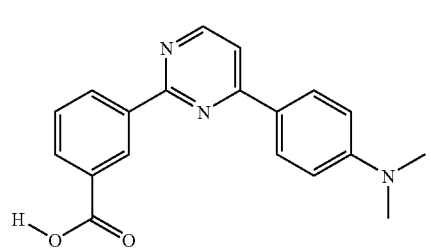 [SMILES: CN(C)c1ccc(-c2ccnc(-c3cccc(C(=O)O)c3)n2)cc1] | | 66 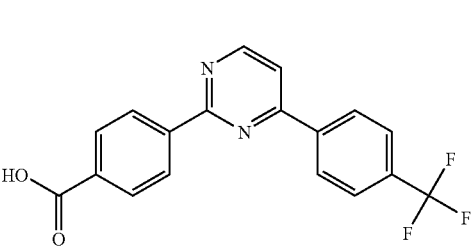 [SMILES: O=C(O)c1ccc(-c2nccc(-c3ccc(C(F)(F)F)cc3)n2)cc1] |

TABLE-continued
Compound
| 67 | 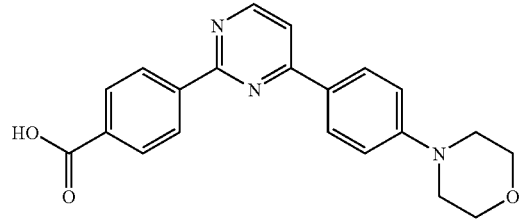 [SMILES: O=C(O)c1ccc(-c2nccc(-c3ccc(N4CCOCC4)cc3)n2)cc1] |
| --- | --- |
| 68 | 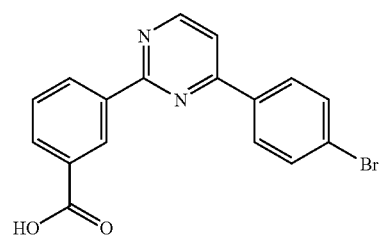 [SMILES: O=C(O)c1cccc(-c2nccc(-c3ccc(Br)cc3)n2)c1] |
| 69 | 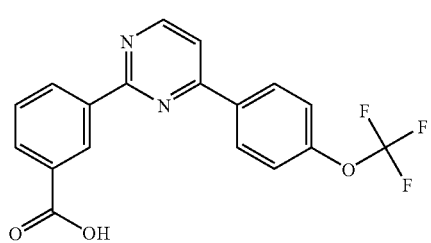 [SMILES: O=C(O)c1cccc(-c2nccc(-c3ccc(OC(F)(F)F)cc3)n2)c1] |
| 70 | 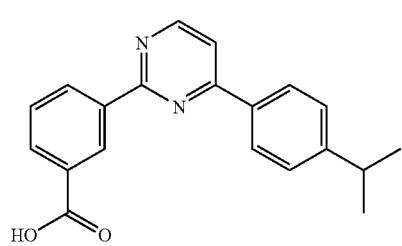 [SMILES: CC(C)c1ccc(-c2ccnc(-c3cccc(C(=O)O)c3)n2)cc1] |
| 71 | 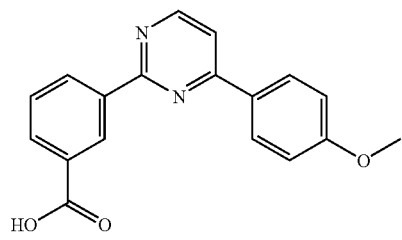 [SMILES: COc1ccc(-c2ccnc(-c3cccc(C(=O)O)c3)n2)cc1] |
| 72 | 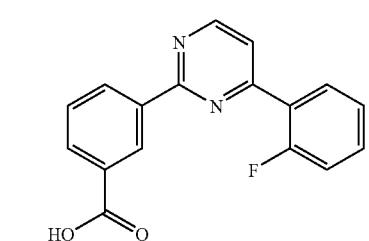 [SMILES: O=C(O)c1cccc(-c2nccc(-c3ccccc3F)n2)c1] |
| 73 | 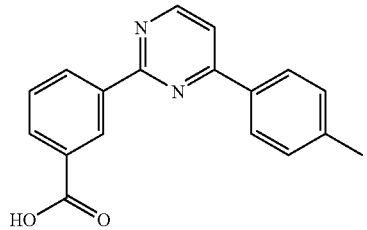 [SMILES: Cc1ccc(-c2ccnc(-c3cccc(C(=O)O)c3)n2)cc1] |
| 74 | 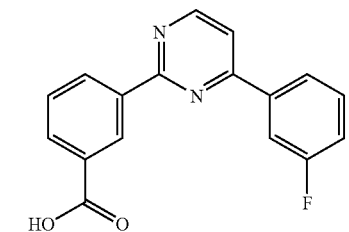 |
| 75 | 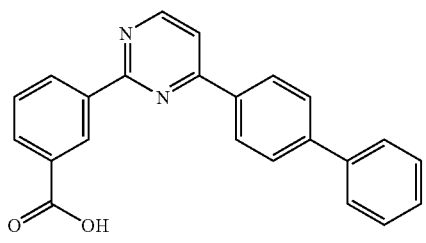 [SMILES: O=C(O)c1cccc(-c2nccc(-c3ccc(-c4ccccc4)cc3)n2)c1] |
| 76 | 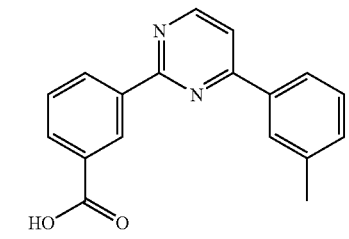 [SMILES: Cc1cccc(-c2ccnc(-c3cccc(C(=O)O)c3)n2)c1] |
| 77 | 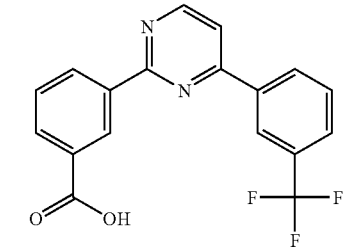 [SMILES: O=C(O)c1cccc(-c2nccc(-c3cccc(C(F)(F)F)c3)n2)c1] |
| 78 | 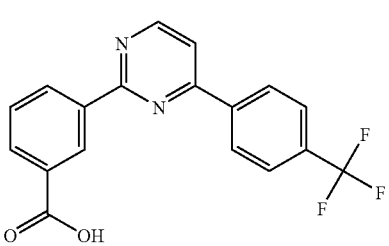 [SMILES: O=C(O)c1cccc(-c2nccc(-c3ccc(C(F)(F)F)cc3)n2)c1] |

| Compound | Compound |
|---|---|
| 79 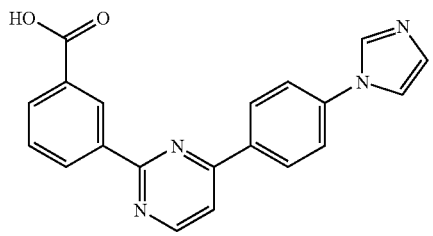 [SMILES: O=C(O)c1cccc(-c2nccc(-c3ccc(-n4ccnc4)cc3)n2)c1] | 85 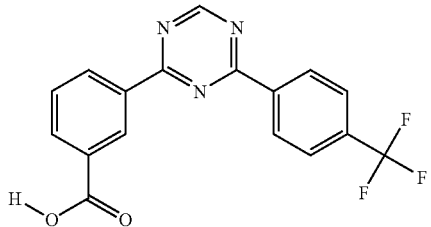 [SMILES: O=C(O)c1cccc(-c2ncnc(-c3ccc(C(F)(F)F)cc3)n2)c1] |
| 80 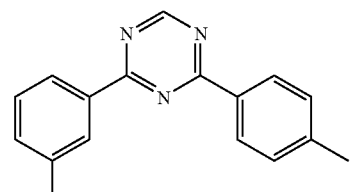 | 86 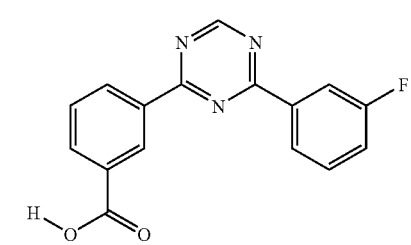 [SMILES: O=C(O)c1cccc(-c2ncnc(-c3cccc(F)c3)n2)c1] |
| 81 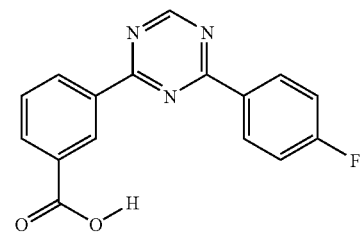 | 87 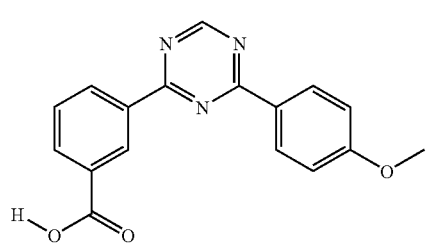 [SMILES: COc1ccc(-c2ncnc(-c3cccc(C(=O)O)c3)n2)cc1] |
| 82 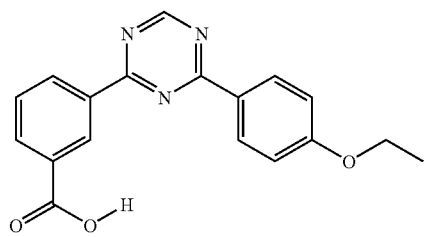 | 88 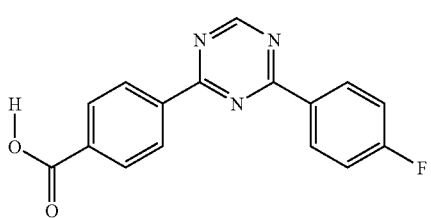 [SMILES: O=C(O)c1ccc(-c2ncnc(-c3ccc(F)cc3)n2)cc1] |
| 83 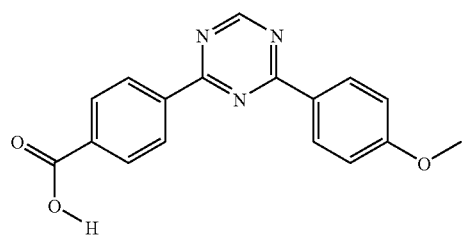 | 89 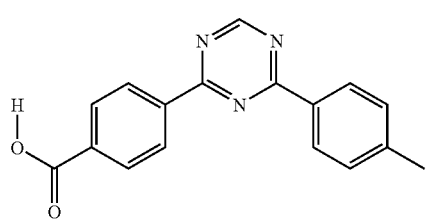 [SMILES: Cc1ccc(-c2ncnc(-c3ccc(C(=O)O)cc3)n2)cc1] |
| 84 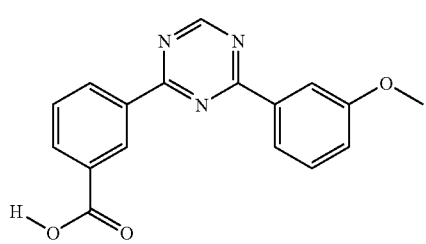 | |

Particularly preferred compounds are Compound NOs: 10, 33, 35, 36, 37, 40, 42, 43, 56, 60, 63, 64, 65, 66, and 71.

The above compounds are listed only to provide examples that may be used in the methods of the invention. Based upon the instant disclosure, the skilled artisan would recognize other compounds intended to be included within the scope of the presently claimed invention that would be useful in the methods recited herein.

B. Preparation of Compounds of the Invention

Compounds of the invention may be produced in any manner known in the art. By way of example, compounds of the invention may be prepared according to the following general schemes with reference to the individual azine ring core structures. For example, triazine compounds of Formulas 1-A and 2-A may be prepared in the manner shown in Scheme A.

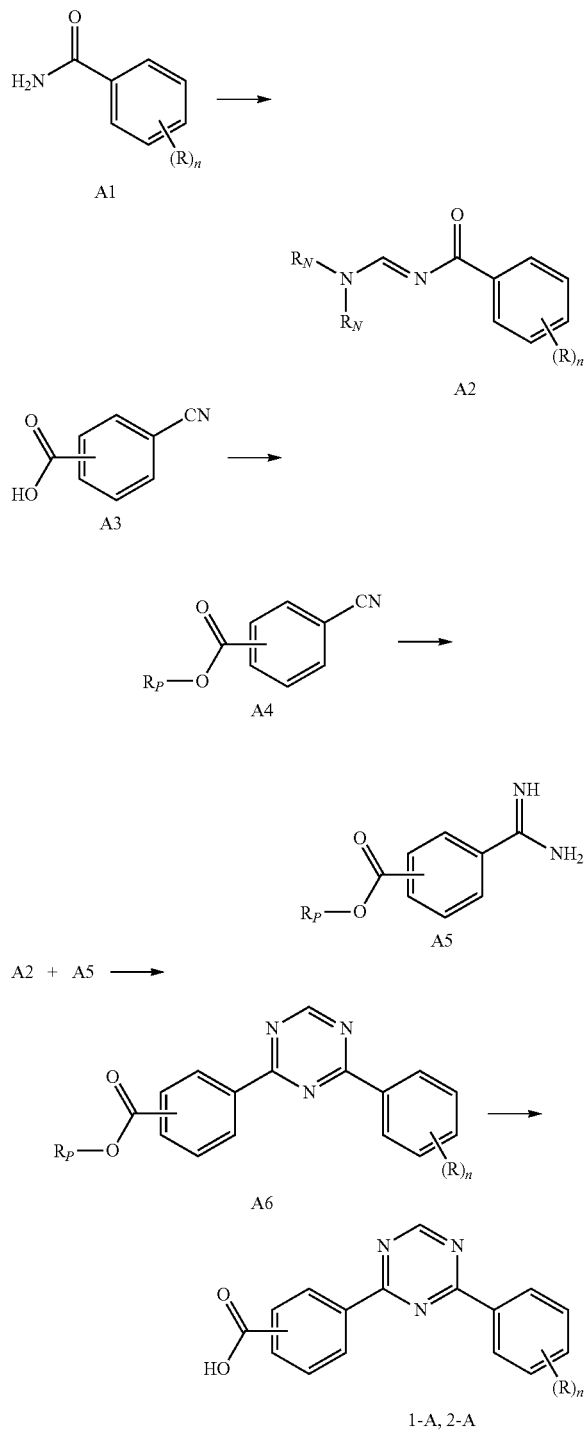

Scheme A

In accordance with Scheme A, a benzamide substrate of Formula A1 is treated with a reagent of the formula $(R_N)_2NCH(Oalkyl)_2$ wherein $R_N$ is usually a small alkyl or the two $R_N$ group taken together form a five- or six-membered ring (e.g. pyrrolidine, piperazine, morpholine, etc.), and Oalkyl is a small alkoxy group such as methoxy or ethoxy. This condensation reaction may be performed either in neat formamide acetal reagent or in a higher-boiling solvent such as ethanol or acetic acid to afford the benzoyl formamidine product of Formula A2.

In a separate reaction, a cyanobenzoic acid reagent of Formula A3 may be transformed into an ester compound of Formula A4. The group $R_P$ can represent an alkyl group, straight-chain or branched. Such esterification reactions are familiar to those skilled in the art, and include but are not limited to: a) conversion to the benzoyl chloride, then treatment with the corresponding alcohol reagent of the formula $R_POH$, in the presence of a base; b) in situ activation with a dehydrating reagent such as a carbodiimide; or c) use of the Mitsunobu conditions, which employ a phosphine compound and a diazocarboxylate reagent. $R_P$ is preferably as bulky as possible, and may be tert-butyl, may be attached by an acid-catalyzed reaction with isobutylene, or by condensation of tert-butanol with the benzoyl chloride, as discussed above. In another embodiment, a solid support may be used as $R_P$, which may aid in the purification of intermediates. Solid supports common in combinatorial synthetic chemistry may be used, including Wang resins, Janda resins, etc.

The nitrile group in the compound of Formula A4 may then converted to an amidine group to give a compound of Formula A5. This transformation may be accomplished by treatment with a reagent such as lithium, sodium or potassium hexamethyldisilazide in an aprotic solvent such as tetrahydrofuran or 1,4-dioxane, at temperatures ranging from subzero to reflux. Aqueous workup and neutralization may then be used remove the silicon groups and yield the amidine product. Other such conversions may involve acid-catalyzed amination of the nitrile group.

The compounds of Formula A2 and A5 may then be allowed to undergo a cyclocondensation reaction to for the triazine ring in the compound of Formula A6. This reaction may be acid-catalyzed in a higher-boiling solvent, such as acetic acid, glyme, etc. The reaction may also be accelerated by using a microwave reactor. The final step of the synthesis generally involves deprotection of the carboxylate group in the compound of Formula A6, if desired. For sterically-unhindered $R_P$ groups, this is preferably accomplished by treatment with a hydroxide salt (such as lithium hydroxide or sodium hydroxide) in a solvent such as ethanol, THF, etc., usually in the presence of a little water at ambient-to-elevated temperatures. Small $R_P$ groups (especially methyl) may be removed by a nucleophilic reagent such as lithium iodide in a polar solvent such as dimethyl sulfoxide or pyridine. Finally, acid-labile $R_P$ groups such as tert-butyl may be cleaved under the conditions of the previous reaction (i.e. to get A6) to afford the carboxylic acid directly, with stronger acid conditions if necessary.

General methods used in the synthesis of the pyrimidines (Formulas 1-B and 2-B) are shown in Scheme B.

Scheme B

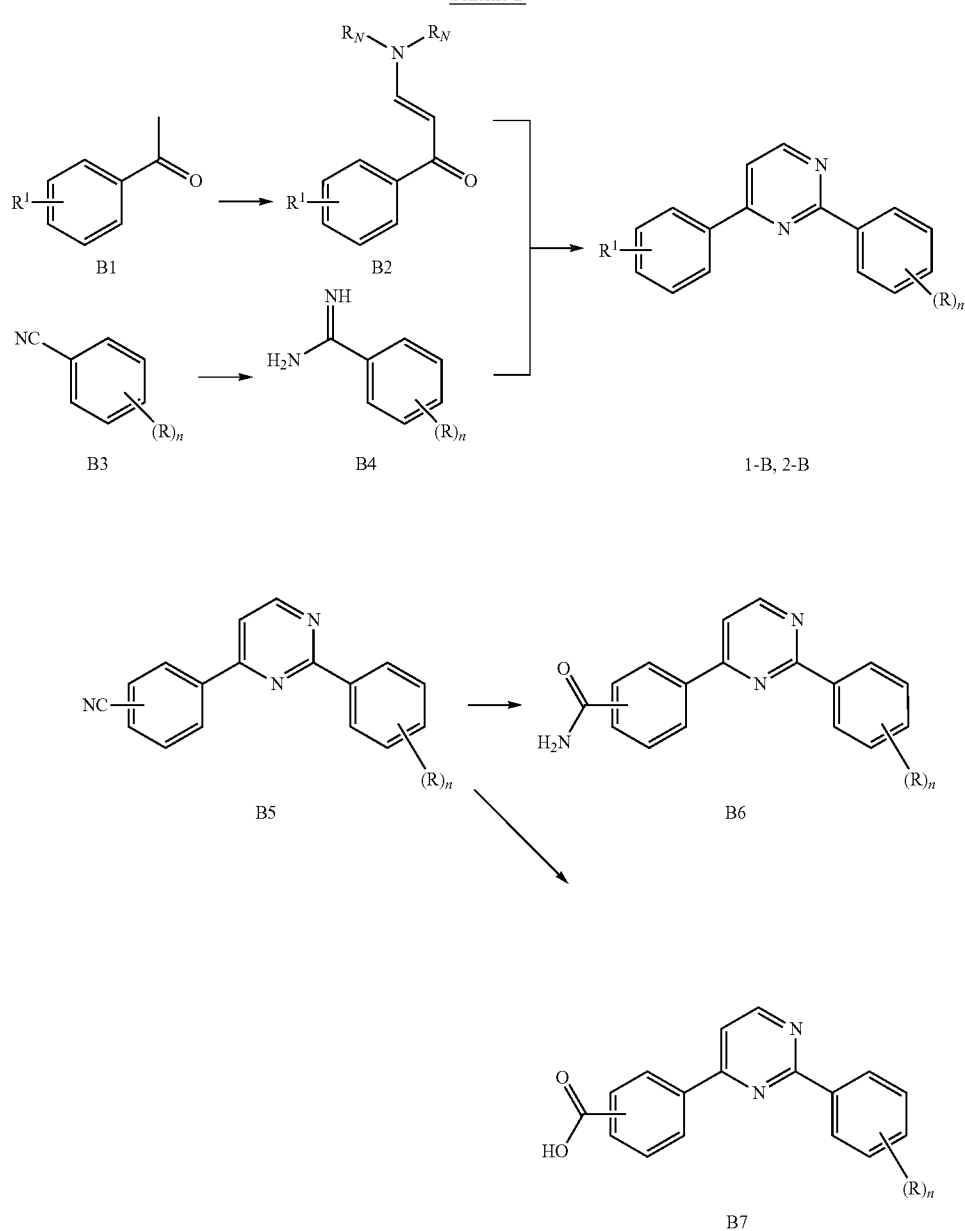

An acetophenone substrate of Formula B1 may be reacted with a formamide acetal reagent in a manner similar as for the transformation A1 to A2 to afford the product of Formula B2. In a separate reaction, a benzonitrile compound of Formula B3 may be converted to the amidine of Formula B4, in an manner analogous to the conversion of A4 to A5. The condensation reaction of the compounds of Formulae B2 and B4 may then generate the pyrimidine product of Formulas 1-B or 2-B. This reaction may be performed in the presence of a base (such as sodium hydride or sodium ethoxide) in a polar solvent (such as ethanol or 1,4-dioxane) at elevated temperatures. Interconversion of $R_1$ groups is possible, and is exemplified by the reactions of the nitrile compound of Formula B5. The nitrile may be hydrolyzed to the carboxamide using strong aqueous acid (hydrochloric or sulfuric) to afford the compound of Formula B6. Similarly, basic conditions (for example, sodium hydroxide) may be employed to hydrolyzed the nitrile group to the carboxy group in the product of Formula B7.

General methods used in the synthesis of the 4,6-diarylpyrimidines of Formulas 1-C and 2-C is shown in Scheme C, below.

Scheme C

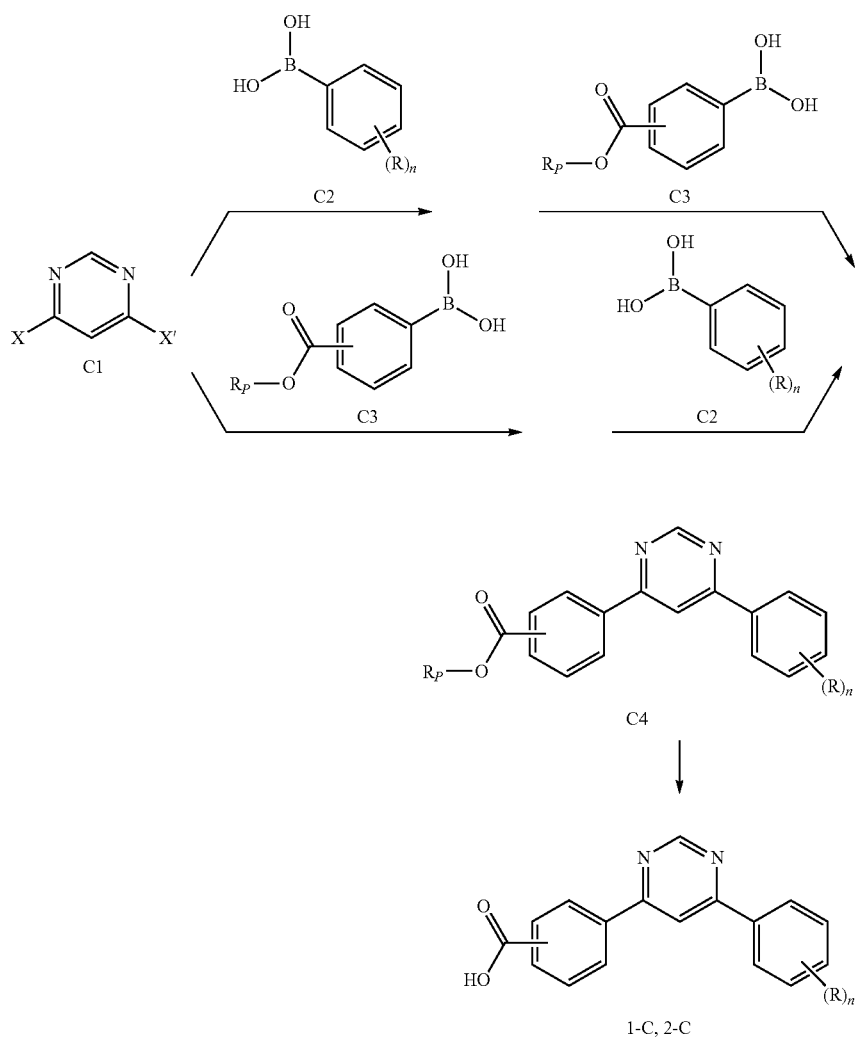

A 4,6-dihalopyrimidine of Formula C1 may be used in sequential Suzuki reactions with boronic acid derivatives of two aryl groups (Formulae C2 and C3), wherein X represents a group that can be displaced in aryl cross-coupling reactions, such as chloro, bromo, iodo or trifluoromethanesulfonyl. To improve selectivity for the overall transformation, it may be necessary to use a substrate with different halogens (i.e. X≠X'). Another approach may involve using an X' group which is a masked halogen; for example, an aryl amino group which can be converted to halogen via diazotization followed by displacement by halogen. In the event that the compound of Formulae C2 or C3 is not available from commercial sources, they may be prepared by metal-halogen exchange (of a bromo or iodo with lithium, magnesium, zinc, etc.) followed by quenching with a source of boron, such as trimethylborate or triisopropylborate.

The cross-coupling reaction may be catalyzed by compounds such as tetrakis(triphenylphosphine), palladium acetate or bis(triphenylphosphine)palladium dichloride optionally with the addition of a phosphine ligand such as triphenylphosphine, BINAP, etc. The reaction may also require the presence of a base such as sodium carbonate, potassium triphosphate or cesium fluoride. Appropriate solvents for the Suzuki-type cross-coupling reaction include ethanol, toluene, 1,4-dioxane or glyme, and the reaction proceeds preferentially in the absence of oxygen, so the solvent may preferably be degassed. The isolation of the intermediate mono-coupled compound may be advantageous in terms of final product purification. Also, the carboxylate protecting group may be removed if desired at the final step to give the final product of Formulas 1-C and 2-C.

The general methods discussed in associated with Scheme B may be adapted to the reverse pyrimidine regioisomer of Formulas 1-D and 2-D, as shown below in Scheme D.

Scheme D

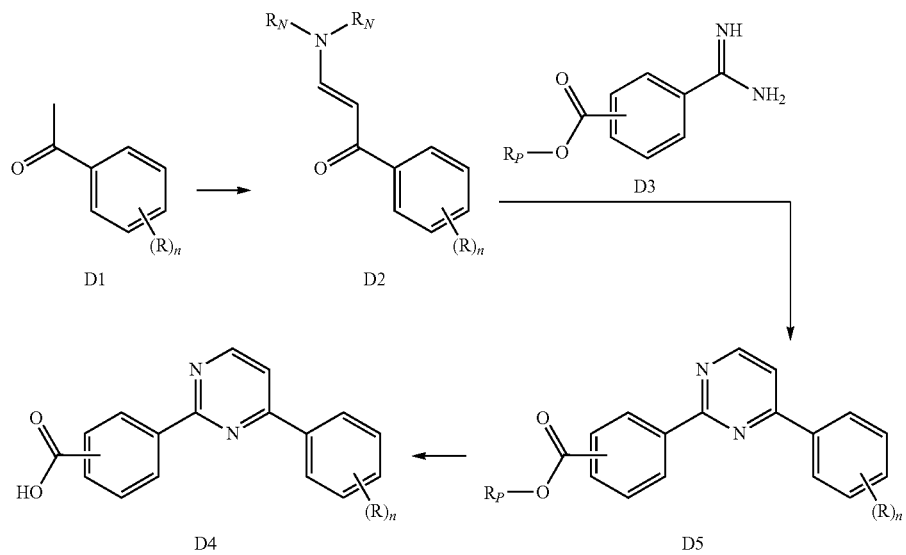

The acetophenone of Formula D1 may be used to prepare the aminoacryloyl compound of Formula D2, which may then be condensed with the amidine reagent of Formula D3 (the synthesis of which was discussed above) to yield the pyrimidine of Formula D4. As before, the protected carboxylate may then be used to liberate the free carboxylate group if desired in the compound of Formulas 1-D and 2-D.

An aryl cross-coupling approach similar to that of Scheme C above may be used to prepare pyridine compounds of Formulas 1-E and 2-E (see Scheme E, below).

Scheme E

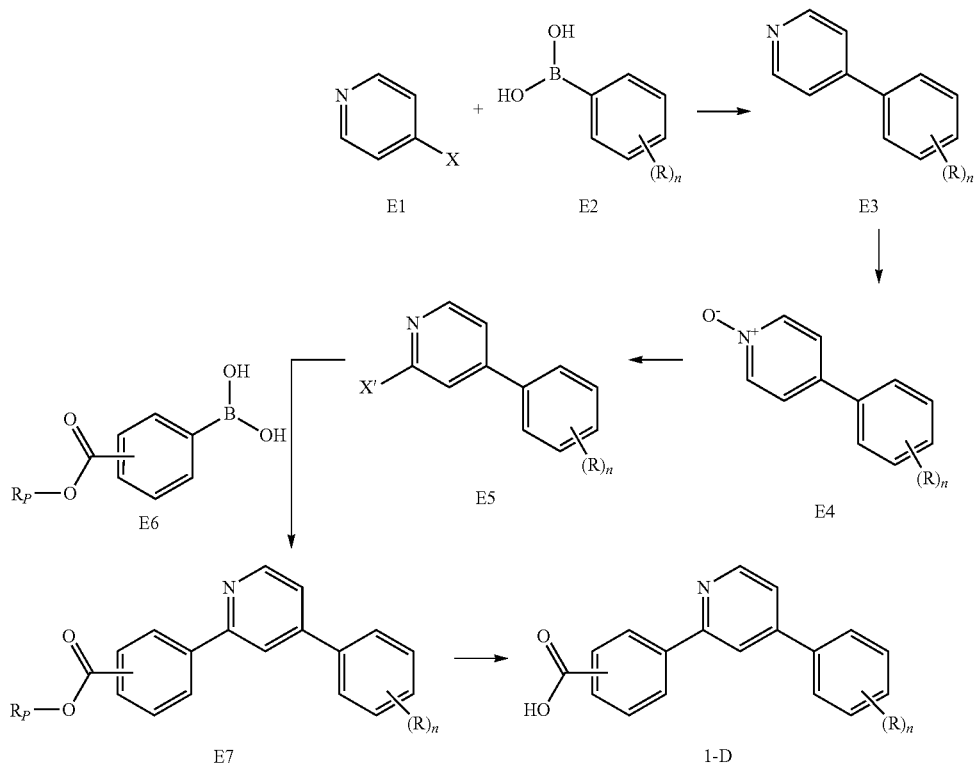

A pyridine reagent of Formula E1 may serve as the starting material, wherein X represents a group that can be displaced in aryl cross-coupling reactions, such as chloro, bromo, iodo or trifluoromethanesulfonyl. The coupling reaction may be performed with a reagent such as the boronic acid of Formula E2. In the event that the compound of Formula E2 is not available from commercial sources, they may be prepared by metal-halogen exchange (of a bromo or iodo with lithium, magnesium, zinc, etc.) followed by quenching with a source of boron, such as trimethylborate or triisopropylborate. The cross-coupling reaction may be catalyzed by compounds such as tetrakis(triphenylphosphine), palladium acetate or bis(triphenylphosphine)palladium dichloride optionally with the addition of a phosphine ligand such as triphenylphosphine, BINAP, etc. The reaction may also require the presence of a base such as sodium carbonate, potassium triphosphate or cesium fluoride. Appropriate solvents for the Suzuki-type cross-coupling reaction include ethanol, toluene, 1,4-dioxane or glyme, and the reaction proceeds preferentially in the absence of oxygen, so the solvent should be degassed.

Once obtaining the pyridine compound of Formula E3, the nitrogen atom may oxidized to the pyridine N-oxide compound of Formula E4. Reagents for this conversion include m-chloroperbenzoic acid or hydrogen peroxide (plus various additives). The oxide may then be subjected to a rearrangement reaction to yield the compound of Formula E5. Reagents for this conversion include phosphorus oxychloride, phosphorus tribromide or trimethylsilyl trifluoromethanesulfonate. The X' group represents a halogen or pseudohalogen (Cl, Br, OTf) and will depend on the pyridine oxide-activation reaction conditions and reagents employed. If the reaction affords the 2-pyridone, this can easily be converted to the 2-X'-pyridine; for example, pyridones react with phosphorus oxychloride to afford 2-chloropyridines. The 2-halopyridine may then be employed in a cross-coupling reaction with the boronic acid compound of Formula E6 using the Suzuki-type palladium-catalyzed reaction described above to afford the 2,4-diarylpyridine compound of Formula E7. The carboxylate may then be deprotected as before if desired to yield the final product of Formulas 1-E and 2-E.

Another double cross-coupling approach similar that that of Scheme E above may be used for the synthesis of pyridine compounds of Formulas 1-F and 2-F (Scheme F).

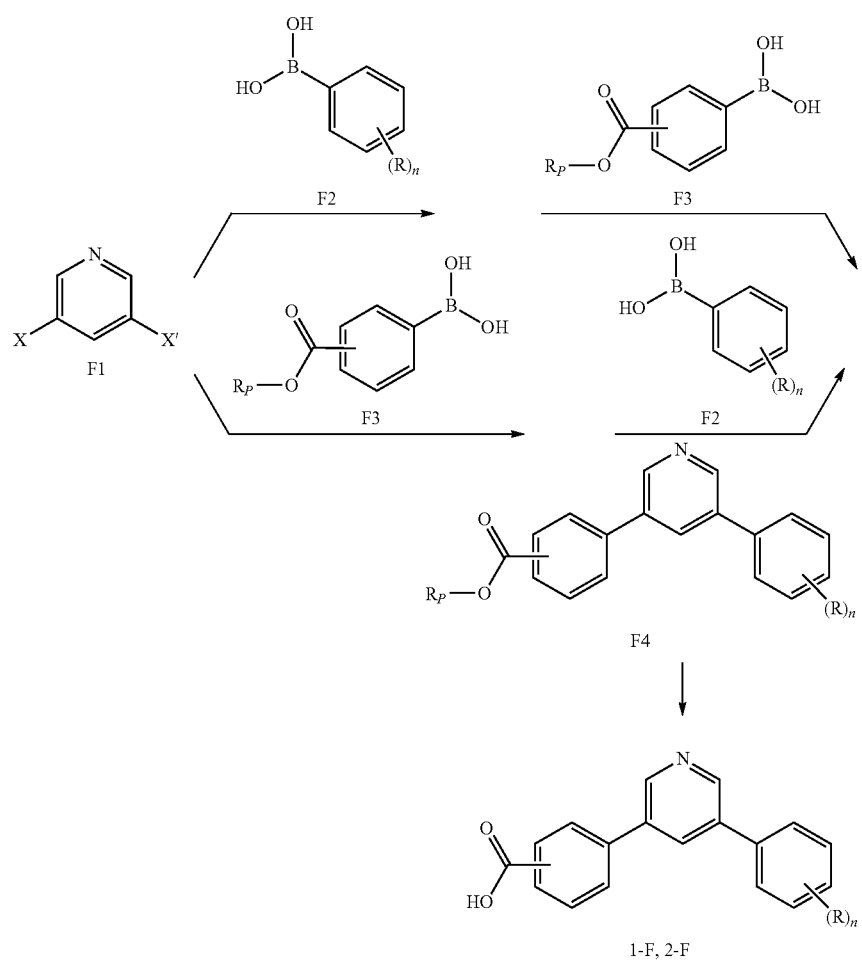

A 3,5-dihalopyridine of Formula F1 is used in sequential Suzuki reactions with the boronic acid derivatives of the two aryl groups (Formulae F2 and F3). The isolation of the intermediate mono-coupled compound may be advantageous in terms of final product purification. To improve selectivity for this overall transformation, it may be desirable to use a substrate with different halogens (i.e. X≠X'). Another approach may involve using an X' group which is a masked halogen; for example, an aryl amino group can be converted to halogen via diazotization followed by displacement by halogen. As before, catalysts for the coupling reaction are mostly Pd(0) or Pd(2)-based. Also, the carboxylate protecting group may be removed if desired at the final step to give the final product of Formulas 1-F and 2-F.

Pyridine compounds of Formulas 1-G and 2-G (Scheme G) may be prepared in a fashion analogous to the synthesis of the regioisomer of Formulas 1-F and 2-F (Scheme F).

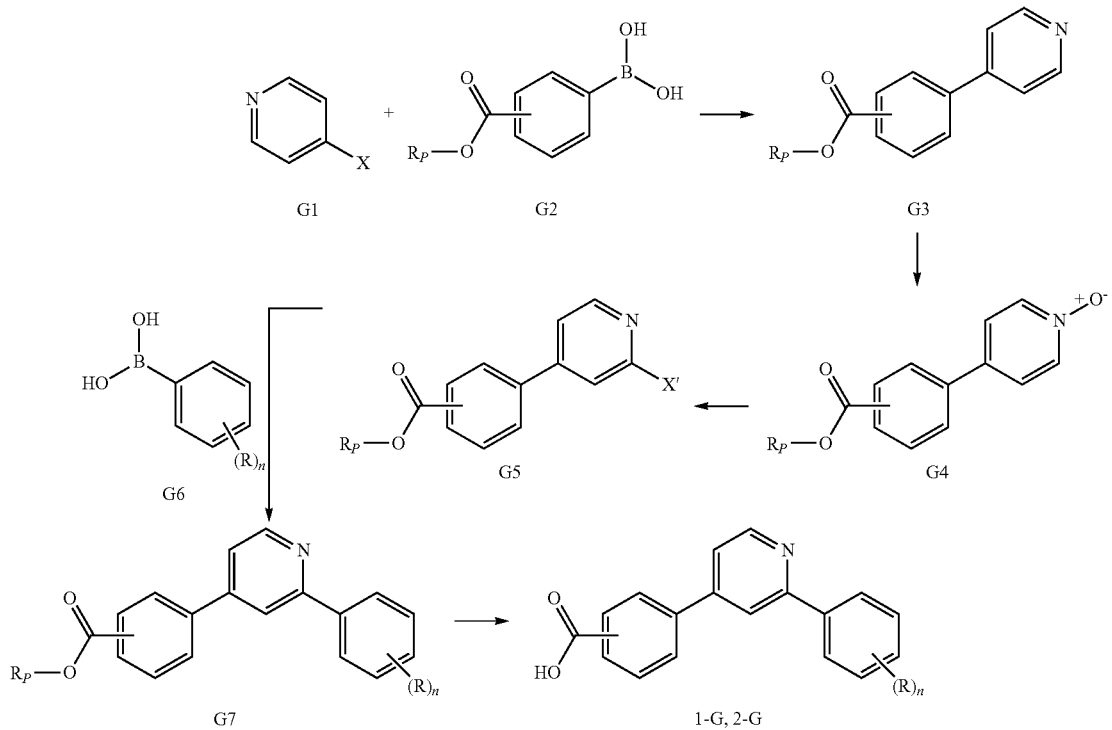

The method of preparation of the pyridine 3,5-isomer of Formulas 1-G and 2-G (Scheme G) can be used for the 2,6-isomer of Formulas 1-H and 2-H (Scheme H). As before, the two coupling reactions may be performed in either order, depending on which is more convenient.

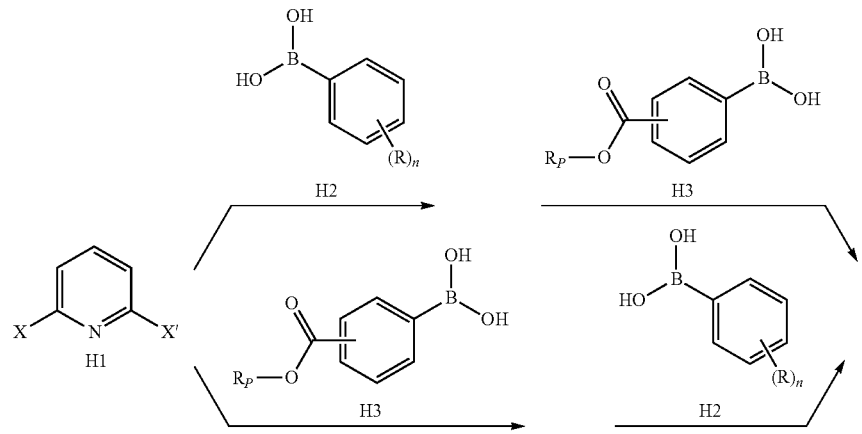

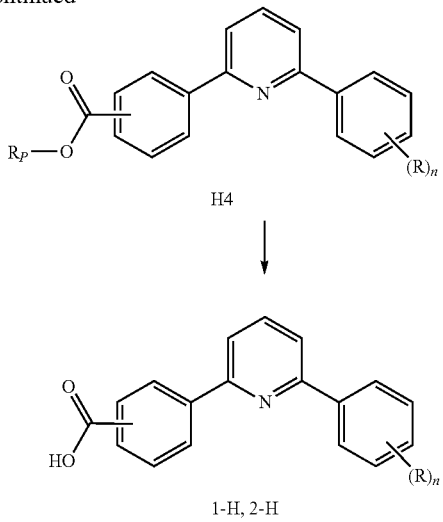

In certain preferred embodiments, compounds of the invention may be resolved to enantiomerically pure compositions or synthesized as enantiomerically pure compositions using any method known in art. By way of example, compounds of the invention may be resolved by direct crystallization of enantiomer mixtures, by diastereomer salt formation of enantiomers, by the formation and separation of diastereomers or by enzymatic resolution of a racemic mixture.

These and other reaction methodologies may be useful in preparing the compounds of the invention, as recognized by one of skill in the art. Various modifications to the above schemes and procedures will be apparent to one of skill in the art, and the invention is not limited specifically by the method of preparing the compounds of the invention.

C. Methods of the Invention

In another aspect of the invention, methods are provided for the suppression of premature translation termination, which may be associated with a nonsense mutation, and for the prevention or treatment of diseases. In a preferred embodiment, such diseases are associated with mutations of mRNA, especially nonsense mutations. Exemplary diseases include, but are not limited to, cancer, lysosomal storage disorders, the muscular dystrophies, cystic fibrosis, hemophilia, epidermolysis bullosa and classical late infantile neuronal ceroid lipofuscinosis. In this embodiment, methods for treating cancer, lysosomal storage disorders, a muscular dystrophy, cystic fibrosis, hemophilia, or classical late infantile neuronal ceroid lipofuscinosis are provided comprising administering a therapeutically effective amount of at least one compound of the invention to a subject in need thereof.

In one embodiment, the present invention is directed to methods for increasing the expression of one or more specific, functional proteins. Any compound of the invention can be used to specifically increase expression of functional protein. In another embodiment, a specific increase in expression of functional protein occurs when premature translation termination is suppressed by administering a therapeutically effective amount of at least one compound of the invention to a subject in need thereof. In a preferred embodiment premature translation termination is associated with a nonsense mutation in mRNA. In another embodiment, a specific increase in expression of functional protein occurs when mRNA decay is reduced in a patient. In a preferred embodiment, the abnormality in a patient is caused by mutation-mediated mRNA decay. In a particularly preferred embodiment, mutation-mediated mRNA decay is the result of a nonsense mutation. The methods of the present invention are not limited by any particular theory.

The invention encompasses methods of treating and preventing diseases or disorders ameliorated by the suppression of premature translation termination, nonsense-mediated mRNA decay, or premature translation termination and nonsense-mediated mRNA decay in a patient which comprise administering to a patient in need of such treatment or prevention a therapeutically effective amount of a compound of the invention.

In one embodiment, the present invention encompasses the treatment or prevention of any disease that is associated with a gene exhibiting premature translation termination, nonsense-mediated mRNA decay, or premature translation termination and nonsense-mediated mRNA decay. In one embodiment, the disease is due, in part, to the lack of or reduced expression of the gene resulting from a premature stop codon. Specific examples of genes which may exhibit premature translation termination and/or nonsense-mediated mRNA decay and diseases associated with premature translation termination and/or nonsense-mediated mRNA decay are found in U.S. Provisional Patent Application No. 60/390,747, titled: Methods For Identifying Small Molecules That Modulate Premature Translation Termination And Nonsense Mediated mRNA Decay, filed Jun. 21, 2002, and International Application PCT/US03/19760, filed Jun. 23, 2003, both of which are incorporated herein by reference in their entirety.

Diseases ameliorated by the suppression of premature translation termination, nonsense-mediated mRNA decay, or premature translation termination and nonsense-mediated mRNA decay include, but are not limited to: genetic diseases, somatic diseases, cancers, autoimmune diseases, blood diseases, collagen diseases, diabetes, neurodegenerative diseases, proliferative diseases, cardiovascular diseases, pulmonary diseases, inflammatory diseases or central nervous system diseases.

In one embodiment, diseases to be treated or prevented by administering to a patient in need thereof an effective amount of a compound of the invention include, but are not limited to, amyloidosis, hemophilia, Alzheimer's disease, Tay Sachs disease, Niemann Pick disease, atherosclerosis, giantism, dwarfism, hypothyroidism, hyperthyroidism, aging, obesity, Parkinson's disease, cystic fibrosis, muscular dystrophy, heart disease, kidney stones, ataxia-telangiectasia, familial hypercholesterolemia, retinitis pigmentosa, Duchenne muscular dystrophy, epidermolysis bullosa and Marfan syndrome. In one embodiment, the diseases are associated with a nonsense mutation.

In one embodiment, the compounds of the invention are useful for treating or preventing an autoimmune disease. In one embodiment, the autoimmune disease is associated with a nonsense mutation. In a preferred embodiment, the autoimmune disease is rheumatoid arthritis or graft versus host disease.

In another embodiment, the compounds of the invention are useful for treating or preventing a blood disease. In one embodiment, the blood disease is associated with a nonsense mutation. In a preferred embodiment, the blood disease is hemophilia, Von Willebrand disease, ataxia-telangiectasia, β-thalassemia or kidney stones.

In another embodiment, the compounds of the invention are useful for treating or preventing a collagen disease. In one embodiment, the collagen disease is associated with a nonsense mutation. In a preferred embodiment, the collagen disease is osteogenesis imperfecta or cirrhosis.

In another embodiment, the compounds of the invention are useful for treating or preventing diabetes. In one embodiment, the diabetes is associated with a nonsense mutation.

In another embodiment, the compounds of the invention are useful for treating or preventing an inflammatory disease. In one embodiment, the inflammatory disease is associated with a nonsense mutation. In a preferred embodiment, the inflammatory disease is arthritis, rheumatoid arthritis or osteoarthritis.

In another embodiment, the compounds of the invention are useful for treating or preventing a central nervous system disease. In one embodiment, the central nervous system disease is associated with a nonsense mutation. In one embodiment, the central nervous system disease is a neurodegenerative disease. In a preferred embodiment, the central nervous system disease is multiple sclerosis, muscular dystrophy, Duchenne muscular dystrophy, Alzheimer's disease, Tay Sachs disease, Niemann Pick disease, late infantile neuronal ceroid lipofuscinosis (LINCL) or Parkinson's disease.

In another preferred embodiment, the compounds of the invention are useful for treating or preventing cancer, particularly in humans. In a preferred embodiment, the cancer is of the head and neck, eye, skin, mouth, throat, esophagus, chest, bone, blood, lung, colon, sigmoid, rectum, stomach, prostate, breast, ovaries, kidney, liver, pancreas, brain, intestine, heart or adrenals. In one embodiment, the cancer is a solid tumor. In one embodiment, the cancer is associated with a nonsense mutation. In another embodiment, the cancer is associated with a genetic nonsense mutation. In another embodiment, the cancer is associated with a somatic mutation. Without being limited by any theory, the use of the compounds of the invention against cancer may relate to its action against mutations of the p53 gene.

In one embodiment, the cancer is not a blood cancer. In another embodiment, the cancer is not leukemia. In another embodiment, the cancer is not multiple myeloma. In another embodiment, the cancer is not prostate cancer.

In another preferred embodiment, the compounds of the invention are useful for treating or preventing cancer associated with a mutation of tumor suppressor gene. Such genes include, but are not limited to PTEN, BRCA1, BRCA2, Rb, and the p53 gene. In one embodiment, the mutation is a genetic mutation. In another embodiment, the mutation is a somatic mutation. The methods of the invention are particularly useful for treating or preventing a cancer associated with a nonsense mutation in the in a tumor suppressor gene. In a preferred embodiment, the methods of the invention are particularly useful for treating or preventing a cancer associated with a p53 gene due to the role of p53 in apoptosis. Without being limited by theory, it is thought that apoptosis can be induced by contacting a cell with an effective amount of a compound of the invention resulting in suppression of the nonsense mutation, which, in turn, allows the production of full-length p53 to occur. Nonsense mutations have been identified in the p53 gene and have been implicated in cancer. Several nonsense mutations in the p53 gene have been identified (see, e.g., Masuda et al., 2000, Tokai J Exp Clin Med. 25(2):69-77; Oh et al., 2000, Mol Cells 10(3):275-80; Li et al., 2000, Lab Invest. 80(4):493-9; Yang et al., 1999, Zhonghua Zhong Liu Za Zhi 21(2):114-8; Finkelstein et al., 1998, Mol Diagn. 3(1):37-41; Kajiyama et al., 1998, Dis Esophagus. 11(4):279-83; Kawamura et al., 1999, Leuk Res. 23(2): 115-26; Radig et al., 1998, Hum Pathol. 29(11):1310-6; Schuyer et al., 1998, Int J Cancer 76(3):299-303; Wang-Gohrke et al., 1998, Oncol Rep. 5(1):65-8; Fulop et al., 1998, J Reprod Med. 43(2):119-27; Ninomiya et al., 1997, J Dermatol Sci. 14(3):173-8; Hsieh et al., 1996, Cancer Lett. 100 (1-2):107-13; Rall et al., 1996, Pancreas. 12(1):10-7; Fukutomi et al., 1995, Nippon Rinsho. 53(11):2764-8; Frebourg et al., 1995, Am J Hum Genet. 56(3):608-15; Dove et al., 1995, Cancer Surv. 25:335-55; Adamson et al., 1995, Br J Haematol. 89(1):61-6; Grayson et al., 1994, Am J Pediatr Hematol Oncol. 16(4):341-7; Lepelley et al., 1994, Leukemia. 8(8): 1342-9; McIntyre et al., 1994, J Clin Oncol. 12(5):925-30; Horio et al., 1994, Oncogene. 9(4):1231-5; Nakamura et al., 1992, Jpn J Cancer Res. 83(12):1293-8; Davidoff et al., 1992, Oncogene. 7(1):127-33; and Ishioka et al., 1991, Biochem Biophys Res Commun. 177(3):901-6; the disclosures of which are hereby incorporated by reference herein in their entireties). Any disease associated with a p53 gene encoding a premature translation codon including, but not limited to, the nonsense mutations described in the references cited above, can be treated or prevented by compounds of the invention.

In other embodiments, diseases to be treated or prevented by administering to a patient in need thereof an effective amount of a compound of the invention include, but are not limited to, solid tumors such as sarcoma, carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, Kaposi's sarcoma, pinealoma, hemangioblastoma, acoustic neuroma, oligodendroglioma, menangioma, melanoma, neuroblastoma, retinoblastoma, a blood-born tumor or multiple myeloma.

In another embodiment, diseases to be treated or prevented by administering to a patient in need thereof an effective amount of a compound of the invention include, but are not limited to, a blood-born tumor such as acute lymphoblastic leukemia, acute lymphoblastic B-cell leukemia, acute lymphoblastic T-cell leukemia, acute myeloblastic leukemia, acute promyelocytic leukemia, acute monoblastic leukemia, acute erythroleukemic leukemia, acute megakaryoblastic leukemia, acute myelomonocytic leukemia, acute nonlymphocyctic leukemia, acute undifferentiated leukemia, chronic myelocytic leukemia, chronic lymphocytic leukemia, hairy cell leukemia, or multiple myeloma. See e.g., Harrison's Principles of Internal Medicine, Eugene Braunwald et al., eds., pp. 491-762 (15th ed. 2001).

In yet another embodiment, the invention encompasses the treatment of a human afflicted with a solid tumor or a blood tumor.

In a preferred embodiment, the invention encompasses a method of treating or preventing a disease ameliorated by modulation of premature translation termination, nonsense-mediated mRNA decay, or premature translation termination and nonsense-mediated mRNA decay, or ameliorating one or more symptoms associated therewith comprising contacting a cell with a therapeutically effective amount of a compound of the invention. Cells encompassed by the present methods include animal cells, mammalian cells, bacterial cells, and virally infected cells. In one embodiment, the nonsense mutation is a genetic mutation (i.e., the nonsense codon was present in the progenitor DNA). In another embodiment, the nonsense mutation is a somatic mutation (i.e., the nonsense codon arose spontaneously or from mutagenesis).

In certain embodiments, a compound of the invention is administered to a subject, including but not limited to a plant, reptile, avian, amphibian or preferably a mammal, more preferably a human, as a preventative measure against a disease associated with premature translation termination, nonsense-mediated mRNA decay, or premature translation termination and nonsense-mediated mRNA decay.

In a preferred embodiment, it is first determined that the patient is suffering from a disease associated with premature translation termination and/or nonsense-mediated mRNA decay. In another embodiment, the patient has undergone a screening process to determine the presence of a nonsense mutation comprising the steps of screening a subject, or cells extracted therefrom, by an acceptable nonsense mutation screening assay. In a preferred embodiment, the DNA of the patient can be sequenced or subjected to Southern Blot, polymerase chain reaction (PCR), use of the Short Tandem Repeat (STR), or polymorphic length restriction fragments (RFLP) analysis to determine if a nonsense mutation is present in the DNA of the patient. In one embodiment, it is determined whether the nonsense mutation is a genetic mutation or a somatic mutation by comparison of progenitor DNA. Alternatively, it can be determined if altered levels of the protein with the nonsense mutation are expressed in the patient by western blot or other immunoassays. In another embodiment, the patient is an unborn child who has undergone screening in utero for the presence of a nonsense mutation. Administration of a compound of the invention can occur either before or after birth. In a related embodiment, the therapy is personalized in that the patient is screened for a nonsense mutation screening assay and treated by the administration of one or more compounds of the invention; particularly, the patient may be treated with a compound particularly suited for the mutations in question; e.g., depending upon the disease type, cell type, and the gene in question. Such methods are well known to one of skill in the art.

In another embodiment, the cells (e.g., animal cells, mammalian cells, bacterial cells, plant cells and virally infected cells) are screened for premature translation termination and/or nonsense-mediated mRNA decay with a method such as that described above (i.e., the DNA of the cell can be sequenced or subjected to Southern Blot, polymerase chain reaction (PCR), use of the Short Tandem Repeat (STR), or polymorphic length restriction fragments (RFLP) analysis to determine if a nonsense mutation is present in the DNA of the cell; the RNA of the cell can be subjected to quantitative real time PCR to determine transcript abundance).

Specific methods of the invention further comprise the administration of an additional therapeutic agent (i.e., a therapeutic agent other than a compound of the invention). In certain embodiments of the present invention, the compounds of the invention can be used in combination with at least one other therapeutic agent. Therapeutic agents include, but are not limited to non-opioid analgesics; non-steroid anti-inflammatory agents; steroids, antiemetics; β-adrenergic blockers; anticonvulsants; antidepressants; $Ca^{2+}$-channel blockers; anticancer agent(s) and antibiotics and mixtures thereof.

In certain embodiments, the compounds of the invention can be administered or formulated in combination with anticancer agents. Suitable anticancer agents include, but are not limited to: alkylating agents; nitrogen mustards; folate antagonists; purine antagonists; pyrimidine antagonists; spindle poisons; topoisomerase inhibitors; apoptosis inducing agents; angiogenesis inhibitors; podophyllotoxins; nitrosoureas; cisplatin; carboplatin; interferon; asparginase; tamoxifen; leuprolide; flutamide; megestrol; mitomycin; bleomycin; doxorubicin; irinotecan and taxol.

In certain embodiments, the compounds of the invention can be administered or formulated in combination with antibiotics. In certain embodiments, the antibiotic is an aminoglycoside (e.g., tobramycin), a cephalosporin (e.g., cephalexin, cephradine, cefuroxime, cefprozil, cefaclor, cefixime or cefadroxil), a clarithromycin (e.g., clarithromycin), a macrolide (e.g., erythromycin), a penicillin (e.g., penicillin V) or a quinolone (e.g., ofloxacin, ciprofloxacin or norfloxacin). In a preferred embodiment, the antibiotic is active against *Pseudomonas aeruginosa*.

Without intending to be limited by theory, it is believed that the methods of the present invention act through a combination of mechanisms that suppress nonsense mutations. In preferred embodiments, the methods of the invention comprise administering a therapeutically effective amount of at least one compound of the invention, e.g., a compound of Formula 1. Relative activity of the compounds of the invention may be determined by any method known in the art, including the assay described in Example 2 herein.

Compounds of the invention can be characterized with an in vitro luciferase nonsense suppression assay. Luciferase assays are included in the methods of the present invention. Luciferase can be used as a functional reporter gene assay (light is only produced if the protein is functional), and luciferase is extremely sensitive (Light intensity is proportional to luciferase concentration in the nM range). In one embodiment, an assay of the present invention is a cell-based luciferase reporter assay. In a preferred cell-based luciferase reporter assay, a luciferase reporter construct containing a premature termination codon (UGA, UAA, or UAG) is stably transfected in 293 Human Embryonic Kidney cells.

In another assay of the present invention, a preferred assay is a biochemical assay consisting of rabbit reticulocyte lysate and a nonsense-containing luciferase reporter mRNA. In another assay of the present invention, the assay is a biochemical assay consisting of prepared and optimized cell extract (Lie & Macdonald, 1999, Development 126(22): 4989-4996 and Lie & Macdonald, 2000, Biochem. Biophys.

Res. Commun. 270(2):473-481. In the biochemical assay, mRNA containing a premature termination codon (UGA, UAA, or UAG) is used as a reporter in an in vitro translation reaction using rabbit reticulocyte lysate supplemented with tRNA, hemin, creatine kinase, amino acids, KOAc, Mg(OAc)2, and creatine phosphate. Translation of the mRNA is initiated within a virus derived leader sequence, which significantly reduces the cost of the assay because capped RNA is not required. Synthetic mRNA is prepared in vitro using the T7 promoter and the MegaScript in vitro transcription kit (Ambion, Inc.; Austin, Tex.). In assays of the present invention, addition of gentamicin, an aminoglycoside known to allow readthrough of premature termination codons, results in increased luciferase activity and can be used as an internal standard. Assays of the present invention can be used in high-throughput screens. Hundreds of thousands of compounds can be screened in cell-based and biochemical assays of the present invention. In a preferred aspect, a functional cell-based assay similar to the one described.

Compounds of the present invention include compounds capable of increasing specific, functional protein expression from mRNA molecules comprising premature termination codons. In one embodiment, compounds of the present invention can preferentially suppress premature translation termination. For example, a compound of the present invention can be capable of suppressing a nonsense mutation if the mutation results in UAA, but not capable of suppressing a nonsense mutation if the mutation results in UAG. Another non-limiting example can occur when a compound of the present invention can be capable of suppressing a nonsense mutation if the mutation results in UAA and is followed, in-frame by a cytosine at the +1 position, but not capable of suppressing a nonsense mutation if the mutation results in UAA and is followed, in-frame by an adenine at the +1 position.

A stable cell line harboring the UGA nonsense-containing luciferase gene can be treated with a test compound. In this aspect, cells can be grown in standard medium supplemented with 1% penicillin-streptomycin (P/S) and 10% fetal bovine serum (FBS) to 70% confluency and split 1:1 the day before treatment. The next day, cells are trypsinized and 40,000 cells are added to each well of a 96-well tissue culture dish. Serial dilutions of each compound are prepared to generate a six-point dose response curve spanning 2 logs (30 µM to 0.3 µM). The final concentration of the DMSO solvent remains constant at 1% in each well. Cells treated with 1% DMSO serve as the background standard, and cells treated with gentamicin serve as a positive control.

To address the effects of the nonsense-suppressing compounds on mRNAs altered in specific inherited diseases, a bronchial epithelial cell line harboring a nonsense codon at amino acid 1282 (W1282X) can be treated with a compound of the invention and CFTR function is monitored as a cAMP-activated chloride channel using the SPQ assay (Yang et al., Hum. Mol. Genet. 2(8):1253-1261 (1993) and Howard et al., Nat. Med. 2(4):467-469(1996)). The increase in SPQ fluorescence in cells treated with a compound of the invention is compared to those treated with cAMP and untreated cells. An increase in SPQ fluorescence in cells is consistent with stimulation of CFTR-mediated halide efflux and an increase in readthrough of the nonsense codon. Full-length CFTR expression from this nonsense-containing allele following treatment with a compound of the invention demonstrates that cystic fibrosis cell lines increase chloride channel activity when treated with a compound of the invention.

D. Metabolites of the Compounds of the Invention

Also falling within the scope of the present invention are the in vivo metabolic products of the compounds described herein. Such products may result for example from the oxidation, reduction, hydrolysis, amidation, esterification and the like of the administered compound, primarily due to enzymatic processes. Accordingly, the invention includes compounds produced by a process comprising contacting a compound of this invention with a mammalian tissue or a mammal for a period of time sufficient to yield a metabolic product thereof. Such products typically are identified by preparing a radio-labeled (e.g. $C^{14}$ or $H^3$) compound of the invention, administering it in a detectable dose (e.g., greater than about 0.5 mg/kg) to a mammal such as rat, mouse, guinea pig, monkey, or to man, allowing sufficient time for metabolism to occur (typically about 30 seconds to 30 hours), and isolating its conversion products from urine, blood or other biological samples. These products are easily isolated since they are labeled (others are isolated by the use of antibodies capable of binding epitopes surviving in the metabolite). The metabolite structures are determined in conventional fashion, e.g., by MS or NMR analysis. In general, analysis of metabolites may be done in the same way as conventional drug metabolism studies well-known to those skilled in the art. The conversion products, so long as they are not otherwise found in vivo, are useful in diagnostic assays for therapeutic dosing of the compounds of the invention even if they possess no biological activity of their own.

E. Pharmaceutical Compositions of the Invention

While it is possible for the compounds of the present invention to be administered neat, it may be preferable to formulate the compounds as pharmaceutical compositions. As such, in yet another aspect of the invention, pharmaceutical compositions useful in the methods of the invention are provided. The pharmaceutical compositions of the invention may be formulated with pharmaceutically acceptable excipients such as carriers, solvents, stabilizers, adjuvants, diluents, etc., depending upon the particular mode of administration and dosage form. The pharmaceutical compositions should generally be formulated to achieve a physiologically compatible pH, and may range from a pH of about 3 to a pH of about 11, preferably about pH 3 to about pH 7, depending on the formulation and route of administration. In another embodiment, the pH of a pharmaceutical composition of the present invention may be adjusted to a range from about pH 4 to about pH 7. In alternative embodiments, it may be preferred that the pH is adjusted to a range from about pH 5 to about pH 8.

More particularly, the pharmaceutical compositions of the invention comprise a therapeutically or prophylactically effective amount of at least one compound of the present invention, together with one or more pharmaceutically acceptable excipients. Optionally, the pharmaceutical compositions of the invention may comprise a combination of compounds of the present invention, or may include a second active ingredient useful in the treatment of cancer, diabetic retinopathy, or exudative macular degeneration.

Formulations of the present invention, e.g., for parenteral or oral administration, are most typically solids, liquid solutions, emulsions or suspensions, while inhalable formulations for pulmonary administration are generally liquids or powders, with powder formulations being generally preferred. A preferred pharmaceutical composition of the invention may also be formulated as a lyophilized solid that is reconstituted with a physiologically compatible solvent prior to administration. Alternative pharmaceutical compositions of the invention may be formulated as syrups, creams, ointments, tablets, and the like.

The pharmaceutical compositions of the invention can be administered to the subject via any drug delivery route known in the art. Specific exemplary administration routes include oral, ocular, rectal, buccal, topical, nasal, ophthalmic, subcutaneous, intramuscular, intraveneous (bolus and infusion), intracerebral, transdermal, and pulmonary.

The term "pharmaceutically acceptable excipient" refers to an excipient for administration of a pharmaceutical agent, such as the compounds of the present invention. The term refers to any pharmaceutical excipient that may be administered without undue toxicity. Pharmaceutically acceptable excipients are determined in part by the particular composition being administered, as well as by the particular method used to administer the composition. Accordingly, there exists a wide variety of suitable formulations of pharmaceutical compositions of the present invention (see, e.g., Remington's Pharmaceutical Sciences, 18$^{th}$ Ed., Mack Publishing Co., 1990).

Suitable excipients may be carrier molecules that include large, slowly metabolized macromolecules such as proteins, polysaccharides, polylactic acids, polyglycolic acids, polymeric amino acids, amino acid copolymers, and inactive virus particles. Other exemplary excipients include antioxidants such as ascorbic acid; chelating agents such as EDTA; carbohydrates such as dextrin, hydroxyalkylcellulose, hydroxyalkylmethylcellulose, stearic acid; liquids such as oils, water, saline, glycerol and ethanol; wetting or emulsifying agents; pH buffering substances; and the like. Liposomes are also included within the definition of pharmaceutically acceptable excipients.

The pharmaceutical compositions of the invention may be formulated in any form suitable for the intended method of administration. When intended for oral use for example, tablets, troches, lozenges, aqueous or oil suspensions, non-aqueous solutions, dispersible powders or granules (including micronized particles or nanoparticles), emulsions, hard or soft capsules, syrups or elixirs may be prepared. Compositions intended for oral use may be prepared according to any method known to the art for the manufacture of pharmaceutical compositions, and such compositions may contain one or more agents including sweetening agents, flavoring agents, coloring agents and preserving agents, in order to provide a palatable preparation.

Pharmaceutically acceptable excipients particularly suitable for use in conjunction with tablets include, for example, inert diluents, such as celluloses, calcium or sodium carbonate, lactose, calcium or sodium phosphate; disintegrating agents, such as croscarmellose sodium, cross-linked povidone, maize starch, or alginic acid; binding agents, such as povidone, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example celluloses, lactose, calcium phosphate or kaolin, or as soft gelatin capsules wherein the active ingredient is mixed with non-aqueous or oil medium, such as glycerin, propylene glycol, polyethylene glycol, peanut oil, liquid paraffin or olive oil.

In another embodiment, pharmaceutical compositions of the invention may be formulated as suspensions comprising a compound of the present invention in admixture with at least one pharmaceutically acceptable excipient suitable for the manufacture of a suspension. In yet another embodiment, pharmaceutical compositions of the invention may be formulated as dispersible powders and granules suitable for preparation of a suspension by the addition of suitable excipients.

Excipients suitable for use in connection with suspensions include suspending agents, such as sodium carboxymethylcellulose, methylcellulose, hydroxypropyl methylcelluose, sodium alginate, polyvinylpyrrolidone, gum tragacanth, gum acacia, dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycethanol), a condensation product of ethylene oxide with a partial ester derived from a fatty acid and a hexitol anhydride (e.g., polyoxyethylene sorbitan monooleate); and thickening agents, such as carbomer, beeswax, hard paraffin or cetyl alcohol. The suspensions may also contain one or more preservatives such as acetic acid, methyl and/or n-propyl p-hydroxy-benzoate; one or more coloring agents; one or more flavoring agents; and one or more sweetening agents such as sucrose or saccharin.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth; naturally occurring phosphatides, such as soybean lecithin, esters or partial esters derived from fatty acids; hexitol anhydrides, such as sorbitan monooleate; and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

Additionally, the pharmaceutical compositions of the invention may be in the form of a sterile injectable preparation, such as a sterile injectable aqueous emulsion or oleaginous suspension. This emulsion or suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,2-propane-diol. The sterile injectable preparation may also be prepared as a lyophilized powder. Among the acceptable vehicles and solvents that may be employed are water, Ringer's solution, and isotonic sodium chloride solution. In addition, sterile fixed oils may be employed as a solvent or suspending medium. For this purpose any bland fixed oil may be employed including synthetic mono- or diglycerides. In addition, fatty acids such as oleic acid may likewise be used in the preparation of injectables.

Generally, the compounds of the present invention useful in the methods of the present invention are substantially insoluble in water and are sparingly soluble in most pharmaceutically acceptable protic solvents and in vegetable oils. However, the compounds are generally soluble in medium chain fatty acids (e.g., caprylic and capric acids) or triglycerides and have high solubility in propylene glycol esters of medium chain fatty acids. Also contemplated in the invention are compounds which have been modified by substitutions or additions of chemical or biochemical moieties which make them more suitable for delivery (e.g., increase solubility, bioactivity, palatability, decrease adverse reactions, etc.), for example by esterification, glycosylation, PEGylation, etc.

In a preferred embodiment, the compounds of the present invention may be formulated for oral administration in a lipid-based formulation suitable for low solubility compounds. Lipid-based formulations can generally enhance the oral bioavailability of such compounds. As such, a preferred pharmaceutical composition of the invention comprises a therapeutically or prophylactically effective amount of a compound of the present invention, together with at least one pharmaceutically acceptable excipient selected from the group consisting of medium chain fatty acids or propylene glycol esters thereof (e.g., propylene glycol esters of edible fatty acids such as caprylic and capric fatty acids) and pharmaceutically acceptable surfactants such as polyoxyl 40 hydrogenated castor oil.

In an alternative preferred embodiment, cyclodextrins may be added as aqueous solubility enhancers. Preferred cyclodextrins include hydroxypropyl, hydroxyethyl, glucosyl, maltosyl and maltotriosyl derivatives of α-, β-, and γ-cyclodextrin. A particularly preferred cyclodextrin solubility enhancer is hydroxypropyl-β-cyclodextrin (HPBC), which may be added to any of the above-described compositions to further improve the aqueous solubility characteristics of the compounds of the present invention. In one embodiment, the composition comprises 0.1% to 20% hydroxypropyl-β-cyclodextrin, more preferably 1% to 15% hydroxypropyl-3-cyclodextrin, and even more preferably from 2.5% to 10% hydroxypropyl-β-cyclodextrin. The amount of solubility enhancer employed will depend on the amount of the compound of the present invention in the composition.

The therapeutically effective amount, as used herein, refers to an amount of a pharmaceutical composition of the invention to treat, ameliorate, or modulate an identified disease or condition, or to exhibit a detectable therapeutic or inhibitory effect. The effect can be detected by, for example, assays of the present invention. The effect can also be the prevention of a disease or condition where the disease or condition is predicted for an individual or a high percentage of a population.

The precise effective amount for a subject will depend upon the subject's body weight, size, and health; the nature and extent of the condition; the therapeutic or combination of therapeutics selected for administration, the protein half-life, the mRNA half-life and the protein localization. Therapeutically effective amounts for a given situation can be determined by routine experimentation that is within the skill and judgment of the clinician.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The data obtained from cell culture assays and animal studies may be used in formulating a range of dosage for human use. The dosage contained in such compositions is preferably within a range of circulating concentrations that include an $ED_{50}$ with little or no toxicity. The dosage may vary within this range depending upon the dosage form employed, sensitivity of the patient, and the route of administration.

More specifically, the concentration-biological effect relationships observed with regard to the compound(s) of the present invention indicate an initial target plasma concentration ranging from approximately 5 μg/mL to approximately 100 μg/mL, preferably from approximately 10 μg/mL to approximately 50 μg/mL, more preferably from approximately 10 μg/mL to approximately 25 μg/mL. To achieve such plasma concentrations, the compounds of the invention may be administered at doses that vary from 1 mg/kg to 150 mg/kg, depending upon the route of administration. Guidance as to particular dosages and methods of delivery is provided in the literature and is generally available to practitioners in the art. In general the dose will be in the range of about 1 mg/day to about 10 g/day, or about 0.1 g to about 3 g/day, or about 0.3 g to about 3 g/day, or about 0.5 g to about 2 g/day, in single, divided, or continuous doses for a patient weighing between about 40 to about 100 kg (which dose may be adjusted for patients above or below this weight range, particularly children under 40 kg).

The magnitude of a prophylactic or therapeutic dose of a particular active ingredient of the invention in the acute or chronic management of a disease or condition will vary, however, with the nature and severity of the disease or condition, and the route by which the active ingredient is administered. The dose, and perhaps the dose frequency, will also vary according to the age, body weight, and response of the individual patient. Suitable dosing regimens can be readily selected by those skilled in the art with due consideration of such factors. In general, the recommended daily dose range for the conditions described herein lie within the range of from about 1 mg/kg to about 150 mg/kg per day. In one embodiment, the compound of the invention is given as a single once-a-day dose. In another embodiment, the compound of the invention is given as divided doses throughout a day. More specifically, the daily dose is administered in a single dose or in equally divided doses. Preferably, a daily dose range should be from about 5 mg/kg to about 100 mg/kg per day, more preferably, between about 10 mg/kg and about 90 mg/kg per day, even more preferably 20 mg/kg to 60 mg/kg per day. In managing the patient, the therapy should be initiated at a lower dose, perhaps about 200 mg to about 300 mg, and increased if necessary up to about 600 mg to about 4000 mg per day as either a single dose or divided doses, depending on the patient's global response. It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with individual patient response.

The phrases "therapeutically effective amount", "prophylactically effective amount" and "therapeutically or prophylactically effective amount," as used herein encompass the above described dosage amounts and dose frequency schedules. Different therapeutically effective amounts may be applicable for different diseases and conditions, as will be readily known by those of ordinary skill in the art. Similarly, amounts sufficient to treat or prevent such diseases, but insufficient to cause, or sufficient to reduce, adverse effects associated with conventional therapies are also encompassed by the above described dosage amounts and dose frequency schedules.

The exact dosage will be determined by the practitioner, in light of factors related to the subject that requires treatment. Dosage and administration are adjusted to provide sufficient levels of the active agent(s) or to maintain the desired effect. Factors which may be taken into account include the severity of the disease state, general health of the subject, age, weight, and gender of the subject, diet, time, protein of interest half-life, RNA of interest half-life, frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

F. Combination Therapy

It is also possible to combine any compound of the present invention with one or more other active ingredients useful in the treatment of diseases associated with nonsense mutations of mRNA as described herein, including compounds in a unitary dosage form, or in separate dosage forms intended for simultaneous or sequential administration to a patient in need of treatment. When administered sequentially, the combination may be administered in two or more administrations. In an alternative embodiment, it is possible to administer one or more compounds of the present invention and one or more additional active ingredients by different routes.

The skilled artisan will recognize that a variety of active ingredients may be administered in combination with the compounds of the present invention that may act to augment or synergistically enhance the nonsense mutation-suppressing activity of the compounds of the invention.

According to the methods of the invention, the combination of active ingredients may be: (1) co-formulated and administered or delivered simultaneously in a combined formulation; (2) delivered by alternation or in parallel as separate formulations; or (3) by any other combination therapy regimen known in the art. When delivered in alternation therapy, the methods of the invention may comprise administering or delivering the active ingredients sequentially, e.g., in separate solution, emulsion, suspension, tablets, pills or capsules, or by different injections in separate syringes. In general, during alternation therapy, an effective dosage of each active ingredient is administered sequentially, i.e., serially, whereas in simultaneous therapy, effective dosages of two or more active ingredients are administered together. Various sequences of intermittent combination therapy may also be used.

G. Gene Therapy

The compounds of the present invention or other nonsense compounds can be utilized in combination with gene therapy. In this embodiment, a gene can be introduced or provided to a mammal, preferably a human that contains a specified nonsense mutation in the desired gene. In a preferred aspect, the desired gene is selected from the group consisting of IGF1, EPO, p53, p19ARF, p21, PTEN, EI 24 and ApoAI. In order to obtain expression of the full-length polypeptide in a patient or mammal, the patient or mammal would be provided with an effective amount of a compound of the present invention or other nonsense compound when such polypeptide is desired.

There are two major approaches to getting a nucleic acid containing a nonsense mutation (optionally contained in a vector) into the patient's cells: in vivo and ex vivo. For in vivo delivery the nucleic acid is injected directly into the patient, usually at the sites where the polypeptide is required, i.e., the site of synthesis of the polypeptide, if known, and the site (e.g. solid tumor) where biological activity of the polypeptide is needed. For ex vivo treatment, the patient's cells are removed, the nucleic acid is introduced into these isolated cells, and the modified cells are administered to the patient either directly or, for example, encapsulated within porous membranes that are implanted into the patient (see e.g., U.S. Pat. Nos. 4,892,538 and 5,283,187). There are a variety of techniques available for introducing nucleic acids into viable cells. The techniques vary depending upon whether the nucleic acid is transferred into cultured cells in vitro, or transferred in vivo in the cells of the intended host. Techniques suitable for the transfer of nucleic acid into mammalian cells in vitro include the use of liposomes, electroporation, microinjection, transduction, cell fusion, DEAE-dextran, the calcium phosphate precipitation method, etc. Transduction involves the association of a replication-defective, recombinant viral (preferably retroviral) particle with a cellular receptor, followed by introduction of the nucleic acids contained by the particle into the cell. A commonly used vector for ex vivo delivery of the gene is a retrovirus.

The currently preferred in vivo nucleic and transfer techniques include transfection with viral or non-viral vectors (such as adenovirus, lentivirus, Herpes simplex I virus, or adeno-associated virus (AAV)) and lipid-based systems (useful lipids for lipid-mediated transfer of the gene are, for example, DOTMA, DOPE, and DC-Chol; see, e.g., Tonkinson el al, *Cancer Investigation*, 14 (1): 54-65 (1996)). The most preferred vectors for use in gene therapy are viruses, most preferably adenoviruses, AAV, lentiviruses, or retroviruses. A viral vector such as a retroviral vector includes at least one transcriptional promoter/enhancer or locus-defining element(s), or other elements that control gene expression by other means such as alternate splicing, nuclear RNA export, or post-translational modification of messenger. In addition, a viral vector such as a retroviral vector includes a nucleic acid sequence that, when transcribed with a gene encoding a polypeptide, is operably linked to the coding sequence and acts as a translation initiation sequence. Such vector constructs also include a packaging signal, long terminal repeats (LTRs) or portions thereof, and positive and negative strand primer binding sites appropriate to the virus used (if these are not already present in the viral vector). In addition, such vector typically includes a signal sequence for secretion of the polypeptide from a host cell in which it is placed. Preferably the signal sequence for this purpose is a mammalian signal sequence, most preferably the native signal sequence for the polypeptide. Optionally, the vector construct may also include a signal that directs polyadenylation, as well as one or more restriction sites and a translation termination sequences. By way of example, such vectors will typically include a 5' LTR, a tRNA binding site, a packaging signal, a origin of second-strand DNA synthesis, and a 3' LTR or a portion thereof. Other vectors can be used that are non-viral, such as cationic lipids, polylysine, and dendrimers.

In some situations, it is desirable to provide the nucleic acid source with an agent that targets the target cells, such as an antibody specific for a cell-surface membrane protein or the target cell, a ligand for a receptor on the target cell, etc. Where liposomes are employed, proteins that bind to a cell-surface membrane protein associated with endocytosis may be used for targeting and/or to facilitate uptake, e.g., capsid proteins or fragments thereof tropic for a particular cell type, antibodies for proteins that undergo internalization in cycling, and proteins that target intracellular localization and enhance intracellular half-life. The technique of recpto-mediated endocytosis is described, for example, by Wu et al., *J. Biol. Chem.* 262: 4429-4432 (1987); and Wagner et al., *Proc. Natl. Acad. Sci. USA*, 87: 3410-3414 (1990). For a review of the currently known gene marking and gene therapy protocols, see, Anderson et al., *Science* 256: 808-813 (1992). See also WO 93/25673 and the references cited therein.

Suitable gene therapy and methods for making retroviral particles and structural proteins can be found in, e.g. U.S. Pat. Nos. 5,681,746; 6,800,604 and 6,800,731.

To assist in understanding the present invention, the following examples are included. The experiments relating to this invention should not, of course, be construed as specifically limiting the invention and such variations of the invention, now known or later developed, which would be within the purview of one skilled in the art are considered to fall within the scope of the invention as described herein and hereinafter claimed.

EXAMPLES

The present invention is described in more detail with reference to the following non-limiting examples, which are offered to more fully illustrate the invention, but are not to be construed as limiting the scope thereof. The examples illustrate the preparation of certain compounds of the invention, and the testing of these compounds in vitro and/or in vivo. Those of skill in the art will understand that the techniques described in these examples represent techniques described by the inventors to function well in the practice of the invention, and as such constitute preferred modes for the practice thereof. However, it should be appreciated that those of skill in the art should in light of the present disclosure, appreciate that many changes can be made in the specific methods that are disclosed and still obtain a like or similar result without departing from the spirit and scope of the invention.

Example 1

Preparation of Compounds of the Invention

A. Preparation of 3,5-Triazines
The triazines of Formulas 1-A and 2-A may generally be prepared according to Scheme A as follows.

Preparation of
3-(4-p-Tolyl-[1,3,5]triazin-2-yl)benzoic acid
(Compound 43)

Part A. To a 10 mL microwave tube is added 4-methylbenzamide (0.99 g, 7.32 mmol) and N,N-dimethylformamide dimethyl acetal (2.23 g, 18.67 mmol). The tube is heated to 150° C. at 250 psi, 300 W for 10 min. A white solid is precipitated by the addition of ether/hexanes (1:1). The desired product (1.26 g, 91% yield) is collected by filtration and washed with hexanes. The obtained compound, N-dimethylaminomethylene-4-methyl-benzamide, is >90% pure as determined by LC-MS. MS (ES+): m/e 191.17.

Part B. To a mixture of tert-butanol (3.50 g, 47.22 mmol), pyridine (3.72 g, 46.78 mmol) and cat. DMAP in methylene chloride (15 mL) is added dropwise 3-cyanobenzoyl chloride (6.81 g, 41.07 mmol) and pyridine (3 mL) in methylene chloride (10 mL) at 0° C. The resulting mixture is stirred at room temperature for 20 h. The solvent is evaporated, and the residue is purified by flash chromatography (1:1 methylene chloride/hexanes) to afford 3-cyano-benzoic acid tert-butyl ester (6.84 g, 82.1% yield) as white solid. $^1$H NMR (300 MHz, CDCl$_3$): δ 8.24 (1H, s), 8.20 (1H, dd, J=7.9, 1.2 Hz), 7.78 (1H, dd, J=6.7, 1.1 Hz), 7.52 (1H, m), 1.58 (9H, s).

Part C. To a solution of 3-cyano-benzoic acid tert-butyl ester (6.54 g, 31.98 mmol) in 15 mL of THF (anhydrous) is added lithium hexamethyldisilazane (8.65 g, 51.17 mmol, 1.0 M in THF) under the protection of N$_2$. The solution is stirred at room temperature for 3 h until the starting material is consumed (monitored by TLC). The reaction mixture is poured into slurry of silica gel (80 g) in THF (120 mL), and stirred for 5 min, then the silica gel is filtered. The filter cake is further washed with THF/methanol (2:1). Evaporation of the filtrate and crystallization of the residue under vacuum yields the desired product, 3-carbamimidoyl-benzoic acid tert-butyl ester (5.80 g, 82.5% yield). The obtained compound is >90% pure as determined by LC-MS. MS (ES+): m/e 212.20.

Part D. A mixture of N-dimethylaminomethylene-4-methyl-benzamide (221.9 mg, 1.15 mmol) and 3-carbamimidoyl-benzoic acid tert-butyl ester (196.0 mg, 0.89 mmol) in anhydrous acetic acid (8 mL) is heated to 115° C. at 150 W, 250 psi in a microwave reactor for 30 min. until complete consumption of the starting material is determined by TLC. A white solid is precipitated by addition of 1 N HCl, and collected by filtration, followed by washing with water and hexanes. The obtained solid is further purified by flash column chromatography, eluting with methanol/methylene chloride (1:20) to afford the title product (23.1 mg, 5.3% yield), m.p. 298-300° C. $^1$H NMR (300 MHz, DMSO-d$_6$): δ 9.40 (1H, s), 8.63 (2H, d, J=8.3 Hz), 8.48 (2H, d, J=8.0 Hz), 8.13 (2H, d, J=8.0 Hz), 7.41 (2H, m), 2.41 (3H, s). MS (ES+): m/e 292.30.

The method described above in Example A may be used to prepare the following compounds of the invention:

Compound 44
3-[4-(4-Fluoro-phenyl)-[1,3,5]triazin-2-yl]-benzoic acid: m.p. 266-269° C. $^1$H NMR (300 MHz, DMSO-d$_6$): δ 9.43 (1H, s), 9.08 (1H, s), 8.77 (1H, dd, J=6.1, 0.9 Hz), 8.62 (2H, m), 8.20 (1H, dd, J=6.2, 1.0 Hz), 7.74 (1H, m), 7.43 (2H, m). MS (ES+): m/e 297.25 (20), 296.28 (100). MS (ES−): m/e 295.24 (20), 294.26 (100).

Compound 45
3-[4-(4-Ethoxy-phenyl)-[1,3,5]triazin-2-yl]-benzoic acid: m.p. 269-272° C. $^1$H NMR (300 MHz, DMSO-d$_6$): δ 9.33 (1H, s), 9.09 (1H, s), 8.74 (1H, dd, J=7.4, 1.0 Hz), 8.50 (2H, d, J=8.8 Hz), 8.20 (1H, dd, J=6.4, 0.8 Hz), 7.71 (1H, t, J=7.9 Hz), 7.13 (2H, d, J=8.8 Hz), 4.14 (2H, q, J=6.6 Hz), 1.36 (3H, t, J=6.8 Hz). MS (ES+): m/e 323.30 (20), 322.33 (100). MS (ES−): m/e 321.30 (20), 320.28 (100).

Compound 46
4-(4-p-Tolyl-[1,3,5]triazin-2-yl)-benzoic acid: m.p. 288-290° C. $^1$H NMR (300 MHz, DMSO-d$_6$): δ 9.41 (1H, s), 8.65 (2H, d, J=8.5 Hz), 8.47 (2H, d, J=8.3 Hz), 8.13 (2H, d, J=8.5 Hz), 7.42 (2H, d, J=8.3 Hz), 2.06 (3H, s). MS (ES+): m/e 293.31 (20), 292.30 (100). MS (ES−): m/e 291.28 (20), 290.30 (100).

Compound 47
4-[4-(4-Fluoro-phenyl)-[1,3,5]triazin-2-yl]-benzoic acid: m.p. 295-298° C. $^1$H NMR (300 MHz, DMSO-d$_6$): δ 9.44 (1H, s), 8.65 (4H, m), 8.13 (2H, d, J=8.3 Hz), 7.45 (2H, m). MS (ES+): m/e 297.24 (20), 296.22 (100). MS (ES−): m/e 295.23 (20), 294.21 (100).

Compound 48
3-[4-(4-Methoxy-phenyl)-[1,3,5]triazin-2-yl]-benzoic acid: m.p. 307-309° C. MS (ES+): m/e 309.27 (20), 308.26 (100). MS (ES−): m/e 307.26 (20), 306.25 (100).

Compound 49
3-[4-(3-Fluoro-phenyl)-[1,3,5]triazin-2-yl]-benzoic acid: m.p. 273-276° C. $^1$H NMR (300 MHz, DMSO-d$_6$): δ 9.49 (1H, s), 8.68 (2H, m), 8.43 (1H, dd, J=7.7, 1.1 Hz), 8.31 (1H, dd, J=8.8, 1.4 Hz), 8.14 (2H, m), 7.67 (1H, m), 7.55 (1H, m). MS (ES+): m/e 297.27 (20), 296.25 (100). MS (ES−): m/e 295.26 (20), 294.24 (100).

Compound 50
3-[4-(4-Trifluoromethyl-phenyl)-[1,3,5]triazin-2-yl]-benzoic acid: m.p. 290-293° C. $^1$H NMR (300 MHz, DMSO-d$_6$): δ 9.53 (1H, s), 8.67 (2H, d, J=8.3 Hz), 8.52 (2H, m), 8.11 (2H, m), 7.97 (2H, d, J=8.3 Hz). MS (ES+): m/e 347.23 (20), 346.22 (100). MS (ES−): m/e 345.21 (20), 344.24 (100).

Compound 51

3-[4-(3-Methoxy-phenyl)-[1,3,5]triazin-2-yl]-benzoic acid: m.p. 227-229° C. $^1$H NMR (300 MHz, DMSO-d$_6$): δ 9.44 (1H, s), 8.65 (2H, m), 8.15 (3H, m), 8.06 (1H, s), 7.54 (1H, t, J=7.7 Hz), 7.24 (1H, dd, J=8.0, 1.2 Hz), 3.87 (3H, s). MS (ES+): m/e 309.27 (20), 308.26 (100). MS (ES−): m/e 307.26 (20), 306.23 (100).

Compound 53

4-[4-(4-Methoxy-phenyl)-[1,3,5]triazin-2-yl]-benzoic acid: m.p. >300° C. $^1$H NMR (300 MHz, DMSO-d$_6$): δ 9.35 (1H, s), 8.64 (2H, d, J=8.5 Hz), 8.53 (2H, d, J=8.9 Hz), 8.12 (2H, d, J=8.5 Hz), 7.13 (2H, d, J=8.9 Hz), 3.87 (3H, s). MS (ES+): m/e 309.27 (20), 308.26 (100). MS (ES−): m/e 307.26 (20), 306.25 (100).

B. Preparation of 4,2-Pyrimidines

Pyrimidines of the invention may be generally prepared according to Scheme B as follows.

Preparation of 3-[2-(4-amino-phenyl)-pyrimidin-4-yl]-benzonitrile (Compound 1)

Part A. A flask containing absolute ethanol (10 mL) is cooled to 0° C., and sodium hydride (42 mg, 60% w/w with mineral oil, 1.05 mmol) is added. After stirring for 0.5 h., the solution is treated with 4-aminobenzamidine dihydrochloride (104 mg, 0.50 mmol) and the mixture is allowed to stir for 5 min. Then, 3-(3-dimethylamino-acryloyl)-benzonitrile (100 mg, 0.50 mmol) is added, and the resulting mixture is heated to reflux for 3 h. then cooled to ambient temperature and stirred for 60 h. The mixture is evaporated, and the resulting mixture is triturated with diethyl ether and filtered. The filtrate is evaporated to afford a yellow oil, which is separated by column chromatography (1:1 ethyl acetate-hexane) to afford the product, 3-[2-(4-amino-phenyl)-pyrimidin-4-yl]-benzonitrile (76 mg, 56%). $^1$H NMR (300 MHz, CDCl$_3$): δ 8.75 (1H, d, J=6 Hz), 8.49 (1H, t, J=2 Hz), 8.37-8.31 (3H, m), 7.75 (1H, dt, J=8, 2 Hz), 7.59 (1H, t, J=8 Hz), 7.40 (1H, d, J=6 Hz), 6.76 (2H, d, J=9 Hz), 4.03 (2H, br s). $^{13}$C NMR (CDCl$_3$): δ 164.6, 160.8, 158.0, 149.2, 138.2, 133.6, 131.0, 130.7, 129.8 (2C), 129.5, 127.2, 118.5, 114.5 (2C), 113.0, 112.9. MS (ES+): m/e 274 (20), 273 (100).

Preparation of 3-[2-(4-Isopropyl-phenyl)-pyrimidin-4-yl]-benzamide (Compound 4)

A mixture of 3-[2-(4-isopropyl-phenyl)-pyrimidin-4-yl]-benzonitrile (50 mg, 0.167 mmol) and aq. H$_2$SO$_4$ (257 µL, 0.65 M) is heated to 70° C. for 12 h. The mixture is cooled and adjusted to pH 7 with aq. sodium hydroxide (1 M). The mixture is partitioned between water and ethyl acetate, and the organic layer is washed with satd. aq. sodium chloride solution, dried over magnesium sulfate, filtered and evaporated to afford the title compound as a white crystalline solid (52 mg, 98%), m.p. 167-169° C. $^1$H NMR (300 MHz, acetone-d$_6$): δ 8.91 (1H, d, J=6 Hz), 8.87 (1H, t, J=2 Hz), 8.54 (2H, d, J=9 Hz), 8.52 (1H, ddd, J=8, 2, 1 Hz), 8.15 (1H, ddd, J=8, 2, 1 Hz), 7.93 (1H, d, J=6 Hz), 7.80 (1H, br s), 7.68 (1H, t, J=8 Hz), 7.41 (2H, d, J=9 Hz), 6.96 (1H, br s), 3.01 (1H, heptet, J=7 Hz), 1.30 (6H, d, J=7 Hz). $^{13}$C NMR (acetone-d$_6$): δ 205.9, 168.4, 164.8, 163.4, 159.0, 152.4, 137.8, 136.2, 135.9, 130.6 (2C), 129.7, 128.9, 127.2 (2C), 126.8, 115.4, 34.7, 24.1 (2C). MS (ES+): m/e 319 (25), 318 (100).

Preparation of 4-[2-(4-Isopropyl-phenyl)-pyrimidin-4-yl]-benzoic acid (Compound 5)

Part A. A solution of methyl 4-acetylbenzoate (1.00 g, 5.61 mmol) and dimethylformamide dimethyl acetal (746 µL, 5.61 mmol) in ethanol (5 mL) is heated to reflux for 12 h. The solution is cooled and evaporated, and the residue is separated by column chromatography to afford the product as a mixture of methyl and ethyl esters of 4-(3-dimethylamino-acryloyl) benzoic acid (679 mg). A portion of this material (121 mg) is dissolved in ethanol (5 mL) and treated with 4-isopropyl-benzamidine (81 mg). The solution is heated to reflux for 12 h., cooled, filtered through celite, and evaporated. The residue is separated by column chromatography (silica gel, 1:4 ethyl acetate-hexane) to afford the product, ethyl 4-[2-(4-isopropyl-phenyl)-pyrimidin-4-yl]-benzoate.

Part B. A solution of ethyl 4-[2-(4-isopropyl-phenyl)-pyrimidin-4-yl]-benzoate in THF-water-ethanol (2 mL/2 mL/1 mL) is treated with lithium hydroxide hydrate (60 mg) and stirred for 12 h. The solution is evaporated, and the residue is partitioned between 1 M aq. HCl and ethyl acetate. The organic phase is washed with water (20 mL), dried over magnesium sulfate, filtered and evaporated to afford the title compound as a white solid (65 mg, 41%), m.p. 262-264° C. $^1$H NMR (300 MHz, acetone-d$_6$): δ 8.96 (1H, d, J=6 Hz), 8.48 (2H, d, J=9 Hz), 8.23 (2H, d, J=9 Hz), 8.12 (2H, d, J=9 Hz), 7.98 (1H, d, J=6 Hz), 7.44 (2H, d, J=9 Hz), 3.02 (1H, heptet, J=7 Hz), 1.33 (6H, d, J=7 Hz). MS (ES+): m/e 320 (20), 319 (100). MS (ES−): m/e 318 (20), 317 (100).

The following compound may be prepared in a similar manner to that described above with reference to Compound 5.

Compound 10

4-(2-p-Tolyl-pyrimidin-4-yl)-benzoic acid: m.p. >310° C. $^1$H NMR (300 MHz, DMSO-d$_6$): δ 8.96 (1H, d, J=6 Hz), 8.43 (2H, d, J=9 Hz), 8.40 (2H, d, J=9 Hz), 8.10 (2H, d, J=9 Hz), 8.03 (1H, d, J=6 Hz), 7.35 (2H, d, J=9 Hz), 2.39 (3H, s). MS (ES+): m/e 292 (20), 291 (100). MS (ES−): m/e 290 (20), 289 (100).

Preparation of 3-(2-p-Tolyl-pyrimidin-4-yl)-benzoic acid (Compound 9)

Part A. 4-Methylbenzonitrile is used to prepare 4-methyl-benzamidine in the manner described above and used along with 3-(3-dimethylamino-acryloyl)-benzonitrile in the synthesis of 3-(2-p-tolyl-pyrimidin-4-yl)-benzonitrile with the conditions described previously.

Part B. A solution of 3-(2-p-tolyl-pyrimidin-4-yl)-benzonitrile (87 mg, 0.321 mmol) in ethanol (2 mL) is treated with aq. sodium hydroxide solution (1 mL, 10 N), and the resulting solution is heated to reflux until the starting material is consumed as determined by LC/MS. After being allowed to cool, the solution is evaporated and subjected to aqueous workup. The extract, which contained a mixture of amide and acid compounds, is separated by column chromatography to afford pure title compound (11 mg) as a white solid, m.p. 225-226° C. $^1$H NMR (300 MHz, DMSO-d$_6$): δ 8.94 (1H, d, J=6 Hz), 8.82 (1H, s), 8.53 (1H, d, J=8 Hz), 8.39 (2H, d, J=9 Hz), 8.11 (1H, d, J=8 Hz), 8.03 (1H, d, J=6 Hz), 7.71 (1H, t, J=8 Hz), 7.37 (2H, d, J=9 Hz), 2.40 (3H, s). MS (ES+): m/e 292 (20), 291 (100). MS (ES−): m/e 290 (20), 289 (100).

The following compounds may be prepared in a similar manner to that described above with reference to Compound 9.

Compound 16

4-[2-(3-Methoxy-phenyl)-pyrimidin-4-yl]-benzoic acid: m.p. 270-273° C. $^1$H NMR (300 MHz, DMSO-d$_6$): δ 13.22 (1H, br s), 9.00 (1H, d, J=5 Hz), 8.44 (2H, d, J=8 Hz), 8.14-8.03 (5H, m), 7.48 (1H, t, J=8 Hz), 7.16-7.11 (1H, m), 3.86 (3H, s). MS (ES+): m/e 307.11 (100). MS (ES−): m/e 305.13 (100).

Compound 17

4-[2-(4-tert-Butyl-phenyl)-pyrimidin-4-yl]-benzoic acid: m.p. 293-296° C. $^1$H NMR (300 MHz, DMSO-d$_6$): δ 13.23 (1H, br s), 8.97 (1H, d, J=5 Hz), 8.43 (4H, d, J=8 Hz), 8.12 (2H, d, J=8 Hz), 8.03 (1H, d, J=5 Hz), 7.57 (2H, d, J=8 Hz). MS (ES+): m/e 333.18 (100). MS (ES−): m/e 331.15 (100).

Compound 18

4-[2-(4-Fluoro-phenyl)-pyrimidin-4-yl]-benzoic acid: m.p. >300° C. $^1$H NMR (300 MHz, DMSO-d$_6$): δ 13.21 (1H, br s), 8.99 (1H, d, J=5 Hz), 8.57 (2H, dd, J=8, 6 Hz), 8.44 (2H, d, J=8 Hz), 8.11 (2H, d, J=8 Hz), 8.08 (1H, d, J=5 Hz), 7.38 (2H, t, J=8 Hz). MS (ES+): m/e 295.10 (100). MS (ES−): m/e 293.06 (100).

Compound 19

4-[2-(3-Trifluoromethoxy-phenyl)-pyrimidin-4-yl]-benzoic acid: m.p. >300° C. $^1$H NMR (300 MHz, DMSO-d$_6$): δ 9.07-9.04 (1H, m), 8.37 (2H, d, J=8 Hz), 8.18-8.16 (1H, m), 8.13-8.08 (3H, m), 7.71-7.53 (3H, m). MS (ES+): m/e 361.09 (100). MS (ES−): m/e 359.05 (100).

Compound 20

4-[2-(3-Chloro-phenyl)-pyrimidin-4-yl]-benzoic acid: m.p. 291-294° C. $^1$H NMR (300 MHz, DMSO-d$_6$): δ 9.03 (1H, d, J=5 Hz), 8.49-8.43 (4H, m), 8.14-8.11 (3H, m), 7.65-7.60 (2H, m). MS (ES+): m/e 311.07 (100). MS (ES−): m/e 309.06 (100).

Compound 21

4-[2-(4-Trifluoromethyl-phenyl)-pyrimidin-4-yl]-benzoic acid: m.p. >300° C. $^1$H NMR (300 MHz, DMSO-d$_6$): δ 13.22 (1H, br s), 9.06 (1H, d, J=5 Hz), 8.70 (2H, d, J=8 Hz), 8.46 (2H, d, J=8 Hz), 8.15 (1H, d, J=5 Hz), 8.12 (2H, d, J=8 Hz), 7.93 (2H, d, J=8 Hz). MS (ES+): m/e 345.16 (100).

Compound 61

4-[2-(2-Trifluoromethoxy-phenyl)-pyrimidin-4-yl]-benzoic acid: m.p. 258-261° C. $^1$H NMR (300 MHz, DMSO-d$_6$): δ 9.05 (1H, d, J=5 Hz), 8.36 (2H, d, J=8 Hz), 8.16-8.06 (4H, m), 7.70-7.51 (3H, m). MS (ES+): m/e 361.12 (100).

Compound 22

4-[2-(4-Chloro-phenyl)-pyrimidin-4-yl]-benzoic acid: m.p. >300° C. $^1$H NMR (300 MHz, DMSO-d$_6$): δ 13.24 (1H, br s), 9.01 (1H, d, J=5 Hz), 8.52 (2H, d, J=8 Hz), 8.44 (2H, d, J=8 Hz), 8.13-8.08 (3H, m), 7.62 (2H, d, J=5 Hz). MS (ES+): m/e 311.11 (100).

Compound 23

4-[2-(2-Fluoro-phenyl)-pyrimidin-4-yl]-benzoic acid: m.p. >300° C. $^1$H NMR (300 MHz, DMSO-d$_6$): δ 13.22 (1H, br s), 9.04 (1H, d, J=5 Hz), 8.39 (2H, d, J=8 Hz), 8.14-8.08 (4H, m), 7.62-7.58 (1H, m), 7.40-7.36 (2H, m). MS (ES+): m/e 295.15 (100).

Compound 62

4-[2-(3-Trifluoromethyl-phenyl)-pyrimidin-4-yl]-benzoic acid: $^1$H NMR (300 MHz, DMSO-d$_6$): δ 9.04 (1H, d, J=5 Hz), 8.82 (1H, d, J=8 Hz), 8.76 (1H, s), 8.42 (2H, d, J=8 Hz), 8.16 (1H, d, J=5 Hz), 8.07 (2H, d, J=8 Hz), 7.94 (1H, d, J=8 Hz), 7.82 (1H, d, J=8 Hz), 7.55 (1H, s). MS (ES+): m/e 345.21 (100).

Compound 25

4-[2-(3-Fluoro-phenyl)-pyrimidin-4-yl]-benzoic acid: m.p. 300-303° C. $^1$H NMR (300 MHz, DMSO-d$_6$): δ 13.22 (1H, br s), 9.00 (1H, d, J=5 Hz), 8.45-8.09 (7H, m), 7.59 (1H, m), 7.39 (1H, m). MS (ES+): m/e 295.15 (100).

Compound 26

4-(2-o-Tolyl-pyrimidin-4-yl)-benzoic acid: m.p. 198-200° C. $^1$H NMR (300 MHz, DMSO-d$_6$): δ 13.21 (1H, br s), 9.02 (1H, d, J=5 Hz), 8.37 (2H, d, J=8 Hz), 8.11-8.07 (2H, m), 7.89 (1H, d, J=5 Hz), 7.38-7.33 (3H, m), 2.58 (3H, s). MS (ES+): m/e 291.20 (100).

Compound 27

4-[2-(4-Trifluoromethoxy-phenyl)-pyrimidin-4-yl]-benzoic acid: m.p. 299-302° C. $^1$H NMR (300 MHz, DMSO-d$_6$): δ 9.02 (1H, d, J=5 Hz), 8.62 (2H, d, J=8 Hz), 8.44 (2H, d, J=8 Hz), 8.12 (1H, d, J=5 Hz), 8.11 (2H, d, J=8 Hz), 7.54 (2H, d, J=8 Hz). MS (ES+): m/e 361.18 (100).

Compound 28

4-(2-Phenyl-pyrimidin-4-yl)-benzoic acid: m.p. >300° C. $^1$H NMR (300 MHz, DMSO-d$_6$): δ 9.00 (1H, d, J=5 Hz), 8.54-8.50 (2H, m), 8.45 (2H, d, J=8 Hz), 8.11 (2H, d, J=8 Hz), 8.08 (1H, d, J=5 Hz), 7.57-7.54 (3H, m). MS (ES+): m/e 277.22 (100).

Compound 30

4-[2-(4-Methoxy-phenyl)-pyrimidin-4-yl]-benzoic acid: m.p. >300° C. $^1$H NMR (300 MHz, DMSO-d$_6$): δ 13.20 (1H, br s), 8.93 (1H, d, J=5 Hz), 8.46 (2H, d, J=8 Hz), 8.42 (2H, d, J=8 Hz), 8.11 (2H, d, J=8 Hz), 7.98 (1H, d, J=5 Hz), 7.09 (2H, d, J=8 Hz), 3.84 (3H, s). MS (ES+): m/e 307.27 (100). MS (ES−): m/e 305.23 (100).

Compound 31

4-[2-(2-Trifluoromethyl-phenyl)-pyrimidin-4-yl]-benzoic acid: m.p. 251-252° C. $^1$H NMR (300 MHz, DMSO-d$_6$): δ 9.04 (1H, d, J=5 Hz), 8.35 (2H, d, J=8 Hz), 8.19 (1H, d, J=5 Hz), 8.08 (2H, d, J=8 Hz), 7.92-7.73 (4H, m). MS (ES+): m/e 345.29 (100).

C. 4,6-Pyrimidines

The 4,6 pyrimidines of Formulas 1-C and 2-C may generally be prepared according to Scheme C as follows.

Preparation of 4-(6-m-Tolyl-pyrimidin-4-yl)-benzoic acid (Compound 2)

Part A. A 50 mL three-neck round-bottom flask is charged with 2,4-dichloropyrimidine (0.58 g, 3.89 mmol), 3-methylphenylboronic acid (0.31 g, 2.28 mmol), Na$_2$CO$_3$ (0.73 g, 6.88 mmol), tetrakis(triphenylphosphine) palladium (13.0 mg, 1.12×10$^{-2}$ mmol). The flask is evacuated, and refilled with N$_2$. DMF (15 mL, anhydrous) is then added to the flask. The flask is evacuated again, and refilled with N$_2$, repeated two times. The reaction is heated to 100° C. overnight. The reaction mixture is partitioned between ethyl ether and water. The organic layer is washed with brine, dried over MgSO$_4$, and then removed. The residue is further purified by flash column chromatography, eluting with methylene chloride/hexanes (1:10) to afford 45.7 mg (5.8% yield) of desired product. The obtained compound (4-chloro-6-m-tolyl-pyrimidine) is >80% pure as determined by LC-MS. MS (ES+): m/e 205.23.

Part B. A 10 mL microwave tube is charged with 4-chloro-6-m-tolyl-pyrimidine (45.7 mg, 0.22 mmol), 4-carboxyphenylboronic acid (39.2 mg, 0.23 mmol), (235.3 mg, 2.22 mmol), Na$_2$CO$_3$ (70.6 mg, 0.67 mmol), tetrabutylammonium iodide (83.0 mg, 0.22 mmol), palladium acetate (0.5 mg, 2.2×mmol) and 2 mL of water. The reaction mixture is heated to 150° C. at 60 w, 250 psi in a microwave reactor for 10 min. The reaction mixture is added to 5 mLl of 6 N HCl and extracted with ethyl acetate (10 mL). The organic portion is washed with saturated NaHCO$_3$ and brine, dried (MgSO$_4$), and concentrated on a rotary evaporator. The oily residue is suspended in ethyl acetate/hexanes (1:1) to provide 9.8 mg (15.1% yield) of white powder as the desired product, m.p. 211-213° C. $^1$H NMR (300 MHz, DMSO-d$_6$): δ 9.31 (1H, s), 8.66 (1H, s), 8.46 (2H, d, J=8.3 Hz), 8.20 (1H, s), 8.15 (1H, dd, J=8.0, 1.2 Hz), 8.09 (2H, d, J=8.3 Hz), 7.45 (1H, t, J=7.7 Hz), 7.38 (1H, dd, J=7.7, 1.0 Hz). MS (ES+): m/e 291.58.

The following compound may be prepared in a similar manner to that described above with reference to Compound 2.

Compound 3

3-(6-p-Tolyl-pyrimidin-4-yl)-benzoic acid: m.p. 201-203° C. $^1$H NMR (300 MHz, DMSO-$d_6$): δ 9.19 (1H, s), 8.69 (1H, s), 8.30 (1H, dd, J=7.9, 1.1 Hz), 8.11 (1H, dd, J=7.7, 1.0 Hz), 8.06 (1H, s), 7.97 (2H, d, J=8.2 Hz), 7.52 (1H, t, J=7.7 Hz), 7.25 (2H, d, J=8.2 Hz). MS (ES+): m/e 292.40 (20), 291.37 (100). MS (ES−): m/e 291.46 (20), 290.47 (100).

D. Preparation of 2,4-Pyrimidines

The 2,4 pyrimidines of Formulas 1-D and 2-D may generally be prepared according to Scheme D as follows.

Preparation of 3-[4-(4-Fluoro-phenyl)-pyrimidin-2-yl]-benzoic acid (Compound 32)

Part A. To a 10 mL microwave tube is added 4-fluoroacetophenone (1.01 g, 7.31 mmol) and N,N-dimethylformamide dimethyl acetal (0.87 g, 7.32 mmol). The tube is heated to 100° C. at 250 psi, 300 W for 10 min. A yellow solid is precipitated by addition of hexanes. The desired product (1.03 g, 73.0% yield) is collected by filtration and washed with hexanes. The obtained compound, 3-dimethylamino-1-(4-fluoro-phenyl)-propenone, is >90% pure as determined by LC-MS. MS (ES+): m/e 194.14.

Part B. To a mixture of 3-carbamimidoyl-benzoic acid tert-butyl ester (220.2 mg, 0.94 mmol), 3-dimethylamino-1-(4-fluoro-phenyl)-propenone (182.6 mg, 0.95 mmol) and sodium hydride (39.2 mg, 1.63 mmol, 60% in hexanes) is added dry ethanol (5.0 mL). The resulting mixture is stirred at refluxing for 8 h until complete consumption of the starting material as determined by TLC. The solvent is removed, and the residue is added to 1N HCl (15 mL) to precipitate a yellow solid. The title product (137.8 mg, 41.3% yield) is produced after washing with water, then ethyl ether in sequence, m.p. 239-241° C. $^1$H NMR (300 MHz, DMSO-d6): δ 9.05 (1H, s), 8.97 (1H, d, J=5.0 Hz), 8.73 (1H, dd, J=7.7, 1.2 Hz), 8.38 (2H, m), 8.11 (1H, dd, J=8.0, 1.2 Hz), 8.04 (1H, d, J=5.3 Hz), 7.68 (1H, t, J=7.8 Hz), 7.43 (2H, m). MS (ES+): m/e 295.27.

The following compounds may be prepared in a similar manner to that described above with reference to Compound 32.

Compound 33

4-[4-(4-Bromo-phenyl)-pyrimidin-2-yl]-benzoic acid: m.p. 302-305° C. $^1$H NMR (300 MHz, DMSO-$d_6$): δ 9.00 (1H, d, J=5.1 Hz), 8.60 (2H, d, J=8.3 Hz), 8.30 (2H, d, J=8.5 Hz), 8.10 (3H, m), 7.85 (2H, d, J=8.5 Hz). MS (ES+): m/e 358.13 (20), 357.12 (100). MS (ES−): m/e 356.01 (20), 355.08 (100).

Compound 34

4-[4-(4-Trifluoromethoxy-phenyl)-pyrimidin-2-yl]-benzoic acid: m.p. 234-236° C. $^1$H NMR (300 MHz, DMSO-$d_6$): δ 9.01 (1H, d, J=5.4 Hz), 8.58 (2H, d, J=8.3 Hz), 8.46 (2H, d, J=8.8 Hz), 8.09 (3H, m), 7.57 (2H, d, J=8.3 Hz). MS (ES+): m/e 362.22 (20), 361.23 (100). MS (ES−): m/e 360.20 (20), 359.20 (100).

Compound 35

4-(4-p-Tolyl-pyrimidin-2-yl)-benzoic acid: m.p. 287-289° C. $^1$H NMR (300 MHz, DMSO-$d_6$): δ 8.94 (1H, d, J=5.4 Hz), 8.60 (2H, d, J=8.3 Hz), 8.23 (2H, d, J=8.3 Hz), 8.10 (2H, d, J=8.5 Hz), 8.02 (1H, d, J=5.4 Hz), 7.38 (2H, d, J=8.1 Hz), 2.40 (3H, s). MS (ES+): m/e 292.29 (20), 291.26 (100). MS (ES−): m/e 290.24 (20), 289.26 (100).

Compound 36

4-[4-(4-Isopropyl-phenyl)-pyrimidin-2-yl]-benzoic acid: m.p. 243-245° C. $^1$H NMR (300 MHz, DMSO-$d_6$): δ 8.95 (1H, d, J=5.4 Hz), 8.60 (2H, d, J=8.0 Hz), 8.25 (2H, d, J=8.3 Hz), 8.10 (2H, d, J=8.3 Hz), 8.01 (1H, d, J=5.1 Hz), 7.45 (2H, d, J=8.0 Hz), 2.97 (1H, m), 1.25 (6H, d, J=5.1 Hz). MS (ES+): m/e 320.30 (20), 319.29 (100). MS (ES−): m/e 318.30 (20), 317.30 (100).

Compound 37

4-[4-(4-Methoxy-phenyl)-pyrimidin-2-yl]-benzoic acid: m.p. 263-265° C. $^1$H NMR (300 MHz, DMSO-$d_6$): δ 8.89 (1H, d, J=5.5 Hz), 8.59 (2H, d, J=7.2 Hz), 8.32 (2H, d, J=7.5 Hz), 8.10 (2H, d, J=7.2 Hz), 8.00 (1H, d, J=5.5 Hz), 7.12 (2H, d, J=7.5 Hz), 3.84 (3H, s). MS (ES+): m/e 308.26 (20), 307.25 (100). MS (ES−): m/e 306.34 (20), 305.25 (100).

Compound 38

4-[4-(3-Fluoro-phenyl)-pyrimidin-2-yl]-benzoic acid: m.p. 249-252° C. $^1$H NMR (300 MHz, DMSO-$d_6$): δ 9.02 (1H, d, J=5.5 Hz), 8.61 (2H, d, J=8.0 Hz), 8.12 (5H, m), 7.65 (1H, m), 7.41 (1H, m). MS (ES+): m/e 296.22 (20), 295.20 (100). MS (ES−): m/e 294.26 (20), 293.21 (100).

Compound 39

4-(4-Biphenyl-4-yl-pyrimidin-2-yl)-benzoic acid: m.p. 293-296° C. $^1$H NMR (300 MHz, DMSO-$d_6$): δ 9.01 (1H, d, J=5.2 Hz), 8.63 (2H, d, J=8.5 Hz), 8.45 (2H, d, J=8.0 Hz), 8.12 (3H, m), 7.89 (2H, d, J=8.3 Hz), 7.77 (2H, d, J=8.3 Hz), 7.44 (3H, m). MS (ES+): m/e 354.26 (20), 353.24 (100). MS (ES−): m/e 352.25 (20), 351.23 (100).

Compound 40

4-[4-(2,3-Dihydro-benzo[1,4]dioxin-6-yl)-pyrimidin-2-yl]-benzoic acid: m.p. 272-274° C. $^1$H NMR (300 MHz, DMSO-$d_6$): δ 8.89 (1H, d, J=5.3 Hz), 8.58 (2H, d, J=8.4 Hz), 8.09 (2H, d, J=8.4 Hz), 7.97 (1H, d, J=5.3 Hz), 7.87 (2H, m), 7.03 (1H, d, J=9.1 Hz), 4.32 (4H, t, J=1.2 Hz). MS (ES+): m/e 336.27 (20), 335.25 (100). MS (ES−): m/e 334.31 (20), 333.29 (100).

Compound 41

4-[4-(4-Imidazol-1-yl-phenyl)-pyrimidin-2-yl]-benzoic acid: m.p. >305° C. MS (ES+): m/e 344.25 (20), 343.23 (100). MS (ES−): m/e 342.28 (20), 341.27 (100).

Compound 63

4-[4-(3-Trifluoromethyl-phenyl)-pyrimidin-2-yl]-benzoic acid: m.p. 271-273° C. $^1$H NMR (300 MHz, DMSO-$d_6$): δ 9.04 (1H, d, J=5.2 Hz), 8.60 (4H, m), 8.20 (1H, d, J=5.2 Hz), 8.10 (2H, d, J=8.3 Hz), 7.95 (1H, dd, J=7.4, 0.9 Hz), 7.82 (1H, t, J=7.4 Hz). MS (ES+): m/e 346.28 (20), 345.26 (100). MS (ES−): m/e 344.25 (20), 343.25 (100).

Compound 64

4-(4-m-Tolyl-pyrimidin-2-yl)-benzoic acid: m.p. 220-222° C. $^1$H NMR (300 MHz, DMSO-$d_6$): δ 8.97 (1H, d, J=4.3 Hz), 8.60 (2H, d, J=7.4 Hz), 8.12 (4H, m), 8.06 (1H, d, J=4.3 Hz), 7.45 (2H, m), 2.43 (3H, s). MS (ES+): m/e 292.29 (20), 291.28 (100). MS (ES−): m/e 290.29 (20), 289.29 (100).

Compound 65

4-[4-(2-Fluoro-phenyl)-pyrimidin-2-yl]-benzoic acid: m.p. 234-236° C. MS (ES+): m/e 296.22 (20), 295.20 (100). MS (ES−): m/e 294.25 (20), 293.23 (100).

Compound 66

4-[4-(4-Trifluoromethyl-phenyl)-pyrimidin-2-yl]-benzoic acid: m.p. 282-285° C. $^1$H NMR (300 MHz, DMSO-$d_6$): δ 9.05 (1H, d, J=5.2 Hz), 8.59 (2H, d, J=7.7 Hz), 8.51 (2H, d, J=8.3 Hz), 8.14 (1H, d, J=5.2 Hz), 8.09 (2H, d, J=7.7 Hz), 7.92 (2H, d, J=8.3 Hz). MS (ES+): m/e 346.39 (20), 345.42 (100). MS (ES−): m/e 344.45 (20), 343.45 (100).

Compound 67

4-[4-(4-Morpholin-4-yl-phenyl)-pyrimidin-2-yl]-benzoic acid: m.p. 289-291° C. $^1$H NMR (300 MHz, DMSO-$d_6$): δ 8.83 (1H, d, J=5.5 Hz), 8.58 (2H, d, J=8.3 Hz), 8.22 (2H, d, J=8.5 Hz), 8.08 (2H, d, J=8.3 Hz), 7.90 (1H, d, J=5.5 Hz), 7.08 (2H, d, J=8.5 Hz), 3.74 (4H, t, J=1.2 Hz), 3.26 (4H, t, J=1.2 Hz). MS (ES+): m/e 363.32 (20), 362.31 (100). MS (ES−): m/e 361.31 (20), 360.29 (100).

Compound 68

3-[4-(4-Bromo-phenyl)-pyrimidin-2-yl]-benzoic acid: m.p. >300° C. MS (ES+): m/e 357 (100), 355 (100).

Compound 69

3-[4-(4-Trifluoromethoxy-phenyl)-pyrimidin-2-yl]-benzoic acid: m.p. 241-243° C. $^1$H NMR (300 MHz, DMSO-d$_6$): δ 9.05 (1H, s), 9.00 (1H, d, J=5.5 Hz), 8.73 (1H, dd, J=8.0, 1.1 Hz), 8.43 (2H, d, J=8.6 Hz), 8.07 (2H, m), 7.68 (1H, t, J=8.0 Hz), 7.57 (2H, d, J=8.6 Hz). MS (ES+): m/e 362.24 (20), 361.23 (100). MS (ES−): m/e 360.25 (20), 359.25 (100).

Compound 70

3-[4-(4-Isopropyl-phenyl)-pyrimidin-2-yl]-benzoic acid: m.p. 242-244° C. $^1$H NMR (300 MHz, DMSO-d$_6$): δ 9.07 (1H, s), 8.94 (1H, d, J=5.2 Hz), 8.73 (1H, dd, J=7.7, 1.0 Hz), 8.23 (2H, d, J=8.4 Hz), 8.10 (1H, dd, J=8.0, 1.2 Hz), 7.98 (1H, d, J=5.2 Hz), 7.69 (1H, t, J=7.7 Hz), 7.45 (2H, d, J=8.4 Hz), 2.95 (1H, m), 1.23 (6H, d, J=6.9 Hz). MS (ES+): m/e 320.30 (20), 319.29 (100). MS (ES−): m/e 318.40 (20), 317.30 (100).

Compound 71

3-[4-(4-Methoxy-phenyl)-pyrimidin-2-yl]-benzoic acid: m.p. 243-244° C. $^1$H NMR (300 MHz, DMSO-d$_6$): δ 9.06 (1H, s), 8.89 (1H, d, J=5.2 Hz), 8.72 (1H, dd, J=7.4, 1.0 Hz), 8.30 (2H, d, J=9.0 Hz), 8.09 (1H, dd, J=7.4, 1.0 Hz), 7.95 (1H, d, J=5.5 Hz), 7.66 (1H, t, J=7.7 Hz), 7.13 (2H, d, J=9.0 Hz), 3.85 (3H, s). MS (ES+): m/e 308.30 (20), 307.29 (100). MS (ES−): m/e 306.26 (20), 305.25 (100).

Compound 72

3-[4-(2-Fluoro-phenyl)-pyrimidin-2-yl]-benzoic acid: m.p. 201-203° C. $^1$H NMR (300 MHz, DMSO-d$_6$): δ 9.01 (2H, m), 8.70 (1H, dd, J=7.7, 1.0 Hz), 8.23 (1H, t, J=6.9 Hz), 8.10 (1H, dd, J=7.7, 0.9 Hz), 7.85 (1H, d, J=3.6 Hz), 7.61 (21-1, m), 7.41 (2H, m). MS (ES+): m/e 296.27 (20), 295.27 (100). MS (ES−): m/e 294.28 (20), 293.26 (100).

Compound 42

3-[4-(2,3-Dihydro-benzo[1,4]dioxin-6-yl)-pyrimidin-2-yl]-benzoic acid: m.p. 239-241° C. $^1$H NMR (300 MHz, DMSO-d$_6$): δ 9.05 (1H, s), 8.88 (1H, d, J=5.2 Hz), 8.70 (1H, dd, J=8.0, 1.2 Hz), 8.09 (1H, d, J=7.4 Hz), 7.95 (1H, d, J=5.0 Hz), 7.86 (1H, s), 7.82 (1H, m), 7.67 (1H, t, J=7.7 Hz), 7.01 (1H, dd, J=8.3, 1.3 Hz), 4.32 (4H, t, J=1.2 Hz). MS (ES+): m/e 336.27 (20), 335.25 (100). MS (ES−): m/e 334.22 (20), 333.23 (100).

Compound 73

3-(4-p-Tolyl-pyrimidin-2-yl)-benzoic acid: m.p. 252-253° C. $^1$H NMR (300 MHz, DMSO-d$_6$): δ 9.06 (1H, s), 8.93 (1H, d, J=5.0 Hz), 8.73 (1H, dd, J=7.4, 1.0 Hz), 8.22 (2H, d, J=7.7 Hz), 8.09 (1H, dd, J=6.9, 0.8 Hz), 7.99 (1H, d, J=5.2 Hz), 7.68 (1H, t, J=7.4 Hz), 7.39 (2H, d, J=7.7 Hz), 2.38 (3H, s). MS (ES+): m/e 292.30 (20), 291.28 (100). MS (ES−): m/e 290.33 (20), 289.15 (100).

Compound 74

3-[4-(3-Fluoro-phenyl)-pyrimidin-2-yl]-benzoic acid: m.p. 253-255° C. $^1$H NMR (300 MHz, DMSO-d$_6$): δ 9.05 (1H, s), 9.00 (1H, d, J=5.0 Hz), 8.74 (1H, d, J=7.2, 1.0 Hz), 8.18 (4H, m), 7.68 (2H, m), 7.43 (1H, m). MS (ES+): m/e 296.41 (20), 295.39 (100). MS (ES−): m/e 294.41 (20), 293.42 (100).

Compound 75

3-(4-Biphenyl-4-yl-pyrimidin-2-yl)-benzoic acid: m.p. 296-299° C. $^1$H NMR (300 MHz, DMSO-d$_6$): δ 9.18 (1H, s), 9.00 (1H, d, J=5.4 Hz), 8.77 (1H, dd, J=7.8, 1.1 Hz), 8.43 (2H, d, J=8.0 Hz), 8.17 (2H, m), 7.95 (2H, d, J=8.0 Hz), 7.87 (3H, m), 7.43 (3H, m). MS (ES+): m/e 354.28 (20), 353.31 (100). MS (ES−): m/e 352.29 (30), 351.21 (100).

Compound 76

3-(4-m-Tolyl-pyrimidin-2-yl)-benzoic acid: m.p. 217-219° C. $^1$H NMR (300 MHz, DMSO-d$_6$): δ 9.06 (1H, s), 8.96 (1H, d, J=5.5 Hz), 8.77 (1H, dd, J=7.9, 1.0 Hz), 8.13 (3H, m), 8.02 (1H, d, J=5.5 Hz), 7.69 (1H, t, J=7.0 Hz), 7.41 (2H, m), 2.43 (3H, s). MS (ES+): m/e 292.30 (20), 291.28 (100). MS (ES−): m/e 290.18 (20), 289.26 (100).

Compound 77

3-[4-(3-Trifluoromethyl-phenyl)-pyrimidin-2-yl]-benzoic acid: m.p. 271-273° C. $^1$H NMR (300 MHz, DMSO-d$_6$): δ 9.02 (2H, m), 8.70 (1H, dd, J=8.8, 1.2 Hz), 8.68 (2H, m), 8.15 (1H, d, J=5.2 Hz), 8.08 (1H, dd, J=7.2, 1.0 Hz), 7.91 (1H, m), 7.80 (1H, m), 7.67 (1H, t, J=7.0 Hz). MS (ES+): m/e 346.26 (20), 345.26 (100). MS (ES−): m/e 344.26 (20), 343.25 (100).

Compound 78

3-[4-(4-Trifluoromethyl-phenyl)-pyrimidin-2-yl]-benzoic acid: m.p. 271-273° C. $^1$H NMR (300 MHz, DMSO-d$_6$): δ 9.04 (2H, m), 8.72 (1H, dd, J=7.7, 1.0 Hz), 8.49 (2H, d, J=8.3 Hz), 8.10 (2H, m), 7.93 (2H, d, J=8.3 Hz), 7.68 (1H, t, J=7.4 Hz). MS (ES+): m/e 346.26 (20), 345.26 (100). MS (ES−): m/e 344.22 (20), 343.24 (100).

Compound 79

3-[4-(4-Imidazol-1-yl-phenyl)-pyrimidin-2-yl]-benzoic acid: m.p. >310° C. $^1$H NMR (300 MHz, DMSO-d$_6$): δ 9.64 (1H, s), 9.03 (2H, m), 8.73 (1H, dd, J=7.8, 1.0 Hz), 8.52 (2H, d, J=8.3 Hz), 8.32 (1H, s), 8.15 (4H, m), 7.70 (2H, m). MS (ES+): m/e 344.30 (20), 343.30 (100). MS (ES−): m/e 342.27 (20), 341.27 (100).

Compound 57

4-[4-(3,4-Dimethoxy-phenyl)-pyrimidin-2-yl]-benzoic acid: m.p. 250-252° C. $^1$H NMR (300 MHz, DMSO-d$_6$): δ 8.89 (1H, d, J=5.5 Hz), 8.59 (2H, d, J=8.5 Hz), 8.10 (2H, d, J=8.5 Hz), 8.01 (1H, d, J=5.5 Hz), 7.93 (1H, d, J=8.5 Hz), 7.88 (1H, s), 7.12 (1H, d, J=8.5 Hz), 3.90 (3H, s), 3.84 (3H, s). MS (ES+): m/e 338.27 (20), 337.22 (100). MS (ES−): m/e 336.26 (20), 335.26 (100).

Compound 58

3-[4-(3,4-Dimethoxy-phenyl)-pyrimidin-2-yl]-benzoic acid: m.p. 240-243° C. $^1$H NMR (300 MHz, DMSO-d$_6$): δ 8.90 (1H, d, J=5.2 Hz), 8.60 (2H, m), 8.09 (2H, m), 8.02 (1H, d, J=5.2 Hz), 7.86 (1H, dd, J=8.5, 1.3 Hz), 7.70 (1H, s), 7.14 (1H, dd, J=8.3, 1.2 Hz), 3.91 (3H, s), 3.84 (3H, s). MS (ES+): m/e 338.28 (20), 337.25 (100). MS (ES−): m/e 336.27 (20), 335.26 (100).

Compound 59

4-[4-(4-Dimethylamino-phenyl)-pyrimidin-2-yl]-benzoic acid: m.p. 292-295° C. 1H NMR (300 MHz, DMSO-d$_6$): δ 8.78 (1H, d, J=5.5 Hz), 8.58 (2H, d, J=8.5 Hz), 8.21 (2H, d, J=9.1 Hz), 8.09 (2H, d, J=8.5 Hz), 7.85 (1H, d, J=5.5 Hz), 6.84 (2H, d, J=9.1 Hz), 3.02 (6H, s). MS (ES+): m/e 321.32 (20), 320.30 (100). MS (ES−): m/e 319.33 (20), 318.30 (100).

Compound 60

3-[4-(4-Dimethylamino-phenyl)-pyrimidin-2-yl]-benzoic acid: m.p. 281-283° C. MS (ES+): m/e 321.32 (50), 320.30 (100). MS (ES−): m/e 319.33 (20), 318.29 (100).

Preparation of 4-[4-Methyl-6-(4-trifluoromethyl-phenyl)-pyrimidin-2-yl]-benzoic acid (Compound 52) [PTC-0169003]

Part A. To a 10 mL microwave tube is added 4-trifluoromethylacetophenone (0.95 g, 7.32 mmol) and dimethylacetamide dimethyl acetal (1.60 g, 12.01 mmol). The tube is heated to 140° C. at 250 psi, 300 W for 30 min. A white solid is precipitated by addition of hexanes. The desired product (290.1 mg, 22.1% yield) is collected by filtration and washed with hexanes. The obtained compound, 3-dimethylamino-1-(4-trifluoromethyl-phenyl)-but-2-en-1-one, is >90% pure as determined by LC-MS. MS (ES+): m/e 258.20.

Part B. To a mixture of 3-dimethylamino-1-(4-trifluoromethyl-phenyl)-but-2-en-1-one (290.1 mg, 1.13 mmol), 4-carbamimidoyl-benzoic acid tert-butyl ester (220.3 mg, 1.00 mmol, prepared by the same manner as 3-carbamimidoyl-benzoic acid tert-butyl ester) and sodium hydride (79.9 mg, 2.00 mmol, 60% in hexanes) is added dry ethanol (5.0 mL). The resulting mixture is stirred at refluxing for 14 h until complete consumption of the starting material is determined by TLC. The solvent is removed, and the residue is neutralized with 1N HCl until pH <7 to precipitate a white solid, which is collected by filtration followed by washing with water and ethyl ether/hexanes (1:1). The obtained solid is further purified by flash column chromatography, eluting with methanol/methylene chloride (1:40), to give the title product (10.7 mg, 2.7% yield), m.p. 272-275° C. $^1$H NMR (300 MHz, CDCl$_3$+2 drops DMSO-d$_6$): δ 8.54 (2H, d, J=8.3 Hz), 8.23 (2H, d, J=8.6 Hz), 8.09 (2H, d, J=8.3 Hz), 7.71 (2H, d, J=8.6 Hz), 7.48 (1H, s), 2.61 (3H, s). MS (ES+): m/e 359.27.

The following compound may be prepared in a similar manner to that described above with reference to Compound 52.

Compound 56

3-[4-(4-Fluoro-phenyl)-6-methyl-pyrimidin-2-yl]-benzoic acid: m.p. 305-307° C. $^1$H NMR (300 MHz, DMSO-d$_6$): δ 8.60 (2H, d, J=8.0 Hz), 8.41 (2H, m), 8.08 (2H, d, J=8.0 Hz), 7.96 (1H, s), 7.41 (2H, m), 2.60 (3H, s). MS (ES+): m/e 310.34 (20), 309.34 (100). MS (ES-): m/e 308.30 (20), 307.32 (100).

Preparation of 3-[4-(4-Fluoro-phenyl)-5-methyl-pyrimidin-2-yl]-benzoic acid (Compound 55)

Part A. A mixture of 4-fluoropropiophenone (1.83 g, 10.60 mmol) and N,N-dimethylformamide dimethyl acetal (4.45 g, 37.35 mmol) is heated to reflux for 16 h. The residue obtained after removal of the solvent (containing 3-dimethylamino-1-(4-fluoro-phenyl)-propan-1-one) is used for the next step without purification.

Part B. A mixture of 3-dimethylamino-1-(4-fluoro-phenyl)-propan-1-one (641.9 mg, 3.10 mmol) and 3-carbamimidoyl-benzoic acid tert-butyl ester (426.1 mg, 1.91 mmol) in anhydrous acetic acid (8 mL) is heated to 130° C. at 300 W, 250 psi in a microwave reactor for 30 min. A white solid is precipitated by addition of 1 N HCl, and collected by filtration, followed by washing with water and hexanes. The obtained solid is further purified by flash column chromatography, eluting with methanol/methylene chloride (1:40) to afford the title product (114.1 mg, 12.0% yield), m.p. 272-275° C. $^1$H NMR (300 MHz, DMSO-d$_6$): δ 8.50 (2H, d, J=8.0 Hz), 8.06 (2H, d, J=8.0 Hz), 7.85 (2H, m), 8.13 (2H, m), 7.38 (2H, m), 2.40 (3H, s). MS (ES+): m/e 309.34.

The following compound may be prepared in a similar manner to that described above with reference to Compound 55.

Compound 54

3-[4-(2-Fluoro-phenyl)-5-methyl-pyrimidin-2-yl]-benzoic acid: m.p. 279-281° C. $^1$H NMR (300 MHz, DMSO-d$_6$): δ 8.92 (1H, s), 8.46 (2H, m), 8.05 (2H, m), 7.43 (2H, m), 7.38 (2H, m), 2.22 (3H, s). MS (ES+): m/e 310.29 (20), 309.27 (100). MS (ES-): m/e 308.29 (20), 307.27 (100).

E. Preparation of 2,4-Pyridines

The 2,4 pyridines of Formulas 1-E and 2-E may generally be prepared according to Scheme E as follows.

Preparation of 3-[4-(4-Isopropyl-phenyl)-pyridin-2-yl]-benzoic acid (Compound 7)

Part A. A solution of 4-bromopyridine hydrochloride (1.0 g, 6.3 mmol) in acetonitrile-water (50 mL/20 mL) is treated with 4-isopropylbenzeneboronic acid (1.04 g, 6.3 mmol) and sodium carbonate (2.1 g, 25.2 mmol). The mixture is degassed twice, and a catalytic quantity of tetrakis(triphenylphosphine)palladium is added. The mixture is heated to reflux for 12 h., then cooled and poured into water (50 mL). The mixture is filtered and extracted with ethyl acetate (3×50 mL). The extracts are combined, washed with brine, dried over magnesium sulfate, filtered and evaporated to afford 1.01 g of sufficiently pure product, 4-(4-isopropyl-phenyl)-pyridine.

Part B. A solution of 4-(4-isopropyl-phenyl)-pyridine (1.01 g, 5.1 mmol) in dichloromethane (20 mL) is cooled to 0° C., and a solution of m-chloroperoxybenzoic acid (1.33 g, 7.6 mmol) in dichloromethane (20 mL) is added dropwise. The mixture is allowed to warm to ambient temperature over 12 h. with stirring, then heated to reflux for 2 h. An excess of m-chloroperoxybenzoic acid (0.5 g) is added, and reflux continued for 2 h. The solution is cooled and washed successively with 10% aq. sodium sulfite, 10% aq. sodium carbonate and saturated brine. The organic phase is dried over anhydrous magnesium sulfate and evaporated. The residue is separated by flash chromatography to afford 4-(4-isopropyl-phenyl)-pyridine-N-oxide (0.85 g, 78%).

Part C. A mixture of 4-(4-isopropyl-phenyl)-pyridine-N-oxide (126 mg, 0.59 mmol) and phosphorus oxychloride (5 mL) is heated to reflux for 12 h. The mixture is cooled and evaporated, and the residue is dissolved in water, neutralized with satd. aq. Na$_2$CO$_3$ and extracted with ethyl acetate. The extract is washed with brine, dried over magnesium sulfate, filtered and evaporated. The residue is separated by column chromatography to afford 2-chloro-4-(4-isopropyl-phenyl)-pyridine (110 mg, 81%).

Part D. A solution of 2-chloro-4-(4-isopropyl-phenyl)-pyridine (110 mg, 0.48 mmol) in acetonitrile-water (1 mL/0.5 mL) is treated with 3-carboethoxybenzeneboronic acid (186 mg, 0.96 mmol), sodium carbonate (153 mg, 1.44 mmol) and tetrakis(triphenylphosphine)palladium (cat. amount). The mixture is heated to reflux for 12 h., then cooled and partitioned between water and ethyl acetate. The organic phase is washed with brine, dried over magnesium sulfate, filtered and evaporated. The residue is separated by column chromatography to afford ethyl 3-[4-(4-isopropyl-phenyl)-pyridin-2-yl]-benzoate (116 mg, 70%).

Part E. A solution of ethyl 3-[4-(4-isopropyl-phenyl)-pyridin-2-yl]-benzoate (116 mg, 0.34 mmol) in methanol-water (3 mL/1 mL) is treated with lithium hydroxide hydrate (41 mg, 1.7 mmol). The mixture is stirred at ambiemperature for 12 h., then partitioned between water and diethyl ether. The aqueous phase is neutralized to pH 7 with 3 N aq. HCl and extracted with ethyl acetate. The extract is washed with brine, dried over magnesium sulfate, filtered and evaporated to afford the title compound as a white powder (92 mg, 85%), m.p. 233-234° C. $^1$H NMR (300 MHz, methanol-d$_4$): δ 8.66 (1H, s), 8.65 (1H, d, J=8 Hz), 8.25 (1H, d, J=8 Hz), 8.14-8.11 (2H, m), 7.78 (2H, d, J=9 Hz), 7.69-7.62 (2H, m), 7.42 (2H, d, J=9 hz), 3.00 (1H, heptet, J=7 Hz), 1.30 (6H, d, J=7 Hz). MS (ES+): m/e x. MS (ES-): m/e 319 (20), 318 (100).

The following compound may be prepared in a similar manner to that described above with reference to Compound 7.

Compound 13

4-(4-p-Tolyl-pyridin-2-yl)-benzoic acid: m.p. 288-291° C. $^1$H NMR (300 MHz, DMSO-d$_6$): δ 8.78 (1H, d, J=7 Hz), 8.42 (1H, s), 8.30 (2H, d, J=9 Hz), 8.08 (2H, d, J=9 Hz), 7.94-7.90 (3H, m), 7.38 (2H, d, J=9 Hz), 2.39 (3H, s). MS (ES+): m/e 291 (19), 290 (100).

F. 3,5-Pyridines

The 3,5 pyridines of Formulas 1-F and 2-F may generally be prepared according to Scheme F as follows.

Preparation of 3-[5-(4-Isopropyl-phenyl)-pyridin-3-yl]-benzoic acid (Compound 11)

Part A. A solution of 3,5-dibromopyridine (1.0 g, 4.2 mmol) and 4-isopropylbenzeneboronic acid (346 mg, 2.1 mmol) in a mixture of ethanol-toluene-water (10 mL/5 mL/3 mL) is treated with sodium carbonate (450 mg). The mixture is degassed twice, treated with a catalytic amount of tetrakis(triphenylphosphine)palladium, and heated with stirring to 80° C. for 12 h. The mixture is cooled, filtered and evaporated. The residue is partitioned between water and ethyl acetate, and the organic phase is washed with brine, dried over sodium sulfate, filtered and evaporated. The residue is separated by column chromatography to afford 3-bromo-5-(4-isopropyl-phenyl)-pyridine (300 mg, 55%).

Part B. A solution of 3-bromo-5-(4-isopropyl-phenyl)-pyridine (300 mg, 1.1 mmol) and 3-carboethoxybenzeneboronic acid (180 mg, 1.1 mmol) in ethanol-toluene-water (10 mL/5 mL/3 mL) is treated with sodium carbonate (345 mg), degassed twice and treated with a catalytic quantity of tetrakis(triphenylphosphine)palladium. The mixture is heated to 80° C. with stirring until the starting material is consumed as determined by TLC. Then, the mixture is cooled, filtered and evaporated, and the residual material is partitioned between water and ethyl acetate. The organic phase is washed with brine, dried over sodium sulfate, filtered and evaporated, and the residue is separated by column chromatography to afford ethyl 3-[5-(4-isopropyl-phenyl)-pyridin-3-yl]-benzoate (252 mg, 79%).

Part C. A solution of ethyl 3-[5-(4-isopropyl-phenyl)-pyridin-3-yl]-benzoate (100 mg) in methanol-water (3 mL/1 mL) is treated with lithium hydroxide hydrate (50 mg), and the solution is heated to 40-50° C. for 12 h. After cooling, the solution is neutralized to pH 7 with 3 N HCl and extracted with ethyl acetate. The extract is washed with brine, dried over sodium sulfate, filtered and evaporated to afford the title compound as a powder (80 mg, 87%), m.p. 155-156° C. $^1$H NMR (300 MHz, CDCl$_3$): δ 8.93-8.90 (2H, m), 8.44 (1H, s), 8.21-8.19 (2H, m), 7.89 (1H, d, J=7 Hz), 7.64 (1H, t, J=8 Hz), 7.61 (2H, d, J=9 Hz), 7.39 (2H, d, J=9 Hz), 3.00 (1H, heptet, J=7 Hz), 1.30 (6H, d, J=7 Hz). MS (ES+): m/e 319 (22), 318 (100).

The following compound may be prepared in a similar manner to that described above with reference to Compound 11.

Compound 15

4-(5-p-Tolyl-pyridin-3-yl)-benzoic acid: m.p. 260-262° C. $^1$H NMR (300 MHz, DMSO-d$_6$): δ 8.92 (2H, s), 8.38 (1H, s), 8.05 (2H, d, J=9 Hz), 7.98 (2H, d, J=9 Hz), 7.75 (2H, d, J=9 Hz), 7.33 (2H, d, J=9 Hz), 2.36 (3H, s). MS (ES+): m/e 291 (20), 290 (100).

G. 4,2-Pyridines

The 4,2 pyridines of Formulas 1-G and 2-G may generally be prepared according to Scheme G as follows.

Preparation of 3-[2-(4-Isopropyl-phenyl)-pyridin-4-yl]-benzoic acid (Compound 8)

Part A. A solution of 4-bromopyridine (1.0 g, 5.2 mmol) in acetonitrile-water (10 mL/5 mL) is treated with 3-carboethoxybenzeneboronic acid (0.93 g, 5.2 mmol), sodium carbonate (2.2 g, 21 mmol) and catalytic tetrakis(triphenylphosphine)palladium. The solution is heated to reflux for 12 h., then cooled and extracted with ethyl acetate. The extract is washed with brine, dried over sodium sulfate, filtered and evaporated. The residual material is separated by flash chromatography to afford ethyl 3-pyridin-4-yl-benzoate (1.0 g, 86%).

Part B. A solution of ethyl 3-pyridin-4-yl-benzoate (150 mg, 0.66 mmol) in dichloromethane (5 mL) is treated with m-chloroperoxybenzoic acid (340 mg, 2.0 mmol). After stirring for 2 days, the mixture is treated with 350 mg more m-chloroperoxybenzoic acid, and the reaction mixture is heated to reflux overnight. The solution is cooled and washed successively with 10% aq. sodium sulfite, 10% aq. sodium carbonate and brine. The organic phase is dried over anhydrous magnesium sulfate, filtered and evaporated to afford sufficiently pure ethyl 3-pyridin-4-yl-benzoate-N-oxide. This material is dissolved in phosphorus oxychloride and heated to reflux for 12 h. The reaction mixture is cooled and evaporated, and the residue is taken up into ethyl acetate. This solution is washed with satd. aq. sodium carbonate, water and brine, then dried over magnesium sulfate, filtered and evaporated. The residue is separated by flash chromatography to afford ethyl 3-(2-chloro-pyridin-4-yl)-benzoate (81 mg, 47% overall).

Part C. A solution of ethyl 3-(2-chloro-pyridin-4-yl)-benzoate (81 mg, 0.31 mmol), sodium carbonate (99 mg, 0.93 mmol) and 4-isopropylbenzeneboronic acid (60 mg) in acetonitrile-water (2 mL/0.5 mL) is treated with a catalytic quantity of tetrakis(triphenylphosphine)palladium, and heated to reflux for 24 h. The mixture is poured into water (60 mL), and this mixture is extracted with diethyl ether (3×60 mL). The extracts are combined, washed with brine, dried over magnesium sulfate, filtered and evaporated to afford ethyl 3-[2-(4-isopropyl-phenyl)-pyridin-4-yl]-benzoate (75 mg, 76%)

Part D. The standard lithium hydroxide ester hydrolysis method is used to convert ethyl 3-[2-(4-isopropyl-phenyl)-pyridin-4-yl]-benzoate to the title compound, m.p. 247-249° C. $^1$H NMR (300 MHz, CDCl$_3$): δ 8.80 (1H, d, J=8 Hz), 8.45 (1H, s), 8.21 (1H, d, J=8 hz), 7.99 (2H, d, J=9 Hz), 7.98-7.94 (2H, m), 7.64 (1H, t, J=8 Hz), 7.52-7.48 (1H, m), 7.37 (2H, d, J=9 Hz), 2.99 (1H, heptet, J=7 Hz), 1.30 (6H, d, J=7 Hz). MS (ES+): m/e 319 (24), 318 (100).

The following compound may be prepared in a similar manner to that described above with reference to Compound 8.

Compound 12

4-(2-p-Tolyl-pyridin-4-yl)-benzoic acid: m.p. 286-289° C. $^1$H NMR (300 MHz, CDCl$_3$): δ 8.71 (1H, br d, J=6 Hz), 8.22 (1H, s), 8.12-8.02 (6H, m), 7.30 (2H, d, J=9 Hz), 2.36 (3H, s). MS (ES+): m/e 291 (20), 290 (100).

H. 2,6-Pyridines

The 4,2 pyridines of Formulas 1-H and 2-H may generally be prepared according to Scheme H as follows.

Preparation of 3-[6-(4-Isopropyl-phenyl)-pyridin-2-yl]-benzoic acid (Compound 6)

Part A. A solution of 2,6-dibromopyridine (6.16 g, 26 mmol) and 3-carboethoxybenzeneboronic acid (0.5 g, 2.6 mmol) in acetonitrile (20 mL) is treated with a solution of sodium carbonate (0.88 g) in water (5 mL). The mixture is degassed twice, and a catalytic amount of tetrakis(triphenylphosphine)palladium is added. The reaction mixture is heated to 80° C. and stirred for 12 h., then cooled, filtered and evaporated. The residue is partitioned between water and ethyl acetate, and the organic phase is washed with satd. aq. brine, dried over sodium sulfate, filtered and evaporated. The residual material is separated by column chromatography to give ethyl 3-(6-bromo-pyridin-2-yl)-benzoate (154 mg, 20%).

Part B. A solution of ethyl 3-(6-bromo-pyridin-2-yl)-benzoate (154 mg, 0.5 mmol) and 4-isopropylbenzeneboronic acid (83 mg, 0.5 mmol) in acetonitrile is treated with a solution of sodium carbonate (160 mg) in water (1 mL). The mixture is degassed twice, and a catalytic amount of tetrakis(triphenylphosphine)palladium is added under the protection of nitrogen. The reaction mixture is stirred at 80° C. until the consumption of starting material is observed by TLC. The mixture is cooled, filtered and evaporated, and the residual material is partitioned between water and ethyl acetate. The organic phase is washed with brine, dried over sodium sulfate, filtered and evaporated. The residue is purified by column chromatography to afford ethyl 3-[6-(4-isopropyl-phenyl)-pyridin-2-yl]-benzoate (120 mg, 69%).

Part C. A solution of ethyl 3-[6-(4-isopropyl-phenyl)-pyridin-2-yl]-benzoate (90 mg) in 3 mL methanol-1 mL water is treated with lithium hydroxide hydrate (50 mg). The solution is heated to between 40 and 50° C. for 12 h. with stirring, then cooled and neutralized to pH 7 with 3 N aq. HCl. The mixture is extracted with ethyl acetate, and the extract is washed with brine, dried over sodium sulfate, filtered and evaporated to afford the title product as a powder (70 mg, 85%), m.p. 215-216° C. NMR (300 MHz, CDCl$_3$): δ 8.86 (1H, s), 8.47 (1H, d, J=8 Hz), 8.18 (1H, d, J=8 Hz), 8.08 (2H, d, J=9 Hz), 7.85 (1H, t, J=7 Hz), 7.77 (1H, d, J=7 Hz), 7.76 (1H, d, J=7 Hz), 7.62 (1H, t, J=8 Hz), 7.38 (2H, d, J=9 Hz), 2.99 (1H, heptet, J=7 Hz), 1.30 (6H, d, J=7 Hz). MS (ES+): m/e 319 (20), 318 (100).

The following compound may be prepared in a similar manner to that described above with reference to Compound 6.

Compound 14

4-(6-p-Tolyl-pyridin-2-yl)-benzoic acid: m.p. 283-284° C.

Preparation of 3-(6-Phenyl-pyridin-2-yl)-benzoic acid (Compound 24)

Part A. A suspension of methyl 4-acetylbenzoate (5.00 g, 28.1 mmol) in ethanol (50 mL) is treated with bis(dimethylamino)-methoxymethane (7.50 mL, 56.1 mmol), and the mixture is heated to 80° C. with stirring for 2 days. The solvents are removed under reduced pressure and the desired product (methyl 4-(3-dimethylamino-acryloyl)-benzoate) is obtained as a white solid.

Part B. A solution of (methyl 4-(3-dimethylamino-acryloyl)-benzoate) (100 mg) in acetic acid (5 mL) is treated with acetophenone and ammonium acetate (77 mg). The resulting mixture is heated to 80° C. for 18 h, then cooled and evaporated under a stream of nitrogen. The resulting solid is recrystallized in ethyl acetate-hexane to afford methyl 3-(6-phenyl-pyridin-2-yl)-benzoate. MS (ES+): m/e 290.2 (100).

Part C. Methyl 3-(6-phenyl-pyridin-2-yl)-benzoate is saponified using sodium hydroxide, and workup afforded the acid title product. MS (ES+): m/e 276 (100).

Melting point and mass spec data for certain preferred compounds of the invention are presented in the table below.

| Compound | Melting Point ° C. | Mass Spec (ES+) |
|---|---|---|
| 1 | | 273 |
| 2 | 211-213 | 291.58 |
| 3 | 201-203 | 291 |

-continued

| Compound | Melting Point ° C. | Mass Spec (ES+) |
|---|---|---|
| 4 | 167-169 | 318 |
| 5 | 262-264 | 317 |
| 6 | 215-216 | 318 |
| 7 | 233-234 | 318 |
| 8 | 247-249 | 318 |

-continued
| Compound | Melting Point ° C. | Mass Spec (ES+) |
|---|---|---|
| 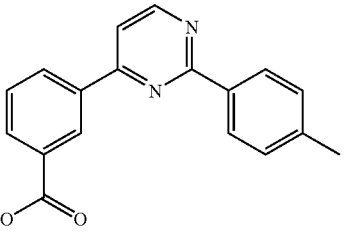 9 | 225-226 | 289 |
| 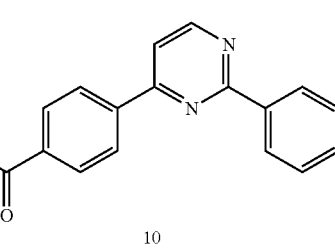 10 | >310 | 289 |
| 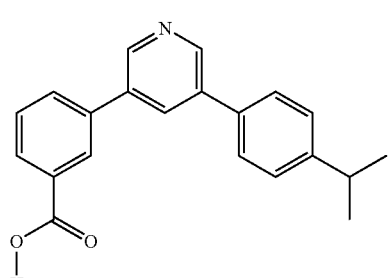 11 | 155-156 | 318 |
| 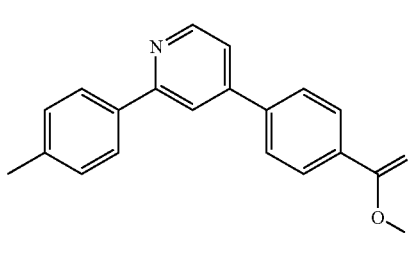 12 | 286-289 | 290 |
| 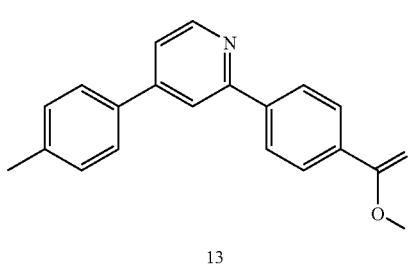 13 | 288-291 | 290 |
| 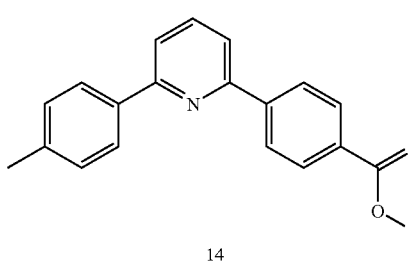 14 | 283-284 | |

-continued
| Compound | Melting Point ° C. | Mass Spec (ES+) |
|---|---|---|
| 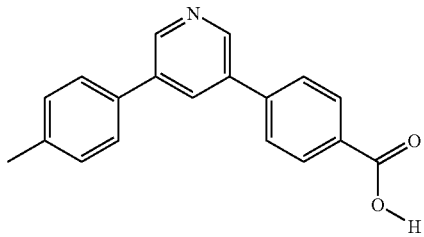 [SMILES: Cc1ccc(-c2cncc(-c3ccc(C(=O)O)cc3)c2)cc1] 15 | 260-262 | 290 |
| 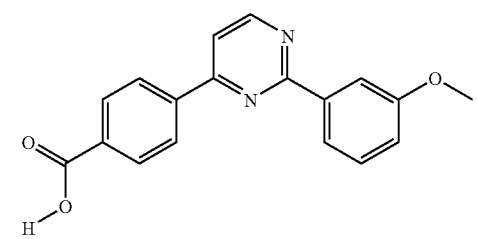 [SMILES: COc1cccc(-c2nccc(-c3ccc(C(=O)O)cc3)n2)c1] 16 | 270-273 | 305 |
| 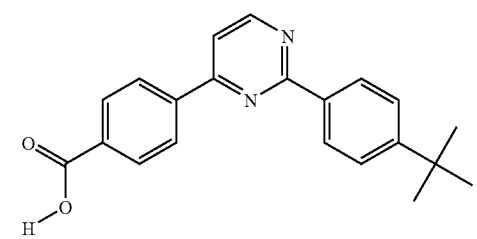 [SMILES: CC(C)(C)c1ccc(-c2nccc(-c3ccc(C(=O)O)cc3)n2)cc1] 17 | 293-296 | 333 |
| 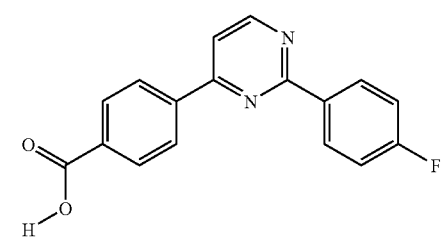 [SMILES: O=C(O)c1ccc(-c2ccnc(-c3ccc(F)cc3)n2)cc1] 18 | >300 | 295 |
| 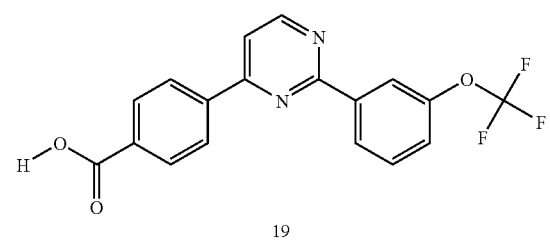 19 | >300 | 361 |
| 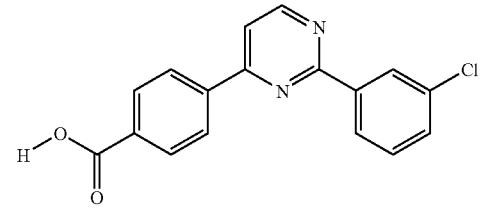 [SMILES: O=C(O)c1ccc(-c2ccnc(-c3cccc(Cl)c3)n2)cc1] 20 | 291-294 | 311 |

-continued
| Compound | Melting Point °C. | Mass Spec (ES+) |
|---|---|---|
| 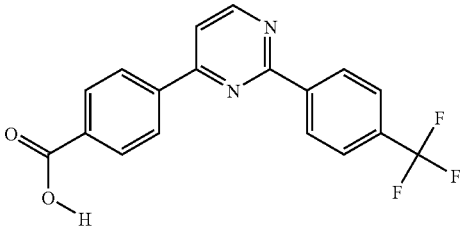 [SMILES: O=C(O)c1ccc(-c2ccnc(-c3ccc(C(F)(F)F)cc3)n2)cc1] 21 | >300 | 345 |
| 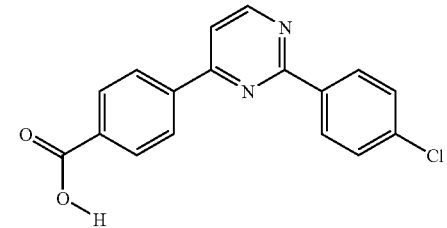 [SMILES: O=C(O)c1ccc(-c2ccnc(-c3ccc(Cl)cc3)n2)cc1] 22 | >300 | 311 |
| 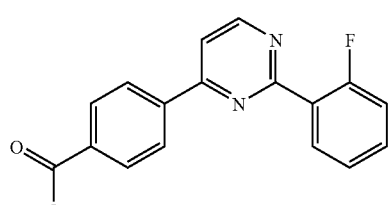 23 | >300 | 295 |
| 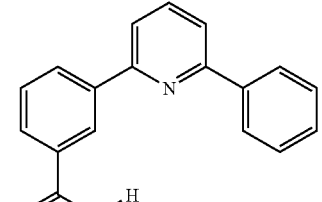 24 | | 276 |
| 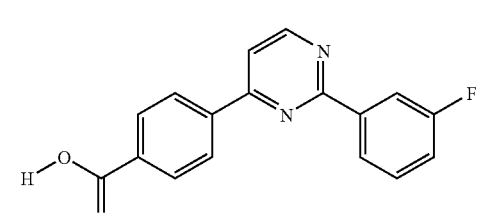 25 | 300-303 | 295 |
| 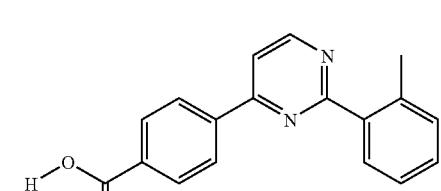 26 | 198-200 | 291 |

-continued
| Compound | Melting Point ° C. | Mass Spec (ES+) |
|---|---|---|
| 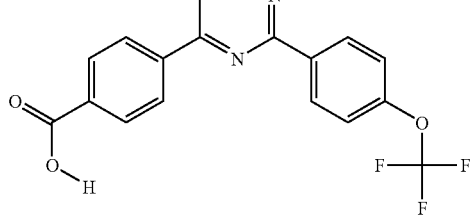
27 | 299-302 | 361 |
| 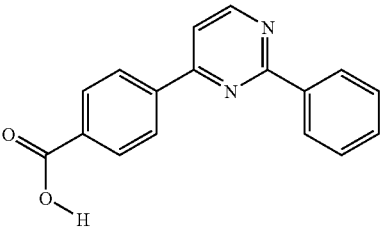 [SMILES: O=C(O)c1ccc(-c2ccnc(-c3ccccc3)n2)cc1]
28 | >300 | 277 |
| 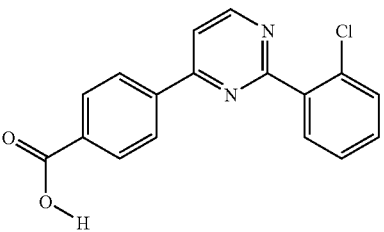
29 | | |
| 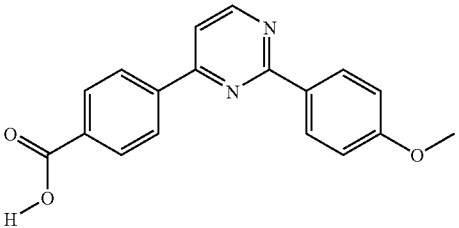 [SMILES: COc1ccc(-c2nccc(-c3ccc(C(=O)O)cc3)n2)cc1]
30 | >300 | 307 |
| 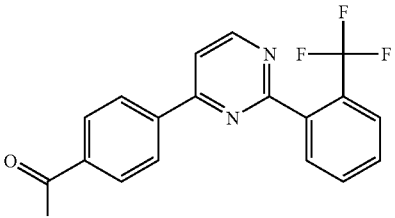
31 | 251-252 | 345 |
| 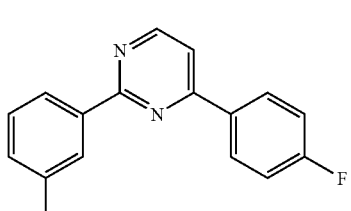
32 | 239-241 | 295 |

-continued
| Compound | Melting Point °C. | Mass Spec (ES+) |
|---|---|---|
| 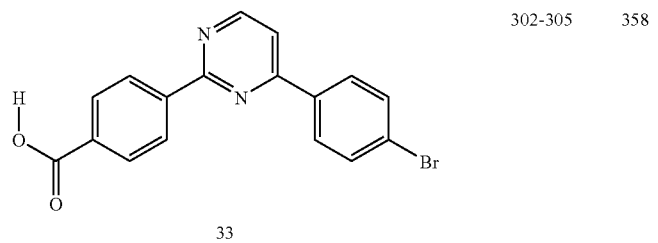 33 | 302-305 | 358 |
| 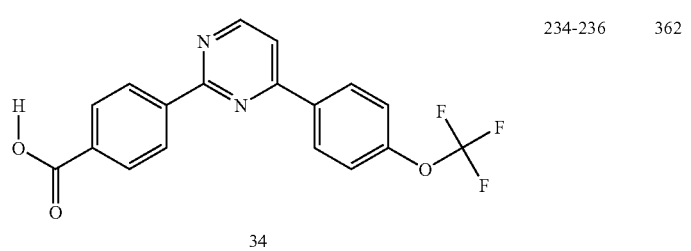 34 | 234-236 | 362 |
| 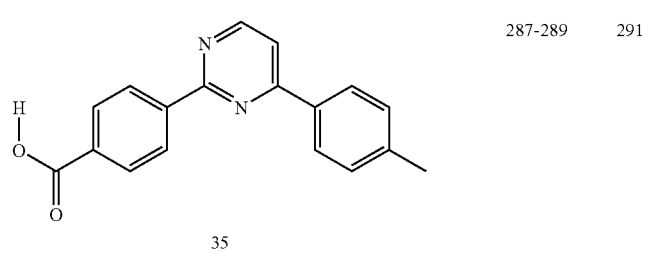 35 | 287-289 | 291 |
| 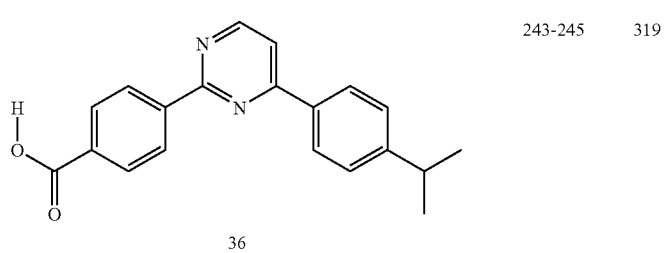 36 | 243-245 | 319 |
| 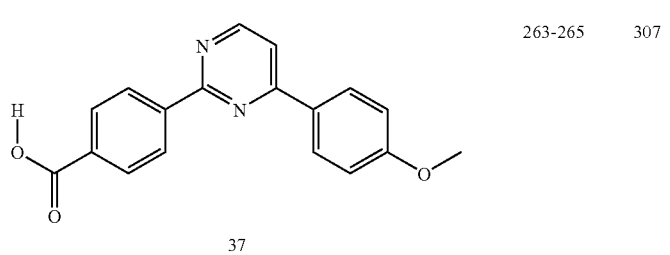 37 | 263-265 | 307 |
| 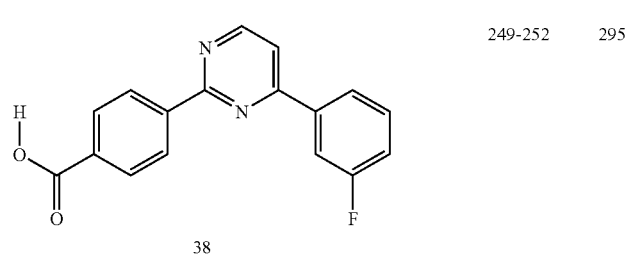 38 | 249-252 | 295 |

-continued

| Compound | Melting Point ° C. | Mass Spec (ES+) |
|---|---|---|
| 39 | 293-296 | 353 |
| 40 | 272-274 | 335 |
| 41 | >305 | 342 |
| 42 | 239-241 | 335 |
| 43 | 298-300 | 292 |
| 44 | 266-269 | 297 |

-continued

| Compound | Melting Point ° C. | Mass Spec (ES+) |
|---|---|---|
| 45 | 269-272 | 322 |
| 46 | 288-290 | 292 |
| 47 | 295-298 | 296 |
| 48 | 307-309 | 308 |
| 49 | 273-276 | 296 |
| 50 | 290-293 | 346 |

-continued
| Compound | Melting Point °C. | Mass Spec (ES+) |
|---|---|---|
| 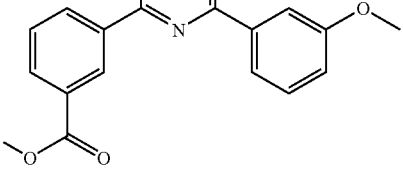<br>51 | 227-229 | 308 |
| 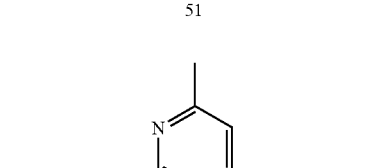<br>52 | 272-275 | 359 |
| 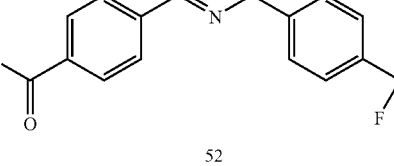<br>53 | >300 | 308 |
| 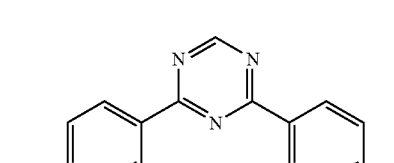<br>54 | 279-281 | 307 |
| <br>55 | 272-275 | 309 |

| Compound | Melting Point ° C. | Mass Spec (ES+) |
|---|---|---|
| 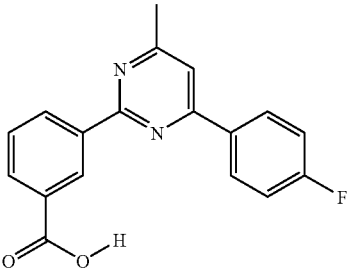 [SMILES: Cc1cc(-c2ccc(F)cc2)nc(-c2cccc(C(=O)O)c2)n1]<br>56 | 305-307 | 307 |
| 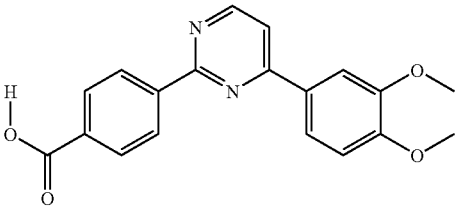<br>57 | 250-252 | 337 |
| 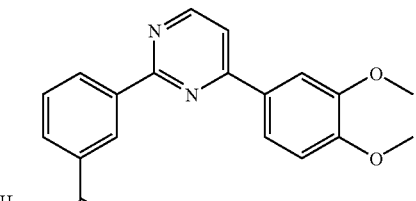<br>58 | 240-243 | 337 |
| 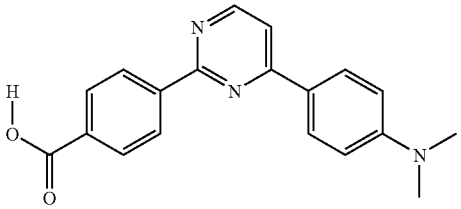 [SMILES: CN(C)c1ccc(-c2ccnc(-c3ccc(C(=O)O)cc3)n2)cc1]<br>59 | 292-295 | 320 |
| 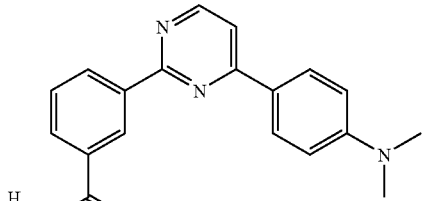<br>60 | 281-283 | 318 |
| 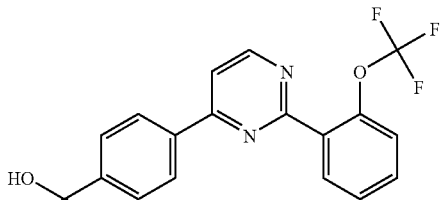<br>61 | 258-261 | 361 |

-continued
| Compound | Melting Point ° C. | Mass Spec (ES+) |
|---|---|---|
| 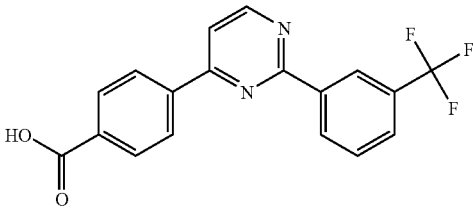 [SMILES: O=C(O)c1ccc(-c2ccnc(-c3cccc(C(F)(F)F)c3)n2)cc1] 62 | | 345 |
| 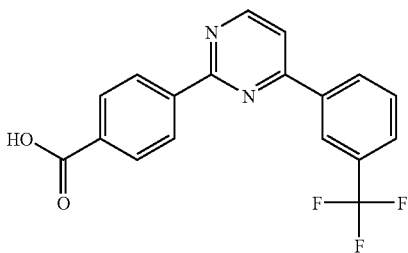 [SMILES: O=C(O)c1ccc(-c2nccc(-c3cccc(C(F)(F)F)c3)n2)cc1] 63 | 271-273 | 345 |
| 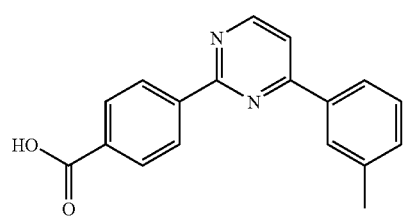 [SMILES: Cc1cccc(-c2ccnc(-c3ccc(C(=O)O)cc3)n2)c1] 64 | 220-222 | 291 |
| 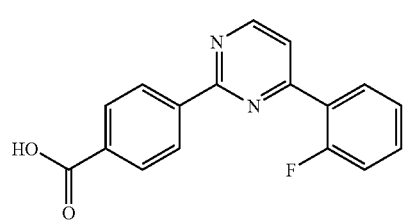 [SMILES: O=C(O)c1ccc(-c2nccc(-c3ccccc3F)n2)cc1] 65 | 234-236 | 295 |
| 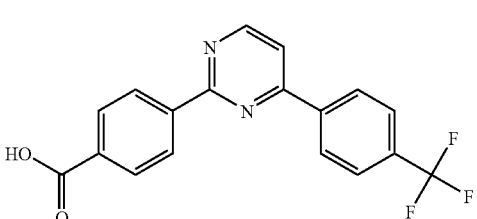 66 | 282-285 | 345 |
| 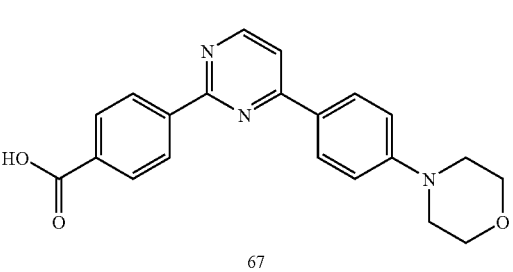 67 | 289-291 | 362 |

-continued

| Compound | Melting Point ° C. | Mass Spec (ES+) |
|---|---|---|
| 68 | >300 | 355 |
| 69 | 241-243 | 361 |
| 70 | 242-244 | 319 |
| 71 | 243-244 | 307 |
| 72 | 201-203 | 295 |
| 73 | 252-253 | 291 |

| Compound | Melting Point ° C. | Mass Spec (ES+) |
|---|---|---|
| 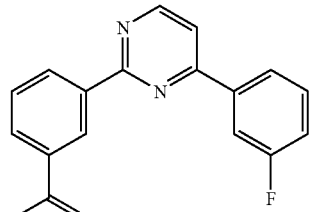 74 | 253-255 | 295 |
| 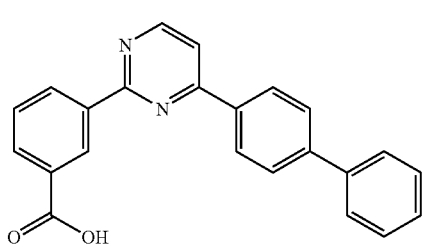 [SMILES: O=C(O)c1cccc(-c2nccc(-c3ccc(-c4ccccc4)cc3)n2)c1] 75 | 296-299 | 353 |
| 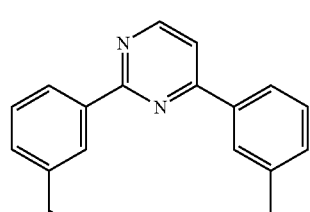 76 | 217-219 | 291 |
| 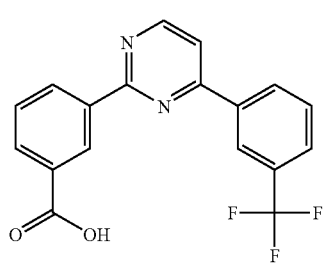 [SMILES: O=C(O)c1cccc(-c2nccc(-c3cccc(C(F)(F)F)c3)n2)c1] 77 | 271-273 | 345 |
| 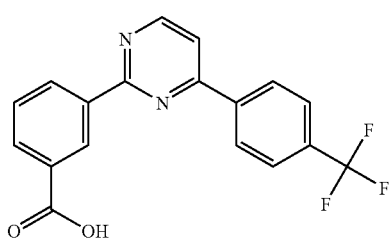 [SMILES: O=C(O)c1cccc(-c2nccc(-c3ccc(C(F)(F)F)cc3)n2)c1] 78 | 271-273 | 345 |
| 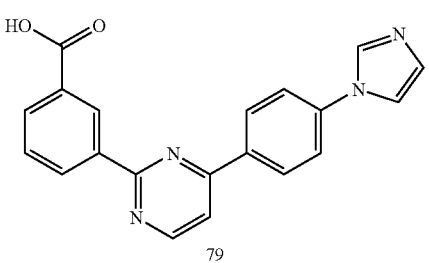 79 | >310 | 343 |

-continued

| Compound | Melting Point ° C. | Mass Spec (ES+) |
|---|---|---|
| 80 | 298-300 | 292.30 |
| 81 | 266-269 | 296.28 |
| 82 | 269-272 | 322.27 |
| 83 | >300 | 308.26 |
| 84 | 227-229 | 308.26 |
| 85 | 290-293 | 346.22 |

-continued

| Compound | Melting Point ° C. | Mass Spec (ES+) |
|---|---|---|
| 86 | 273-276 | 296.25 |
| 87 | 307-309 | 308.26 |
| 88 | 295-298 | 296.22 |
| 89 | 288-290 | 292.30 |

Example 2

Nonsense Suppression Activity

A functional, cell-based translation assay based on luciferase-mediated chemoluminescence (International Application PCT/US2003/023185, filed on Jul. 23, 2003, hereby incorporated by reference in its entirety) permits quantitative assessment of the level of nonsense suppression. Human embryonic kidney cells (293 cells) are grown in medium containing fetal bovine serum (FBS). These cells can be stably transfected with the luciferase gene containing a premature termination codon at amino acid position 190. In place of the threonine codon (ACA) normally present in the luciferase gene at this site, each of the 3 possible nonsense codons (TAA, TAG, or TGA) and each of the 4 possible nucleotides (adenine, thymine, cytosine, or guanine) at the contextually important downstream +1 position following the nonsense codon are introduced by site-directed mutagenesis. As such, amino acid 190 in the luciferase gene containing a premature termination codon is either TAA, TAG, or TGA. For each stop codon, the nucleotide following amino acid 190 of luciferase gene containing a premature termination codon can be replaced with an adenine, thymine, cytosine, or guanine (A, T, C, G) such that these mutations do not change the reading frame of the luciferase gene. Schematics of these constructs are depicted in FIG. 1.

The nonsense suppression activity from a cell-based luciferase reporter assay of the present invention as described above shown in the table below (Table 2). Human Embryonic Kidney 293 cells are stably transfected with a luciferase reporter construct comprising a UGA nonsense mutation at position 190, which is followed, in-frame by an adenine nucleotide.

Activity measurements in Table 2 are determined in a cell-based luciferase reporter assay of the present invention construct containing a UGA premature termination codon. Gentamicin, an aminoglycoside antibiotic known to allow readthrough of premature termination codons, is used as an internal standard. Activity measurements are based on the qualitative ratio between the minimum concentration of compound required to produce a given protein in a cell versus the amount of protein produced by the cell at that concentration. Compounds which are found to have either or both very high potency and very high efficacy of protein synthesis are classified as "***". Compounds which are found to have intermediate potency and/or efficacy of protein synthesis are classified as ""; "*"; or "**". Similarly, compounds which are found to have lower potency and/or efficacy of protein synthesis are classified as "*".

| Compound | UGA |
|---|---|
| 1 | * |
| 2 | *** |
| 3 | ** |
| 4 | * |
| 5 | ** |
| 6 | *** |
| 7 | ** |
| 8 | * |
| 9 | *** |
| 10 | ***** |
| 11 | ** |
| 12 | *** |
| 13 | **** |
| 14 | **** |
| 15 | *** |
| 16 | ** |
| 17 | *** |
| 18 | * |
| 19 | * |
| 20 | *** |
| 21 | *** |
| 22 | * |
| 23 | ** |
| 24 | *** |
| 25 | * |
| 26 | ** |
| 27 | *** |
| 28 | * |
| 29 | * |
| 30 | ** |
| 31 | * |
| 32 | ** |
| 33 | *** |
| 34 | *** |
| 35 | ***** |
| 36 | *** |
| 37 | **** |
| 38 | * |
| 39 | ** |
| 40 | **** |
| 41 | * |
| 42 | ***** |
| 43 | **** |
| 44 | * |
| 45 | *** |
| 46 | *** |
| 47 | ** |
| 48 | *** |
| 49 | ** |
| 50 | *** |
| 51 | *** |
| 52 | *** |
| 53 | *** |
| 54 | ** |
| 55 | **** |
| 56 | ***** |
| 57 | *** |
| 58 | ** |
| 59 | *** |
| 60 | **** |
| 61 | * |
| 62 | * |
| 63 | ***** |
| 64 | **** |
| 65 | *** |
| 66 | ***** |
| 67 | * |
| 68 | * |
| 69 | * |
| 70 | ** |
| 71 | ** |
| 72 | * |
| 73 | ** |
| 74 | ** |
| 75 | ** |
| 76 | ***** |
| 77 | *** |
| 78 | * |
| 79 | * |
| 80 | **** |
| 81 | * |
| 82 | *** |
| 83 | *** |
| 84 | *** |
| 85 | *** |
| 86 | ** |
| 87 | *** |
| 88 | ** |
| 89 | *** |

The nonsense suppression activity in an assay as described above is shown in the Table 3 below, for a construct with a UAG nonsense mutation at position 190, followed by an adenine nucleotide in-frame, (UAGA); and a construct with a UAA nonsense mutation at position 190, followed by an adenine nucleotide in-frame, (UAAA). "POS WB" indicates that a positive signal is produced on a western blot when the compound of the invention is used in an assay of the present invention harboring a UGA nonsense mutation, followed by a cytosine nucleotide (UGAC).

TABLE 3

| Compound No. | UGAC | UAG | UAA |
|---|---|---|---|
| 33 |  | * | ** |
| 35 |  | * | * |
| 43 |  | * |  |
| 44 |  | * |  |
| 45 |  | * |  |
| 46 |  | * | * |
| 47 |  | * | * |
| 48 |  | * | * |
| 49 |  | * | * |
| 50 | POSWB | * | * |
| 51 | POSWB | * | * |
| 52 |  | * | * |
| 53 |  | * | * |
| 56 |  | * | * |
| 60 |  | * | * |

Example 3

Readthrough Assay

A functional, cell-based translation assay based on luciferase-mediated chemoluminescence (International Application PCT/US2003/023185, filed on Jul. 23, 2003 and incorporated by reference in its entirety) permits assessment of translation-readthough of the normal stop codon in a mRNA. Human embryonic kidney cells (293 cells) are grown in medium containing fetal bovine serum (FBS). These cells are stably transfected with the luciferase gene containing a premature termination codon at amino acid position 190. In place of the threonine codon (ACA) normally present in the luciferase gene at this site, each of the 3 possible nonsense codons (TAA, TAG, or TGA) and each of the 4 possible nucleotides (adenine, thymine, cytosine, or guanine) at the contextually important downstream +1 position following the nonsense codon are introduced by site-directed mutagenesis. As such, amino acid 190 in the luciferase gene containing a premature termination codon is TAA, TAG, or TGA. For each stop codon, the nucleotide following amino acid 190 of luciferase gene containing a premature termination codon are replaced with an adenine, thymine, cytosine, or guanine (A, T, C, G) such that these mutation do not change the reading frame of the luciferase gene. Schematics of these constructs are depicted above in FIG. 1.

Another assay of the present invention can evaluate compounds that promote nonsense mutation suppression. The luciferase constructs described above in FIG. 1 are engineered to harbor two epitope tags in the N-terminus of the luciferase protein. Based on luciferase protein production, these constructs qualitatively assess the level of translation-readthrough. The presence of the full-length luciferase protein produced by suppression of the premature termination codon is measured by immunoprecipitation of the suppressed luciferase protein (using an antibody against a His tag) followed by western blotting using an antibody against the second epitope (the Xpress™ epitope; Invitrogen®; Carlsbad, Calif.). These constructs are depicted in FIG. 2.

Cells that harbor the constructs of FIG. 2 show increased full-length protein production when treated with a compound of the present invention. After treatment for 20 hours, cells containing the constructs of FIG. 2 are collected and an antibody recognizing the His epitope is used to immunoprecipitate the luciferase protein. Following immunoprecipitation, western blotting is performed using the antibody to the Xpress™ epitope (Invitrogen®; Carlsbad, Calif.) to detect the truncated luciferase (produced when no nonsense suppression occurs) and to detect the full-length protein (produced by suppression of the nonsense codon). Treatment of cells with a test compound produces full-length protein and not a readthrough protein (See e.g., FIG. 3). The readthrough protein is produced if suppression of the normal termination codon occurs. Compounds of the present invention suppress the premature, i.e. nonsense mutation, but not the normal termination codon in the luciferase mRNA.

Compounds of the present invention selectively act on premature termination codons but not normal termination codons in mammals.

Rats and dogs are administered high doses of compound (up to 1800 mg/kg) by gavage (oral) once daily for 14 days. After the treatment, tissues are collected, lysates are prepared, and Western blot analysis is performed. Selection of the proteins for evaluation of normal termination codon readthrough is based primarily on the corresponding mRNA having a second stop codon in the 3'-UTR that is in-frame with the normal termination codon. Between these 2 stop codons, each selected protein has an intervening sequence of nucleotides that codes for an extension of the protein in the event of ribosomal readthrough of the first termination codon. If the compound has the capacity to induce nonspecific, ribosomal readthrough, an elongated protein is differentiated from the wild-type protein using Western blot. Tissues are collected from rats and are analyzed for suppression of the normal termination codon (UAA) in the vimentin mRNA. No evidence of suppression is apparent. Tissues are collected from dogs treated with compounds of the present invention. There is no evidence of suppression of the normal termination codon of beta actin, which harbors a UAG stop codon.

In healthy human volunteers, a single dose of a compound of the present invention (200 mg/kg) is administered orally. Blood samples are collected, plasma is prepared, and a Western blot is conducted using plasma samples from female and male subjects. C-reactive protein (CRP), which harbors a UGA termination codon, is used to determine if treatment of subjects with compounds of the present invention result in suppression of the normal termination codon in the CRP mRNA. A luciferase assay in combination with a premature termination assay demonstrates selective suppression of premature termination codons but not normal termination codons.

Example 4

Animal Models

Animal model systems can also be used to demonstrate the safety and efficacy of a compound of the present invention. The compounds of the present invention are tested for biological activity using animal models for a disease, condition, or syndrome of interest. These include animals engineered to contain the target RNA element coupled to a functional readout system, such as a transgenic mouse.

Cystic Fibrosis

Examples of animal models for cystic fibrosis include, but are not limited to, cftr(−/−) mice (see, e.g., Freedman et al., 2001, *Gastroenterology* 121(4):950-7), cftr(tm1HGU/tm1HGU) mice (see, e.g., Bernhard et al., 2001, *Exp Lung Res* 27(4):349-66), CFTR-deficient mice with defective cAMP-mediated Cl(−) conductance (see, e.g., Stotland et al., 2000, *Pediatr Pulmonol* 30(5):413-24), and C57BL/6-Cftr (m1UNC)/Cftr(m1UNC) knockout mice (see, e.g., Stotland et al., 2000, *Pediatr Pulmonol* 30(5):413-24).

Muscular Dystrophy

Examples of animal models for muscular dystrophy include, but are not limited to, mouse, hamster, cat, dog, and *C. elegans*. Examples of mouse models for muscular dystrophy include, but are not limited to, the dy−/− mouse (see, e.g., Connolly et al., 2002, *J Neuroimmunol* 127(1-2):80-7), a muscular dystrophy with myositis (mdm) mouse mutation (see, e.g., Garvey et al., 2002, *Genomics* 79(2):146-9), the mdx mouse (see, e.g., Nakamura et al., 2001, *Neuromuscul Disord* 11(3):251-9), the utrophin-dystrophin knockout (dko) mouse (see, e.g., Nakamura et al., 2001, *Neuromuscul Disord* 11(3):251-9), the dy/dy mouse (see, e.g., Dubowitz et al., 2000, *Neuromuscul Disord* 10(4-5):292-8), the mdx(Cv3) mouse model (see, e.g., Pillers et al., 1999, *Laryngoscope* 109(8):1310-2), and the myotonic ADR-MDX mutant mice (see, e.g., Kramer et al., 1998, *Neuromuscul Disord* 8(8):542-50). Examples of hamster models for muscular dystrophy include, but are not limited to, sarcoglycan-deficient hamsters (see, e.g., Nakamura et al., 2001, *Am J Physiol Cell Physiol* 281(2):C690-9) and the BIO 14.6 dystrophic hamster (see, e.g., Schlenker & Burbach, 1991, *J Appl Physiol* 71(5):1655-62). An example of a feline model for muscular dystrophy includes, but is not limited to, the hypertrophic feline muscular dystrophy model (see, e.g., Gaschen & Burgunder, 2001, *Acta Neuropathol* (Berl) 101(6):591-600). Canine models for muscular dystrophy include, but are not limited to, golden retriever muscular dystrophy (see, e.g., Fletcher et al., 2001, *Neuromuscul Disord* 11(3):239-43) and canine X-linked muscular dystrophy (see, e.g., Valentine et al., 1992, *Am J Med Genet* 42(3):352-6). Examples of *C. elegans* models for muscular dystrophy are described in Chamberlain & Benian, 2000, *Curr Biol* 10(21):R795-7 and Culette & Sattelle, 2000, *Hum Mol Genet* 9(6):869-77.

Familial Hypercholesterolemia

Examples of animal models for familial hypercholesterolemia include, but are not limited to, mice lacking functional LDL receptor genes (see, e.g., Aji et al., 1997, *Circulation* 95(2):430-7), Yoshida rats (see, e.g., Fantappie et al., 1992, *Life Sci* 50(24):1913-24), the JCR:LA-cp rat (see, e.g., Richardson et al., 1998, *Atherosclerosis* 138(1):135-46), swine (see, e.g., Hasler-Rapacz et al., 1998, *Am J Med Genet* 76(5):379-86), and the Watanabe heritable hyperlipidaemic rabbit (see, e.g., Tsutsumi et al., 2000, *Arzneimittelforschung* 50(2):118-21; Harsch et al., 1998, *Br J Pharmacol* 124(2):227-82; and Tanaka et al., 1995, *Atherosclerosis* 114(1):73-82).

Human Cancer

An example of an animal model for human cancer, in general includes, but is not limited to, spontaneously occurring tumors of companion animals (see, e.g., Vail & MacEwen, 2000, *Cancer Invest* 18(8):781-92). Examples of animal models for lung cancer include, but are not limited to, lung cancer animal models described by Zhang & Roth (1994, In Vivo 8(5):755-69) and a transgenic mouse model with disrupted p53 function (see, e.g., Morris et al., 1998, *J La State Med Soc* 150(4):179-85). An example of an animal model for breast cancer includes, but is not limited to, a transgenic mouse that overexpresses cyclin D1 (see, e.g., Hosokawa et al., 2001, *Transgenic Res* 10(5):471-8). An example of an animal model for colon cancer includes, but is not limited to, a TCRbeta and p53 double knockout mouse (see, e.g., Kado et al., 2001, *Cancer Res* 61(6):2395-8). Examples of animal models for pancreatic cancer include, but are not limited to, a metastatic model of Panc02 murine pancreatic adenocarcinoma (see, e.g., Wang et al., 2001, *Int J Pancreatol* 29(1):37-46) and nu-nu mice generated in subcutaneous pancreatic tumours (see, e.g., Ghaneh et al., 2001, *Gene Ther* 8(3):199-208). Examples of animal models for non-Hodgkin's lymphoma include, but are not limited to, a severe combined immunodeficiency ("SCID") mouse (see, e.g., Bryant et al., 2000, *Lab Invest* 80(4):553-73) and an IgHmu-HOX11 transgenic mouse (see, e.g., Hough et al., 1998, *Proc Natl Acad Sci USA* 95(23):13853-8). An example of an animal model for esophageal cancer includes, but is not limited to, a mouse transgenic for the human papillomavirus type 16 E7 oncogene (see, e.g., Herber et al., 1996, *J Virol* 70(3):1873-81). Examples of animal models for colorectal carcinomas include, but are not limited to, Apc mouse models (see, e.g., Fodde & Smits, 2001, *Trends Mol Med* 7(8):369-73 and Kuraguchi et al., 2000, *Oncogene* 19(50):5755-63). An example of an animal model for neurofibromatosis includes, but is not limited to, mutant NF 1 mice (see, e.g., Cichowski et al., 1996, *Semin Cancer Biol* 7(5):291-8). Examples of animal models for retinoblastoma include, but are not limited to, transgenic mice that expression the simian virus 40 T antigen in the retina (see, e.g., Howes et al., 1994, *Invest Ophthalmol Vis Sci* 35(2):342-51 and Windle et al, 1990, *Nature* 343 (6259):665-9) and inbred rats (see, e.g., Nishida et al., 1981, *Curr Eye Res* 1(1):53-5 and Kobayashi et al., 1982, *Acta Neuropathol* (Berl) 57(2-3):203-8). Examples of animal models for Wilm's tumor include, but are not limited to, a WT1 knockout mice (see, e.g., Scharnhorst et al., 1997, *Cell Growth Differ* 8(2):133-43), a rat subline with a high incidence of neuphroblastoma (see, e.g., Mesfin & Breech, 1996, *Lab Anim Sci* 46(3):321-6), and a Wistar/Furth rat with Wilms' tumor (see, e.g., Murphy et al., 1987, *Anticancer Res* 7(4B):717-9).

Retinitis Pigmentosa

Examples of animal models for retinitis pigmentosa include, but are not limited to, the Royal College of Surgeons ("RCS") rat (see, e.g., Vollrath et al., 2001, *Proc Natl Acad Sci USA* 98(22); 12584-9 and Hanitzsch et al., 1998, *Acta Anat* (Basel) 162(2-3):119-26), a rhodopsin knockout mouse (see, e.g., Jaissle et al., 2001, *Invest Ophthalmol Vis Sci* 42(2):506-13), and Wag/Rij rats (see, e.g., Lai et al., 1980, *Am J Pathol* 98(1):281-4).

Cirrhosis

Examples of animal models for cirrhosis include, but are not limited to, $CCl_4$-exposed rats (see, e.g., Kloehn et al., 2001, *Horm Metab Res* 33(7):394-401) and rodent models instigated by bacterial cell components or colitis (see, e.g., Vierling, 2001, *Best Pract Res Clin Gastroenterol* 15(4):591-610).

Hemophilia

Examples of animal models for hemophilia include, but are not limited to, rodent models for hemophilia A (see, e.g., Reipert et al., 2000, *Thromb Haemost* 84(5):826-32; Jarvis et al., 1996, *Thromb Haemost* 75(2):318-25; and Bi et al., 1995, *Nat Genet* 10(1):119-21), canine models for hemophilia A (see, e.g., Gallo-Penn et al., 1999, *Hum Gene Ther* 10(11):1791-802 and Connelly et al, 1998, *Blood* 91(9); 3273-81), murine models for hemophilia B (see, e.g., Snyder et al., 1999, *Nat Med* 5(1):64-70; Wang et al., 1997, *Proc Natl Acad Sci USA* 94(21):11563-6; and Fang et al., 1996, *Gene Ther* 3(3):217-22), canine models for hemophilia B (see, e.g., Mount et al., 2002, *Blood* 99(8):2670-6; Snyder et al., 1999, *Nat Med* 5(1):64-70; Fang et al., 1996, *Gene Ther* 3(3):217-22); and Kay et al., 1994, *Proc Natl Acad Sci USA* 91(6):2353-7), and a rhesus macaque model for hemophilia B (see, e.g., Lozier et al., 1999, *Blood* 93(6):1875-81).

von Willebrand Disease

Examples of animal models for von Willebrand disease include, but are not limited to, an inbred mouse strain RIIIS/J (see, e.g., Nichols et al., 1994, 83(11):3225-31 and Sweeney et al., 1990, 76(11):2258-65), rats injected with botrocetin (see, e.g., Sanders et al., 1988, *Lab Invest* 59(4):443-52), and porcine models for von Willebrand disease (see, e.g., Nichols et al., 1995, *Proc Natl Acad Sci USA* 92(7):2455-9; Johnson & Bowie, 1992, *J Lab Clin Med* 120(4):553-8); and Brinkhous et al., 1991, *Mayo Clin Proc* 66(7):733-42).

β-Thalassemia

Examples of animal models for β-thalassemia include, but are not limited to, murine models with mutations in globin genes (see, e.g., Lewis et al., 1998, *Blood* 91(6):2152-6; Raja et al., 1994, *Br J Haematol* 86(1):156-62; Popp et al., 1985, 445:432-44; and Skow et al., 1983, *Cell* 34(3):1043-52).

Kidney Stones

Examples of animal models for kidney stones include, but are not limited to, genetic hypercalciuric rats (see, e.g., Bushinsky et al., 1999, *Kidney Int* 55(1):234-43 and Bushinsky et al., 1995, *Kidney Int* 48(6):1705-13), chemically treated rats (see, e.g., Grases et al., 1998, *Scand J Urol Nephrol* 32(4): 261-5; Burgess et al., 1995, *Urol Res* 23(4):239-42; Kumar et al., 1991, *J Urol* 146(5):1384-9; Okada et al., 1985, *Hinyokika Kiyo* 31(4):565-77; and Bluestone et al., 1975, *Lab Invest* 33(3):273-9), hyperoxaluric rats (see, e.g., Jones et al., 1991, *J Urol* 145(4):868-74), pigs with unilateral retrograde flexible nephroscopy (see, e.g., Seifmah et al., 2001, 57(4): 832-6), and rabbits with an obstructed upper urinary tract (see, e.g., Itatani et al., 1979, *Invest Urol* 17(3):234-40).

Ataxia-Telangiectasia

Examples of animal models for ataxia-telangiectasia include, but are not limited to, murine models of ataxia-telangiectasia (see, e.g., Barlow et al., 1999, *Proc Natl Acad Sci USA* 96(17):9915-9 and Inoue et al., 1986, *Cancer Res* 46(8):3979-82).

Lysosomal Storage Diseases

Examples of animal models for lysosomal storage diseases include, but are not limited to, mouse models for mucopolysaccharidosis type VII (see, e.g., Brooks et al., 2002, *Proc Natl Acad Sci USA.* 99(9):6216-21; Monroy et al., 2002, *Bone* 30(2):352-9; Vogler et al., 2001, *Pediatr Dev Pathol.* 4(5):421-33; Vogler et al., 2001, *Pediatr Res.* 49(3):342-8; and Wolfe et al., 2000, *Mol Ther.* 2(6):552-6), a mouse model for metachromatic leukodystrophy (see, e.g., Matzner et al., 2002, *Gene Ther.* 9(1):53-63), a mouse model of Sandhoff disease (see, e.g., Sango et al., 2002, *Neuropathol Appl Neurobiol.* 28(1):23-34), mouse models for mucopolysaccharidosis type III A (see, e.g., Bhattacharyya et al., 2001, *Glycobiology* 11(1):99-10 and Bhaumik et al., 1999, *Glycobiology* 9(12):1389-96.), arylsulfatase A (ASA)-deficient mice (see, e.g., D'Hooge et al., 1999, *Brain Res.* 847(2):352-6 and D'Hooge et al, 1999, *Neurosci Lett.* 273(2):93-6); mice with an aspartylglucosaminuria mutation (see, e.g., Jalanko et al., 1998, *Hum Mol Genet.* 7(2):265-72); feline models of mucopolysaccharidosis type VI (see, e.g., Crawley et al., 1998, *J Clin Invest.* 101(1):109-19 and Norrdin et al., 1995, *Bone* 17(5):485-9); a feline model of Niemann-Pick disease type C (see, e.g., March et al., 1997, *Acta Neuropathol* (Berl). 94(2): 164-72); acid sphingomyelinase-deficient mice (see, e.g., Otterbach & Stoffel, 1995, *Cell* 81(7):1053-6), and bovine mannosidosis (see, e.g., Jolly et al., 1975, *Birth Defects Orig Arctic Ser.* 11(6):273-8).

Tuberous Sclerosis

Examples of animal models for tuberous sclerosis ("TSC") include, but are not limited to, a mouse model of TSC1 (see, e.g., Kwiatkowski et al., 2002, *Hum Mol Genet.* 11(5):525-34), a TSC1 (TSC1 homologue) knockout mouse (see, e.g., Kobayashi et al., 2001, *Proc Natl Acad Sci USA.* 2001 Jul. 17; 98(15):8762-7), a TSC2 gene mutant(Eker) rat model (see, e.g., Hino 2000, *Nippon Rinsho* 58(6):1255-61; Mizuguchi et al., 2000, *J Neuropathol Exp Neurol.* 59(3):188-9; and Hino et al., 1999, *Prog Exp Tumor Res.* 35:95-108); and Tsc2(+/−) mice (see, e.g., Onda et al., 1999, *J Clin Invest.* 104(6):687-95).

Example 5

Mdx Mouse, an Animal Model Study

The mutation in the mdx mouse that causes premature translation termination of the 427 kDa dystrophin polypeptide has been shown to be a C to T transition at position 3185 in exon 23 (Sicinski et al., *Science* 244(4912):1578-1580 (1989)). Mouse primary skeletal muscle cultures derived from 1-day old mdx mice are prepared as described previously (Barton-Davis et al., *J Clin. Invest.* 104(4):375-381 (1999)). Cells are cultured for 10 days in the presence of a compound of the invention. Culture medium is replaced every four days and the presence of dystrophin in myoblast cultures is detected by immunostaining as described previously (Barton-Davis et al., *J. Clin. Invest.* 104(4):375-381(1999)). A primary monoclonal antibody to the C-terminus of the dystrophin protein is used undiluted and rhodamine conjugated anti-mouse IgG is used as the secondary antibody. The antibody detects the full-length protein produced by suppression of the nonsense codon. Staining is viewed using a Leica DMR microscope, digital camera, and associated imaging software.

As previously described (Barton-Davis et al., *J. Clin. Invest.* 104(4):375-381(1999), compound is delivered by Alzet osmotic pumps implanted under the skin of anesthetized mice. Two doses of a compound of the invention are administered. Gentamicin serves as a positive control and pumps filled with solvent only serve as the negative control. Pumps are loaded with appropriate compound such that the calculated doses to which tissue is exposed are 10 mM and 20 mM. The gentamicin concentration is calculated to achieve tissue exposure of approximately 200 mM. In the initial experiment, mice are treated for 14 days, after which animals are anesthetized with ketamine and exsanguinated. The tibialis anterior (TA) muscle of the experimental animals is then excised, frozen, and used for immunofluorescence analysis of dystrophin incorporation into striated muscle. The presence of dystrophin in TA muscles is detected by immunostaining, as described previously (Barton-Davis et al., *J. Clin. Invest.* 104(4):375-381(1999).

Western Blot Analysis

Quadricep muscles from an mdx mouse treated with a compound of the present invention for 4 weeks are analyzed by western blot using a commercially available antibody to dystrophin. Protein extracted from the quadriceps of a wild-type mouse serve as a positive control. Production of full-length dystrophin is observed in the treated animal. The amount of full-length dystrophin produced, as a result of nonsense suppression, but not limited by this theory, is approximately 10% of wild-type levels of expression.

Immunofluorescence

Male mdx mice (age 9-11 weeks) are treated with different compounds of the present inventin (n=2 at least for each compound). These compounds are injected SQ once per day for two weeks at 25 mg/kg. After 2 weeks of treatment, mice are sacrificed for the removal of muscles to determine dystrophin readthrough efficiency.

Immunofluorescence (IF) is performed on 10 μm cryosections using a dystrophin antibody. The antibody recognizes an epitope C-terminal to the premature stop mutation found in mdx mice. Image analysis is performed in an identical manner in all sections. Images from treated and untreated mice are analyzed and a signal greater than the signal on the untreated control is deemed positive and indicates that suppression of the premature termination codon in the dystrophin mRNA occurred.

Muscle Mechanics

Isolated whole muscle mechanics is performed on EDL muscles from animals. Optimum muscle length (Lo) is defined as the length that produced maximum twitch tension. Maximum tetanic force at Lo is measured using a 120 Hz, 500 msec pulse at supramaximal voltage. Protection against mechanical injury, induced by a series of 5 eccentric tetanic contractions, is monitored. These measurements are performed using a 700 msec stimulation period during which the muscle is held in an isometric contraction for the first 500 msec followed by a stretch of 8 or 10% Lo at a rate of 0.5 Lo/sec. Protection against mechanical injury is evaluated at 80 Hz stimulation frequency. Damage is determined as the loss in force between the first and last eccentric contraction.

Example 6

Suppression of a Nonsense Mutation in the p53 Gene

For an animal model system, CAOV-3 cells ($1\times10^7$) are injected into the flanks of nude/nude mice. After 12 days, mice are randomized (10 mice per group) and treated subcutaneously (5 days per week) with 3 mg/kg of a compound of the present invention or intraperitonealy (1 day per week) with 30 mg/kg of a compound of the present invention. Tumor volumes are measured weekly. Suppression of nonsense mutations in the p53 gene by a compound of the present invention can inhibit cancer growth in vivo.

Example 7

Access to Specific Nucleotides of the 28S rRNA can be Modified by Compounds of the Present Invention Previous studies have demonstrated that gentamicin and other members of the aminoglycoside family that decrease the fidelity of translation bind to the A site of the 16S rRNA. By chemical footprinting, UV cross-linking and NMR, gentamicin has been shown to bind at the A site (comprised of nucleotides 1400-1410 and 1490-1500, *E. coli* numbering) of the rRNA at nucleotides 1406, 1407, 1494, and 1496 (Moazed & Noller, *Nature* 327(6121):389-394 (1978); Woodcock et al., *EMBO J.* 10(10):3099-3103 (1991); and Schroeder et al., *EMBO J* 19:1-9 (2000).

Ribosomes prepared from HeLa cells are incubated with the small molecules (at a concentration of 100 mM), followed by treatment with chemical modifying agents (dimethyl sulfate [DMS] and kethoxal [KE]). Following chemical modification, rRNA is phenol-chloroform extracted, ethanol precipitated, analyzed in primer extension reactions using end-labeled oligonucleotides hybridizing to different regions of the three rRNAs and resolved on 6% polyacrylamide gels. Probes for primer extension cover the entire 18S (7 oligonucleotide primers), 28S (24 oligonucleotide primers), and 5S (one primer) rRNAs. Controls in these experiments include DMSO (a control for changes in rRNA accessibility induced by DMSO), paromomycin (a marker for 18S rRNA binding), and anisomycin (a marker for 28S rRNA binding).

All publications and patent applications cited herein are incorporated by reference to the same extent as if each individual publication or patent application was specifically and individually indicated to be incorporated by reference.

Although certain embodiments have been described in detail above, those having ordinary skill in the art will clearly understand that many modifications are possible in the embodiments without departing from the teachings thereof. All such modifications are intended to be encompassed within the claims of the invention.

What is claimed:
1. A compound of Formula 1-B or 1-D:

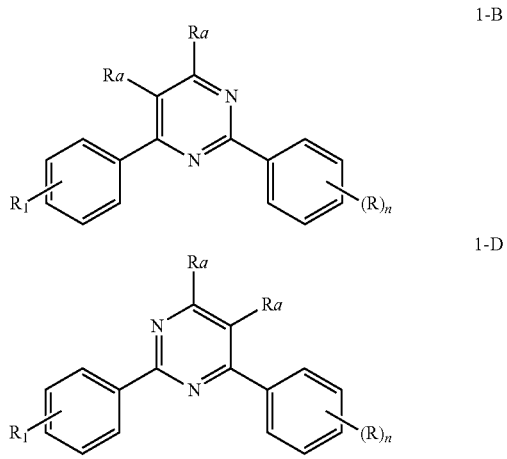

wherein:
$R_a$ is hydrogen or a $C_1$-$C_4$ alkyl group;
n is 1, 2, or 3;
$R_1$ is a cyano group; or a carbonyl group which is substituted with a hydroxy, a $C_1$-$C_4$ alkyl, or a $C_1$-$C_4$ alkoxy group;
R is independently selected from a hydroxy group; a halogen; a $C_1$-$C_4$ alkyl which is optionally substituted with one or more independently selected halogen or hydroxy groups; a $C_1$-$C_4$ alkoxy which is optionally substituted with one or more independently selected halogen or phenyl groups; a $C_4$-$C_8$ cycloalkyl which is optionally substituted with one or more independently selected $C_1$-$C_4$ alkyl groups; an —$R_b$ group; a —O—$R_b$ group; a five to six-membered heterocycle which is optionally substituted with one or more independently selected $C_1$-$C_4$ alkyl, oxo, or —$R_b$ groups; a nine to ten membered heterocycle having two ring structures; a carbonyl which is substituted with a $C_1$-$C_4$ alkyl, or a $C_1$-$C_4$ alkoxy group; a carbamoyl which is optionally substituted with one or two $C_1$-$C_4$ alkyl groups; a nitro group; a thio which is optionally substituted with a hydroxy, a $C_1$-$C_4$ alkyl, or —$R_b$ group; a sulfonyl which is optionally substituted with a hydroxy, a $C_1$-$C_4$ alkyl, or —$R_b$ group; an amino which is optionally substituted with one or two independently selected $C_1$-$C_4$ alkyl, sulfonyl, or carbonyl groups, wherein the aminosulfonyl group is optionally substituted with a hydroxy, a $C_1$-$C_4$ alkyl, or an —$R_b$ group, and wherein the aminocarbonyl group is optionally substituted with a $C_1$-$C_4$ alkyl, a $C_1$-$C_4$ haloalkyl, a benzoxy, or an amino group which is optionally substituted with an —$R_b$ group; or two R groups together with the phenyl ring to which they are attached form a benzo[1,3]dioxole or a 2,3-dihydro-benzo[1,4]dioxinyl group; wherein
$R_b$ is a $C_6$-$C_8$ aryl which is optionally substituted with one or more of the following: a hydroxy, a halogen, a $C_1$-$C_4$ alkyl group, a $C_1$-$C_4$ haloalkyl group, a $C_1$-$C_4$ alkoxy group, or an amino group which is optionally substituted with one or more $C_1$-$C_4$ alkyl groups;
wherein $R_1$ is in the meta or para position when said compound is a compound of Formula 1-B; or a pharmaceutically acceptable salt thereof.

2. A compound selected from the group consisting of:
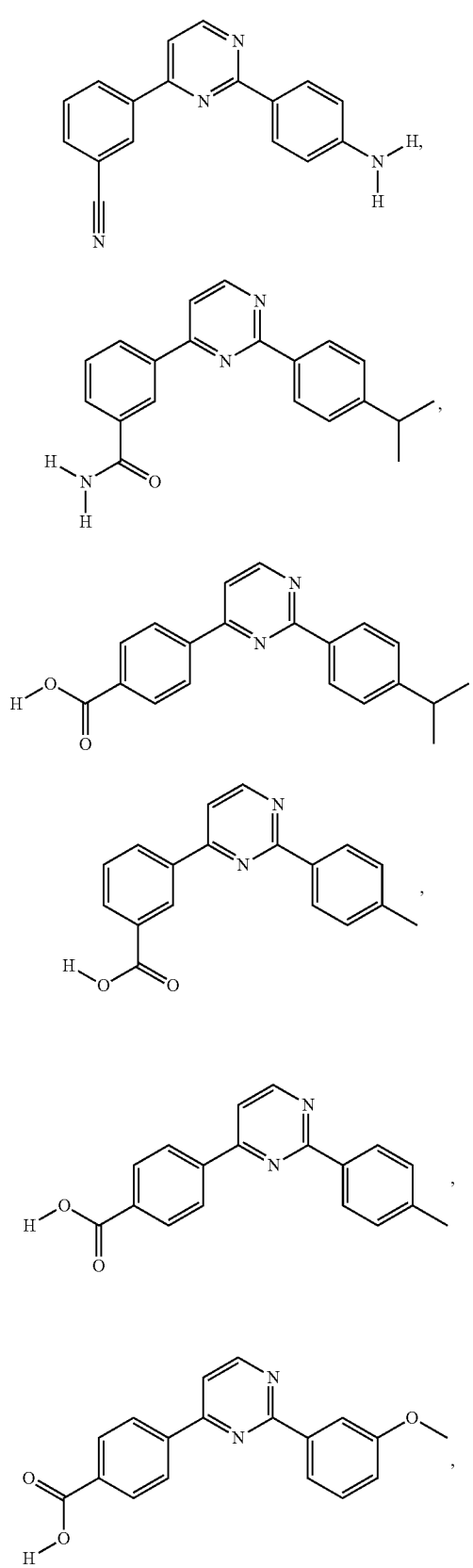
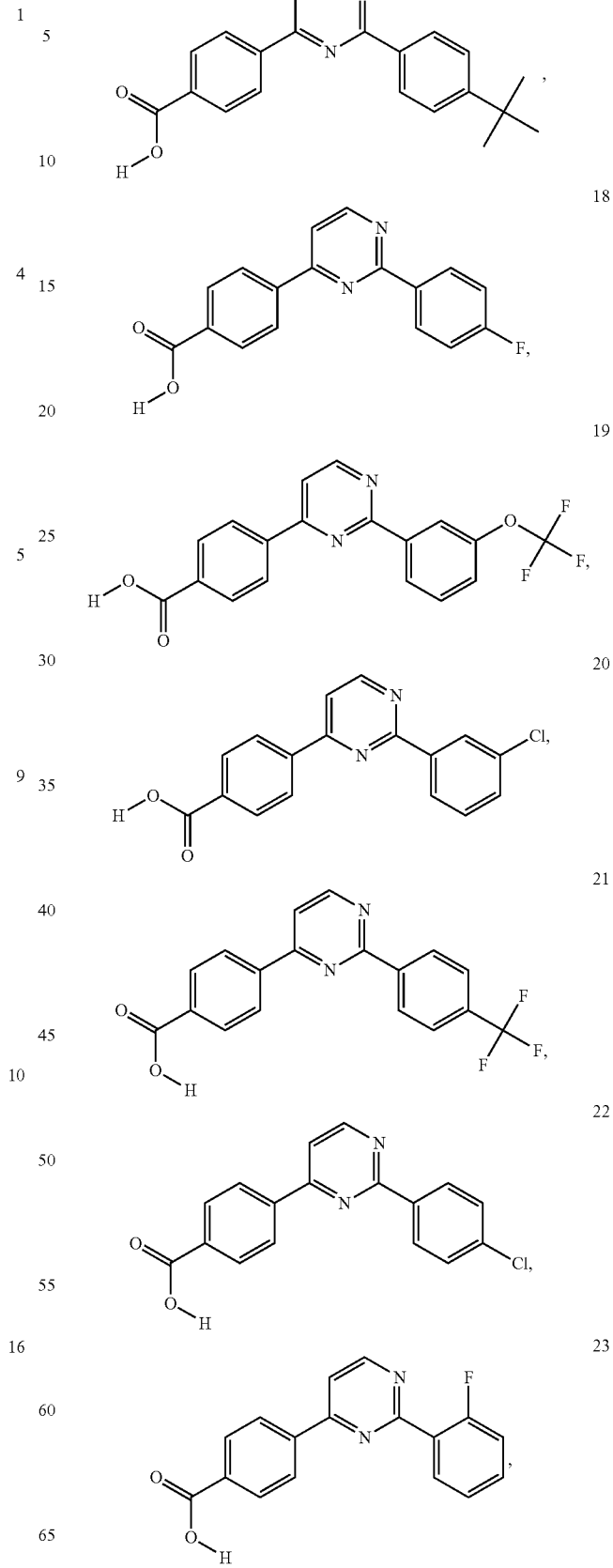

25 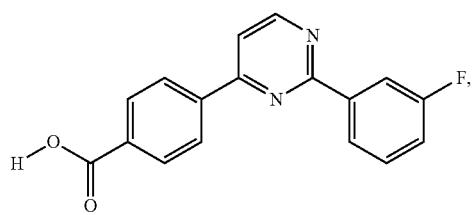
26 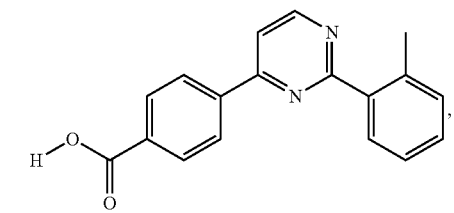
27 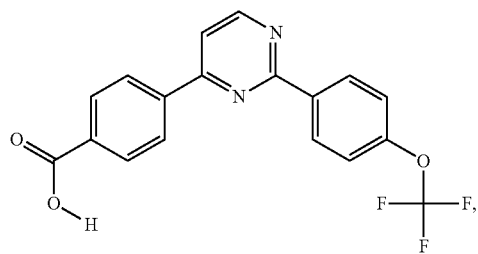
28 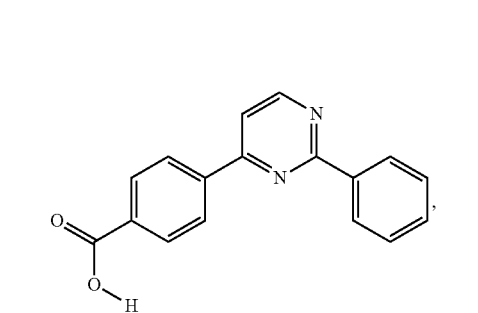
29 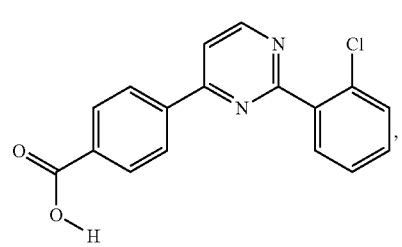
30 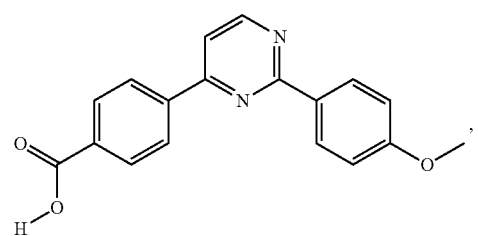
31 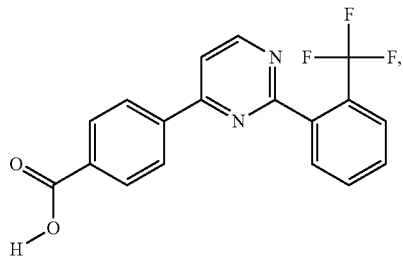
32 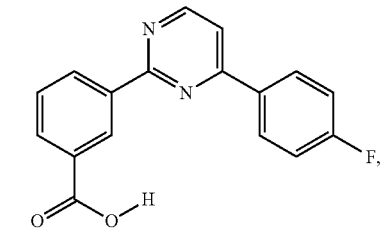
33 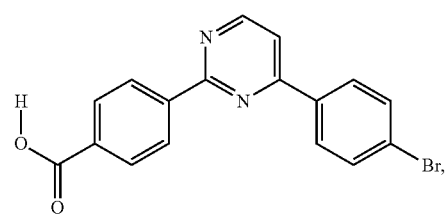
34 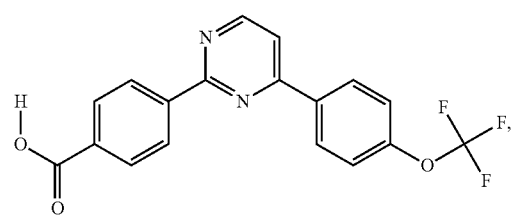
35 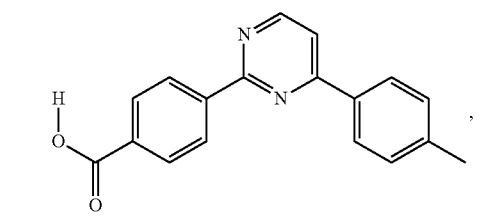
36 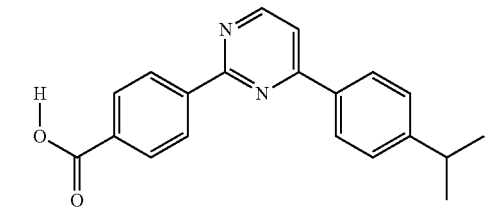
37 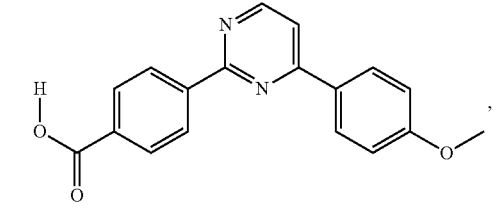

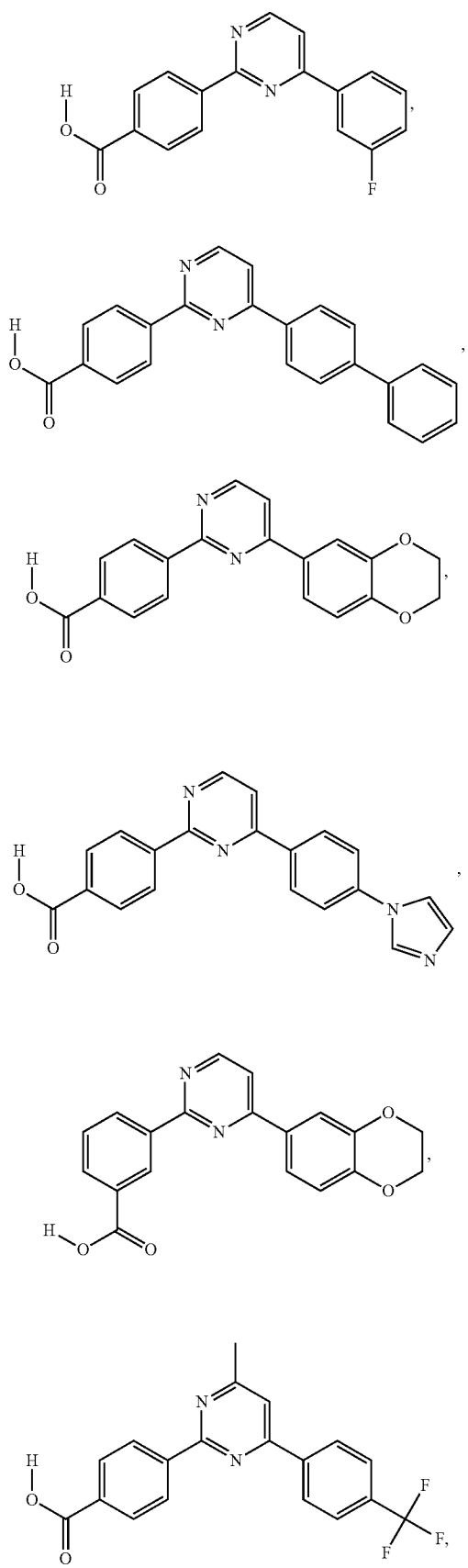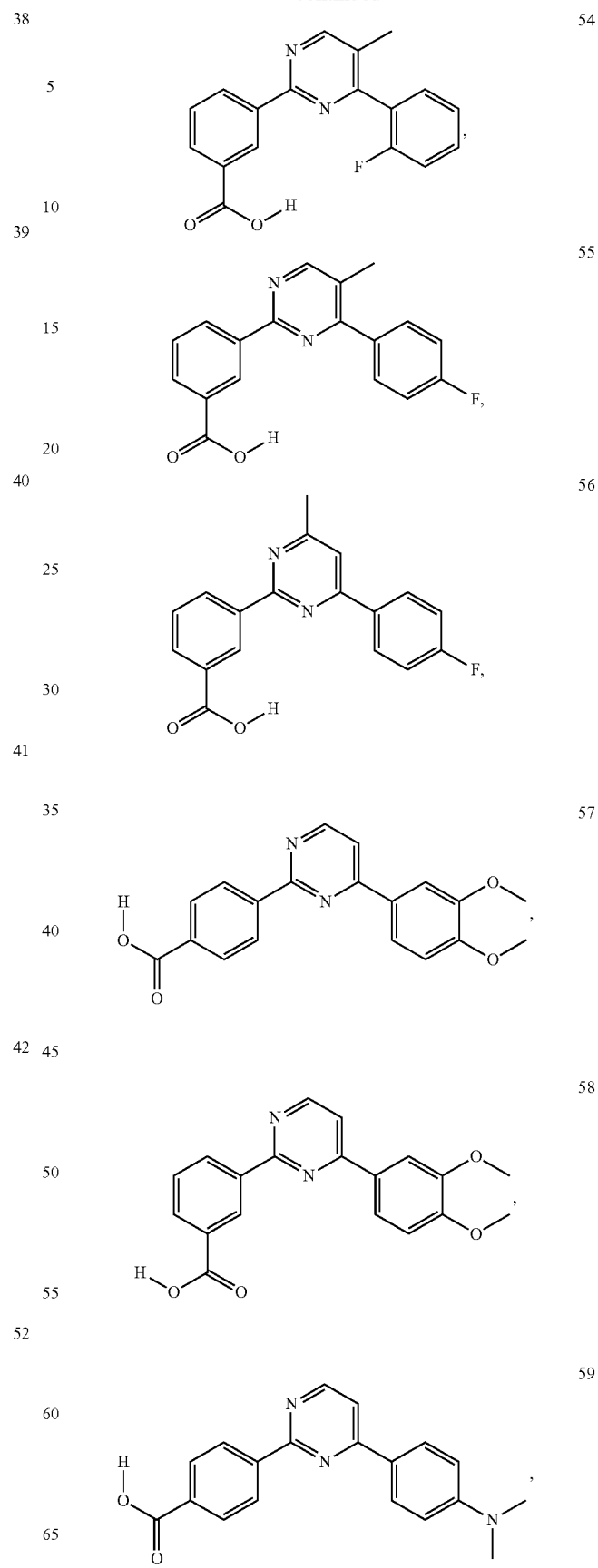

127
-continued
60
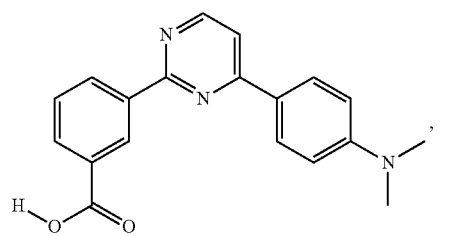
61
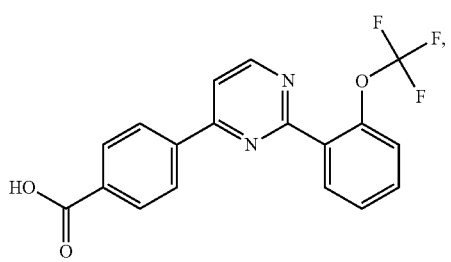
62
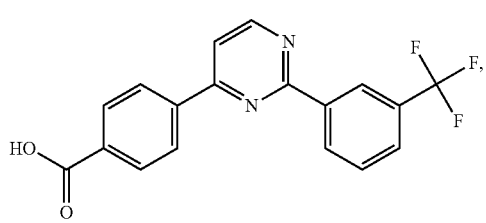
63
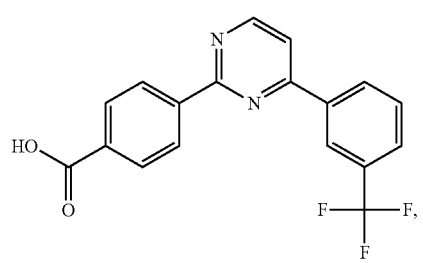
64
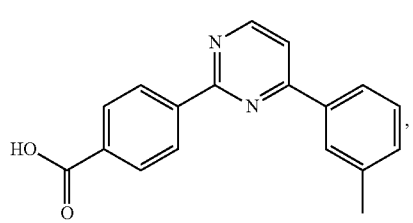
65
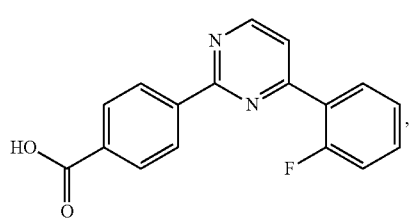
66
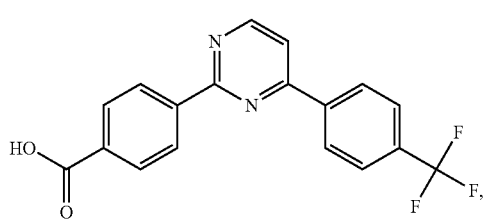
128
-continued
67
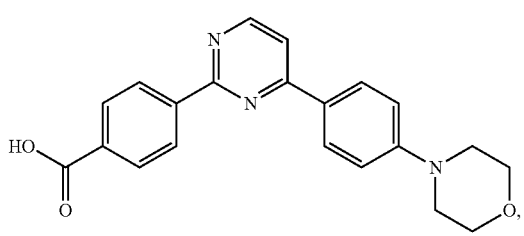
68
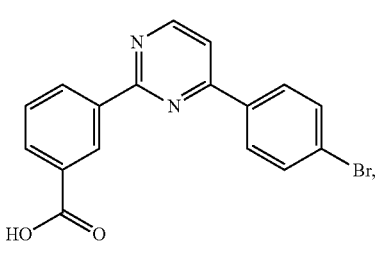
69
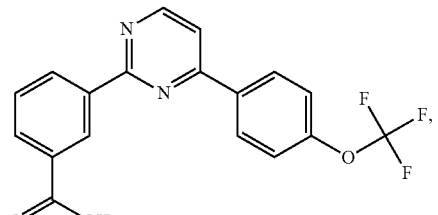
70
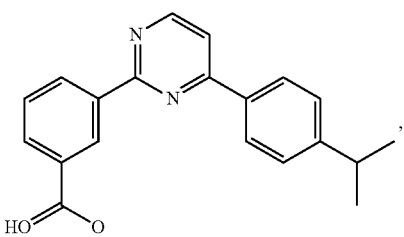
71
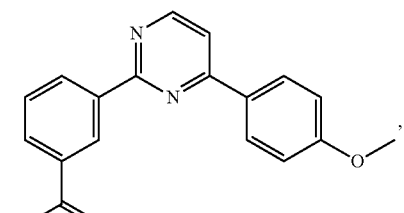
72
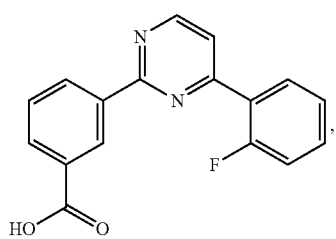

73 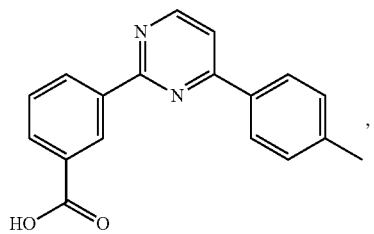

74 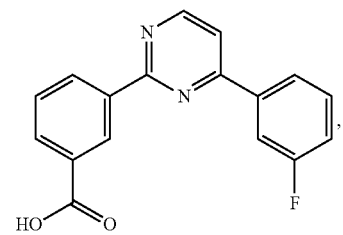

75 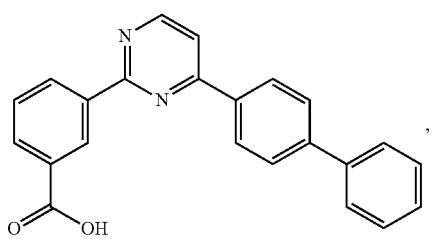

76 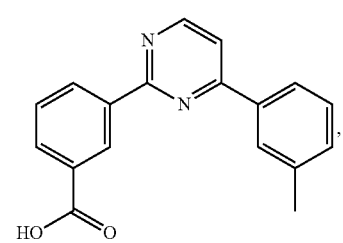

77 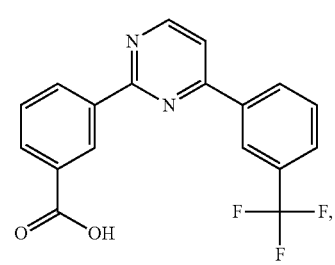

78 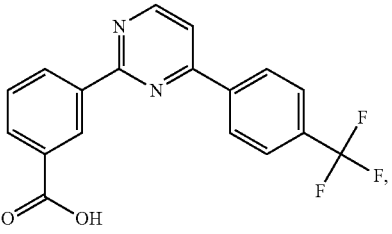

79 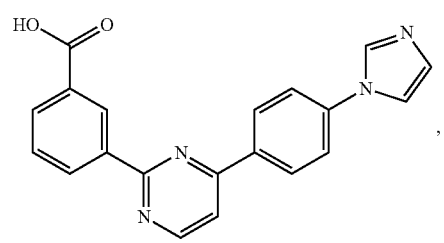

and pharmaceutically acceptable salts thereof.

3. The compound of claim 1, wherein
$R_a$ is hydrogen or a $C_1$-$C_4$ alkyl group;
n is 1, or 2;
$R_1$ is a cyano group; or a carbonyl group which is substituted with a hydroxy;
R is independently selected from a hydroxy group; a halogen; a $C_1$-$C_4$ alkyl which is optionally substituted with one or more independently selected halogen groups; a $C_1$-$C_4$ alkoxy which is optionally substituted with one or more independently selected halogen groups; an —$R_b$ group; a five to six-membered heterocycle; an amino which is optionally substituted with one or two independently selected $C_1$-$C_4$ alkyl groups; or two R groups together with the phenyl ring to which they are attached form a benzo[1,3]dioxole or a 2,3-dihydro-benzo[1,4]dioxinyl group; wherein —$R_b$ is a $C_6$-$C_8$ aryl;
or a pharmaceutically acceptable salt thereof.

4. The compound of claim 3, wherein $R_1$ is a carboxy group.

5. The compound of claim 3, wherein R is independently selected from chloro, fluoro, bromo, methyl, isopropyl, tert-butyl, trifluoromethyl, methoxy, ethoxy, trifluoromethoxy, amino, dimethylamino, or two R groups together with the phenyl ring to which they are attached form a 2,3-dihydro-benzo[1,4]dioxinyl group.

6. The compound of claim 5, wherein R is selected from methyl, fluoro, methoxy, ethoxy or trifluoromethyl.

7. The compound of claim 3, wherein $R_a$ is hydrogen or methyl.

8. The compound of claim 6, wherein R is located in one or more ortho position, one or more meta position, or a para position.

\* \* \* \* \*